(12) United States Patent
Burgess et al.

(10) Patent No.: US 11,666,720 B2
(45) Date of Patent: Jun. 6, 2023

(54) FLOW PATH SENSING FOR FLOW THERAPY APPARATUS

(71) Applicant: Fisher & Paykel Healthcare Limited, Auckland (NZ)

(72) Inventors: Russel William Burgess, Auckland (NZ); Jess Edward Donnelly, Auckland (NZ); Dean Antony Barker, Auckland (NZ); Philip John Dickinson, Auckland (NZ); Andre Van Schalkwyk, Auckland (NZ); Joel Michael Lawson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 157 days.

(21) Appl. No.: 15/780,020

(22) PCT Filed: Dec. 2, 2016

(86) PCT No.: PCT/NZ2016/050193
§ 371 (c)(1),
(2) Date: May 30, 2018

(87) PCT Pub. No.: WO2017/095241
PCT Pub. Date: Jun. 8, 2017

(65) Prior Publication Data
US 2020/0179629 A1 Jun. 11, 2020

Related U.S. Application Data

(60) Provisional application No. 62/262,325, filed on Dec. 2, 2015.

(51) Int. Cl.
*A61M 16/00* (2006.01)
*A61M 16/20* (2006.01)
(Continued)

(52) U.S. Cl.
CPC ...... *A61M 16/026* (2017.08); *A61M 16/0066* (2013.01); *A61M 16/12* (2013.01);
(Continued)

(58) Field of Classification Search
CPC .............. A61M 16/026; A61M 16/204; A61M 16/0066; A61M 16/12; A61M 16/16;
(Continued)

(56) References Cited

U.S. PATENT DOCUMENTS 1,269,599 A 6/1918 Leiser
1,570,781 A 6/1926 Ruben
(Continued)

FOREIGN PATENT DOCUMENTS

AU 2014202639 12/2014
CN 1336536 A 2/2002
(Continued)

OTHER PUBLICATIONS

International Search Report and Written Opinion for PCT/NZ2016/050193 dated Jun. 7, 2017 in 29 pages.
(Continued)

*Primary Examiner* — Timothy A Stanis
*Assistant Examiner* — Matthew R Moon
(74) *Attorney, Agent, or Firm* — Knobbe, Martens, Olson & Bear, LLP

(57) ABSTRACT

A respiratory flow therapy apparatus including a sensing chamber which measures a flow of gases provided to a patient. The sensing chamber can be located after a blower and/or mixer. The sensing chamber can include an ultrasonic transducer, a temperature sensor, a heated temperature sensing element, and/or a gas concentration sensor. A flow path of gases used in conjunction with the sensor system prevents unwanted vorticity in the flow of gases that can create anomalies in measuring flow.

13 Claims, 34 Drawing Sheets

(51) Int. Cl.
*A61M 16/12* (2006.01)
*A61M 16/16* (2006.01)
*A61M 16/06* (2006.01)
*A61M 16/10* (2006.01)

(52) U.S. Cl.
CPC .......... *A61M 16/16* (2013.01); *A61M 16/204* (2014.02); *A61M 16/0672* (2014.02); *A61M 16/161* (2014.02); *A61M 2016/0027* (2013.01); *A61M 2016/0033* (2013.01); *A61M 2016/1025* (2013.01); *A61M 2205/3368* (2013.01); *A61M 2205/3375* (2013.01); *A61M 2205/42* (2013.01); *A61M 2205/505* (2013.01); *A61M 2205/702* (2013.01)

(58) Field of Classification Search
CPC ............ A61M 16/0672; A61M 16/161; A61M 2016/0027; A61M 2016/0033; A61M 2016/1025; A61M 2205/3368; A61M 2205/3375; A61M 2205/42; A61M 2205/505; A61M 2205/702; A61M 16/101; A61M 16/0069; A61M 16/107; A61M 16/109; A61M 16/1095; A61M 2016/0039; A61M 2205/3553; A61M 2205/3569; A61M 2205/3592; A61M 2209/02; A61M 16/0051; A61M 16/1055; A61M 16/0003
See application file for complete search history.

(56) References Cited

U.S. PATENT DOCUMENTS

| | | |
|---|---|---|
| 2,283,750 A | 5/1942 | Mikelson |
| 2,568,277 A | 9/1951 | Eltgroth |
| 2,874,564 A | 2/1959 | Martin et al. |
| 2,984,097 A | 5/1961 | Kniazuk et al. |
| 3,120,750 A | 2/1964 | Root, III |
| 3,343,403 A | 9/1967 | Romani et al. |
| 3,468,157 A | 9/1969 | Burk et al. |
| 3,495,628 A | 2/1970 | Boender |
| 3,724,484 A | 4/1973 | Turman |
| 3,762,197 A | 10/1973 | Roof et al. |
| 3,805,590 A | 4/1974 | Ringwall et al. |
| 3,848,457 A | 11/1974 | Behymer |
| 3,863,630 A | 2/1975 | Cavallo |
| 3,926,223 A | 12/1975 | Petzetakis |
| 3,981,176 A | 9/1976 | Jacobs |
| 4,033,808 A | 7/1977 | Petzetakis |
| 4,155,246 A | 5/1979 | Dempster et al. |
| 4,215,409 A | 7/1980 | Strowe |
| 4,220,040 A | 9/1980 | Noguchi et al. |
| 4,255,964 A | 3/1981 | Morison |
| 4,280,183 A | 7/1981 | Santi |
| 4,313,436 A | 2/1982 | Schwanbom et al. |
| 4,326,513 A | 4/1982 | Schulz et al. |
| 4,331,025 A | 5/1982 | Ord, Jr. |
| 4,340,044 A | 7/1982 | Levy et al. |
| 4,345,612 A | 8/1982 | Koni et al. |
| 4,380,167 A | 4/1983 | Longini |
| 4,452,090 A | 6/1984 | Kou et al. |
| 4,520,654 A | 6/1985 | Terhune |
| 4,531,551 A | 7/1985 | Eichelberger et al. |
| 4,555,932 A | 12/1985 | Crosby, Jr. |
| 4,662,212 A | 5/1987 | Noguchi et al. |
| 4,773,448 A | 9/1988 | Francis |
| 4,889,116 A | 12/1989 | Taube |
| 4,903,736 A | 2/1990 | Baston et al. |
| 4,938,066 A | 7/1990 | Dorr |
| 4,989,595 A | 2/1991 | De Vuono et al. |
| 5,060,506 A | 10/1991 | Douglas |
| 5,060,507 A | 10/1991 | Urmson et al. |
| 5,060,514 A | 10/1991 | Aylsworth |
| 5,127,442 A | 7/1992 | Blomqvist |
| 5,179,862 A | 1/1993 | Lynnworth |
| 5,247,826 A | 9/1993 | Frola et al. |
| 5,285,677 A | 2/1994 | Oehler |
| 5,313,820 A | 5/1994 | Aylsworth |
| 5,343,760 A | 9/1994 | Sultan et al. |
| 5,351,522 A | 10/1994 | Lura |
| 5,359,897 A | 11/1994 | Hamstead et al. |
| 5,365,922 A | 11/1994 | Raemer |
| 5,392,635 A | 2/1995 | Cadet et al. |
| 5,452,621 A | 9/1995 | Aylesworth et al. |
| 5,452,714 A | 9/1995 | Anderson et al. |
| 5,460,175 A | 10/1995 | Foote et al. |
| 5,463,906 A | 11/1995 | Spani et al. |
| 5,490,763 A | 2/1996 | Abrams et al. |
| 5,503,151 A | 4/1996 | Harnoncourt et al. |
| 5,551,419 A | 9/1996 | Froehlich et al. |
| 5,581,014 A | 12/1996 | Douglas |
| 5,591,292 A | 1/1997 | Blomqvist |
| 5,625,140 A | 4/1997 | Cadet et al. |
| 5,627,323 A | 5/1997 | Stern |
| 5,640,951 A | 6/1997 | Huddart et al. |
| 5,701,883 A | 12/1997 | Hete et al. |
| 5,792,665 A | 8/1998 | Morrow, III |
| 5,809,997 A * | 9/1998 | Wolf .................. A61M 15/009 128/200.23 |
| 5,823,186 A | 10/1998 | Rossen et al. |
| 5,917,135 A | 6/1999 | Michaels et al. |
| 6,039,696 A | 3/2000 | Bell |
| 6,041,777 A | 3/2000 | Faithfull et al. |
| 6,105,649 A | 8/2000 | Levingston et al. |
| 6,123,074 A | 9/2000 | Hete et al. |
| 6,138,674 A | 10/2000 | Gull et al. |
| 6,142,149 A | 11/2000 | Steen |
| 6,178,827 B1 | 1/2001 | Feller |
| 6,279,379 B1 | 8/2001 | Logue et al. |
| 6,397,841 B1 | 6/2002 | Kenyon et al. |
| 6,487,916 B1 | 12/2002 | Gomm et al. |
| 6,537,405 B1 | 3/2003 | Henderson et al. |
| 6,543,449 B1 | 4/2003 | Woodring et al. |
| 6,581,595 B1 | 6/2003 | Murdock et al. |
| 6,629,934 B2 | 10/2003 | Mault et al. |
| 6,634,356 B1 | 10/2003 | O'Dea et al. |
| 6,910,481 B2 | 6/2005 | Kimmel et al. |
| 7,063,668 B2 | 6/2006 | Cardelius et al. |
| 7,066,175 B2 | 6/2006 | Hamilton et al. |
| 7,111,624 B2 | 9/2006 | Thudor et al. |
| 7,183,552 B2 | 2/2007 | Russell |
| 7,370,651 B2 | 5/2008 | Holder |
| 7,432,508 B2 | 10/2008 | Daniels et al. |
| 7,448,376 B2 | 11/2008 | Lepel |
| 7,501,630 B2 | 3/2009 | Russell |
| 7,509,957 B2 | 3/2009 | Duquette et al. |
| 7,606,668 B2 | 10/2009 | Pierry et al. |
| 7,810,497 B2 | 10/2010 | Pittman et al. |
| 8,042,535 B2 | 10/2011 | Kenyon et al. |
| 8,047,082 B2 | 11/2011 | Bierl |
| 8,100,124 B2 | 1/2012 | Becker et al. |
| 8,381,722 B2 | 2/2013 | Berthon-jones |
| 8,485,183 B2 | 7/2013 | Masic |
| 8,561,611 B2 | 10/2013 | Shissler et al. |
| 8,746,037 B2 | 6/2014 | Matsuzaki |
| 8,752,544 B2 | 6/2014 | Bottom |
| 8,875,587 B2 | 11/2014 | Wiest et al. |
| 9,119,933 B2 | 9/2015 | Bedford et al. |
| 9,149,590 B2 | 10/2015 | Wallen |
| 9,302,066 B2 | 4/2016 | Bertinetti et al. |
| 9,649,459 B2 | 5/2017 | Taylor et al. |
| 10,357,629 B2 | 7/2019 | Barker et al. |
| 2002/0062681 A1 | 5/2002 | Livingston |
| 2003/0065274 A1 | 4/2003 | Mault et al. |
| 2004/0211244 A1 | 10/2004 | Cardelius et al. |
| 2005/0121033 A1 | 6/2005 | Starr et al. |
| 2005/0125170 A1 | 6/2005 | Gysling et al. |
| 2005/0223795 A1 | 10/2005 | Gerder et al. |
| 2006/0042638 A1 | 3/2006 | Niklewski et al. |
| 2006/0113690 A1 | 6/2006 | Huddart et al. |
| 2006/0156828 A1 | 7/2006 | Konzelmann et al. |
| 2006/0158956 A1 | 7/2006 | Laugharn, Jr. et al. |
| 2006/0283450 A1 | 12/2006 | Shissler et al. |

(56) References Cited

U.S. PATENT DOCUMENTS

| | | | |
|---|---|---|---|
| 2007/0044799 A1 | 3/2007 | Hete et al. | |
| 2007/0062531 A1* | 3/2007 | Fisher | A61M 16/206 |
| | | | 128/204.23 |
| 2007/0125374 A1 | 6/2007 | Smith et al. | |
| 2007/0245802 A1 | 10/2007 | Austerlitz et al. | |
| 2007/0283958 A1 | 12/2007 | Naghavi | |
| 2008/0041381 A1 | 2/2008 | Tham et al. | |
| 2008/0060647 A1 | 3/2008 | Messenger et al. | |
| 2008/0092891 A1 | 4/2008 | Cewers | |
| 2008/0156328 A1 | 7/2008 | Taube | |
| 2009/0020120 A1 | 1/2009 | Schatzl et al. | |
| 2009/0056715 A1 | 3/2009 | Cortez, Jr. et al. | |
| 2009/0107501 A1 | 4/2009 | Krieger | |
| 2009/0145428 A1 | 6/2009 | Sward et al. | |
| 2009/0178490 A1 | 7/2009 | Konzelmann et al. | |
| 2009/0241953 A1 | 10/2009 | Vandine et al. | |
| 2010/0006098 A1 | 1/2010 | McGinnis et al. | |
| 2010/0126249 A1 | 5/2010 | Matsuzaki | |
| 2010/0218591 A1 | 9/2010 | Rhodes et al. | |
| 2010/0224191 A1 | 9/2010 | Dixon et al. | |
| 2011/0120462 A1 | 5/2011 | Tatkov et al. | |
| 2011/0209558 A1 | 9/2011 | Sugiura et al. | |
| 2011/0314897 A1 | 12/2011 | Schellekens et al. | |
| 2012/0006326 A1* | 1/2012 | Ahmad | A61M 16/024 |
| | | | 128/204.22 |
| 2012/0055340 A1 | 3/2012 | Wilkinson et al. | |
| 2012/0065533 A1 | 3/2012 | Carrillo, Jr. et al. | |
| 2012/0109536 A1 | 5/2012 | Pasveer et al. | |
| 2012/0125121 A1 | 5/2012 | Gottlieb et al. | |
| 2012/0271188 A1 | 10/2012 | Van Kesteren | |
| 2013/0008438 A1 | 1/2013 | Sugawara et al. | |
| 2013/0239960 A1 | 9/2013 | Bertinetti et al. | |
| 2013/0263854 A1* | 10/2013 | Taylor | A61M 16/107 |
| | | | 128/204.23 |
| 2013/0267863 A1 | 10/2013 | Orr | |
| 2014/0007878 A1 | 1/2014 | Armitstead et al. | |
| 2014/0034051 A1 | 2/2014 | Addington et al. | |
| 2014/0137859 A1 | 5/2014 | Wilkinson et al. | |
| 2014/0261414 A1* | 9/2014 | Weitzel | A61M 15/0051 |
| | | | 128/203.14 |
| 2014/0311253 A1 | 10/2014 | Iwasa | |
| 2015/0048530 A1 | 2/2015 | Cheung et al. | |
| 2015/0059745 A1 | 3/2015 | Barker et al. | |
| 2015/0101600 A1* | 4/2015 | Miller | A61M 16/06 |
| | | | 128/203.14 |
| 2015/0107587 A1 | 4/2015 | Zhang | |
| 2015/0136129 A1 | 5/2015 | Mahadevan et al. | |
| 2015/0238722 A1* | 8/2015 | Al-Ali | A61M 16/085 |
| | | | 128/205.13 |
| 2015/0283339 A1 | 10/2015 | Mahadevan et al. | |
| 2015/0327807 A1* | 11/2015 | Bronner | A61M 16/0875 |
| | | | 600/531 |
| 2016/0082220 A1 | 3/2016 | Barker et al. | |
| 2016/0114121 A1 | 4/2016 | Holley et al. | |
| 2016/0151601 A1 | 6/2016 | Cardelius et al. | |
| 2016/0228670 A1* | 8/2016 | Av-Gay | A61M 16/20 |
| 2016/0287139 A1* | 10/2016 | Luttrell | A61M 16/0006 |
| 2016/0287824 A1 | 10/2016 | Chang | |
| 2016/0354573 A1* | 12/2016 | Buswell | A61M 16/024 |
| 2017/0197056 A1 | 7/2017 | Van Schalkwyk et al. | |
| 2018/0236191 A1 | 8/2018 | Martin et al. | |
| 2018/0250481 A1* | 9/2018 | Salamitou | A61M 16/0003 |
| 2019/0269874 A1 | 9/2019 | Barker et al. | |

FOREIGN PATENT DOCUMENTS

| | | | |
|---|---|---|---|
| CN | 1455865 A | 11/2003 | |
| CN | 1817378 A | 8/2006 | |
| CN | 101152592 | 4/2008 | |
| CN | 101318049 A | 12/2008 | |
| CN | 101554510 A | 10/2009 | |
| CN | 201379872 Y | 1/2010 | |
| CN | 101680859 A | 3/2010 | |
| CN | 101861182 | 10/2010 | |
| CN | 102105189 A | 6/2011 | |
| CN | 102261937 A | 11/2011 | |
| CN | 101252966 B | 7/2012 | |
| CN | 102316920 B | 9/2015 | |
| DE | 404809 | 10/1924 | |
| EP | 0896671 B1 | 4/1997 | |
| EP | 0788805 A2 | 8/1997 | |
| EP | 813060 | 12/1997 | |
| EP | 1083427 B1 | 3/2001 | |
| EP | 1138341 A2 | 10/2001 | |
| EP | 1205747 A2 | 5/2002 | |
| EP | 1286159 A1 | 2/2003 | |
| EP | 1961439 | 8/2008 | |
| EP | 2154526 A1 | 2/2010 | |
| EP | 2200687 B1 | 6/2015 | |
| EP | 2833953 B1 | 1/2019 | |
| GB | 191408838 A * | 10/1914 | ............ A61M 16/12 |
| GB | 2087559 | 5/1982 | |
| JP | 55-004528 | 1/1980 | |
| JP | S58-190439 | 12/1983 | |
| JP | H01-321508 | 12/1989 | |
| JP | 10-073574 | 3/1998 | |
| JP | 2001-120661 | 5/2001 | |
| JP | 2011-120661 | 5/2001 | |
| JP | 2002-214012 | 7/2002 | |
| JP | 2002-306603 | 10/2002 | |
| JP | 2002-306603 A | 10/2002 | |
| JP | 2005-537083 | 12/2005 | |
| JP | 2008-518640 | 6/2008 | |
| JP | 2010-537779 | 12/2010 | |
| JP | 2011-521705 | 7/2011 | |
| JP | 2018-118085 A | 8/2018 | |
| WO | WO 95/28193 | 10/1995 | |
| WO | WO 2000/045883 A1 | 8/2000 | |
| WO | WO 03/090903 | 11/2003 | |
| WO | WO 2004/039444 | 5/2004 | |
| WO | WO 2004/069922 | 8/2004 | |
| WO | WO 2004/112873 | 12/2004 | |
| WO | WO 2007/004898 | 1/2007 | |
| WO | WO 2007/069922 | 6/2007 | |
| WO | WO 2007/103855 A2 | 9/2007 | |
| WO | WO 2008/149868 | 12/2008 | |
| WO | WO 2009/045198 | 4/2009 | |
| WO | WO 2009/052631 | 4/2009 | |
| WO | WO 2009/058081 | 5/2009 | |
| WO | WO 2009/145646 A1 | 12/2009 | |
| WO | WO 2010/084183 A2 | 7/2010 | |
| WO | WO 2011/010191 | 1/2011 | |
| WO | WO 2011/058196 | 5/2011 | |
| WO | WO 2011/058196 A1 | 5/2011 | |
| WO | WO 2011/0157196 | 5/2011 | |
| WO | WO 2011/075030 | 6/2011 | |
| WO | WO 2012/021557 | 2/2012 | |
| WO | WO 2013/128365 | 9/2013 | |
| WO | WO-2013137753 A1 * | 9/2013 | ............ G01F 23/26 |
| WO | WO 2013/151447 | 10/2013 | |
| WO | WO 2014/059405 | 4/2014 | |
| WO | WO 2015/038013 | 3/2015 | |
| WO | WO 2015/183107 | 12/2015 | |
| WO | WO 2017/095241 | 6/2017 | |

OTHER PUBLICATIONS

Office Action in corresponding Chinese Patent Application No. 201711259795.8, dated Feb. 3, 2020, in 9 pages.
Australian Examination Report; dated Mar. 28, 2017; 4 pages.
Chinese Examination Report, dated Feb. 24, 2016; 5 pages.
European Search Report; dated Oct. 13, 2015; 7 pages.
International Search Report; PCT/NZ2013/000059; dated Jun. 30, 2013; 5 pages.
International Search Report in corresponding International Patent Application No. PCT/NZ2015/050068, dated Oct. 29, 2015, in 7 pages.
Japanese Office Action; dated Mar. 1, 2017; 4 pages.
Written Opinion in corresponding International Patent Application No. PCT/NZ2015/050068, dated Dec. 8, 2016, in 7 pages.
Written Opinion of the International Search Authority; PCT/NZ2013/000059; dated Jun. 30, 2013; 4 pages. [301 WO].

(56) References Cited

OTHER PUBLICATIONS

Markus Joos et al., "An ultrasonic sensor for the analysis of binary gas mixtures", Sensors and Actuators B: Chemical, vol. 16, Issues 1-3, Oct. 1993, pp. 413-419.
H. Toda et al., "High-speed gas concentration measurement using ultrasound", Sensors and Actuators A: Physical, vol. 144, Issue 1, May 28, 2008, pp. 1-6.
J.C. Vyas et al., "A non-invasive ultrasonic gas sensor for binary gas mixtures", Sensors and Actuators B: Chemical, vol. 115, Issue 1, May 23, 2006, pp. 28-32.
Written Opinion of the International Search Authority; PCT/NZ2013/000059; dated Jun. 20, 2013; 4 pages.
International Search Report in International Patent Application No. PCT/NZ2015/050068, dated Oct. 29, 2015, in 7 pages.
International Search Report; PCT/NZ2013/000059, dated Jun. 20, 2013, 6 pages.
Extended Search Report for Application No. 13772312.8, dated Oct. 13, 2015, 7 pages.
European Search Report for Application No. 18200021.6 dated Jan. 25, 2019 in 6 pages.
United Kingdom Search and Examination Report for Application No. GB 1816023.4, dated Jan. 28, 2019, 4 pages.
United Kingdom Search and Examination Report for Application No. GB 1821238.1, dated Jan. 29, 2019, 5 pages.
Li Daohua, Sensor Circuit Analysis and Design, Wuhan University Press, Mar. 2000, pp. 203-209.

\* cited by examiner

FLOW PATH SENSING FOR FLOW THERAPY APPARATUS

FIELD OF THE DISCLOSURE

The present disclosure relates to methods and systems for flow path sensing in a flow therapy apparatus for delivering gas to patients.

BACKGROUND

Breathing assistance apparatuses are used in various environments such as hospital, medical facility, residential care, or home environments to deliver a flow of gas to users or patients. A breathing assistance apparatus, or a flow therapy apparatus, may include a valve used to deliver oxygen with the flow of gas, and/or a humidification apparatus to deliver heated and humidified gases. A flow therapy apparatus may allow adjustment and control over characteristics of the gas flow, including flow rate, temperature, gas concentration, humidity, pressure, etc. Sensors, such as heated temperature sensing elements and/or thermistors, are used to measure these properties of the gases.

SUMMARY

The present disclosure describes a flow therapy apparatus where a flow of gases is measured through at least a portion of the flow path. The portion of the flow path can be configured to be continuously curved such that there are no significant angles. The flow path can comprise an entrance, a horizontal portion, and an exit, wherein the entrance and the exit can be positioned in vertically opposed directions, and the horizontal portion is positioned between the entrance and the exit. The horizontal portion can have a smooth curve along the entire length of the horizontal portion. The flow path can further comprise one or more sensors positioned within the flow path and configured to measure the flow of gases through the portion of the flow path. The one or more sensors can comprise one or more of an ultrasonic transducer or gas concentration sensor. The one or more sensors can be configured to sense flow rate and/or oxygen concentration. The one or more sensors can be located in a sensor module.

The flow path can be further configured to have a total flow distance between 50 mm and 150 mm. The flow path can also be further configured to have an average cross-sectional diameter between 10 mm and 20 mm.

The flow path can further comprise a first cross-sectional area at the first end of the flow path; a second cross-sectional area at the second end of the flow path; and a middle cross-sectional area between the first end and second end of the flow path, wherein the middle cross-sectional area can be less than the first cross-sectional area, and wherein the middle cross-sectional area can be less than the second cross-sectional area.

The one or more sensors can be located after a blower. The blower can be a mixer. The one or more sensors can further include a heated temperature sensing element configured to measure flow rate of the gases, and/or temperature, humidity, humidity and temperature, and/or pressure sensors.

Also described is a flow path of gases to prevent unwanted vorticity in the flow of gases that can create anomalies in measuring flow rate. The flow path can be used in conjunction with the ultrasonic sensor system.

The present disclosure describes a flow therapy apparatus that can comprise an inlet port which receives a flow of gases from at least two different gas sources; a blower which receives the flow of gases from the inlet port, where the blower is configured to mix the flow of gases from the different gas sources to produce mixed gases; a gases flow path which receives the mixed gases from the blower and directs the gases flow through a sensor chamber; and one or more sensors, where the sensors are configured to measure one or more properties of the flow of gases flowing through the gases flow path. The one or more sensors can be located after the blower. The blower can be a mixer. The one or more sensors can be located in a sensor module.

The different gas sources can comprise oxygen gas, and the inlet port can comprise a valve configured to deliver a flow of the oxygen gas to the blower. The valve can comprise a proportional valve.

The one or more sensors can comprise two or more ultrasonic transducers. The one or more sensors can also comprise a gas concentration sensor.

The ultrasonic transducers can be configured to determine a gas concentration. The ultrasonic transducers can be configured to determine a flow rate.

The one or more sensors can comprise a heated temperature sensing element configured to measure gases flow rate.

The present disclosure describes a sensing chamber in a flow therapy apparatus that can comprise a flow path configured to accommodate a flow of gases; and one or more sensors configured to measure a property of the flow of gases flowing through the flow path, wherein the sensors can comprise a first ultrasonic transducer positioned at a downstream portion of the flow path, and a second ultrasonic transducer positioned at an upstream portion of the flow path, and wherein the flow path can be configured to have a curved shape between the first and second ultrasonic transducers. The curved shaped can be configured to reduce dead space in the flow of gases The sensors can further comprise one or more temperature sensors configured to measure a temperature of the gases in the flow path.

The temperature sensor can be located in the flow path.

The sensing chamber further comprises a sensing circuit board, wherein a first portion of the sensing circuit board is positioned at least partially within the flow path.

The sensing circuit board can be further configured to effect thermal conduction between the gas flow and the temperature sensor, and impede thermal conduction between a wall of the sensing chamber and the temperature sensor.

The sensing circuit board can further comprise at least a second portion of the sensing circuit board positioned outside the flow path.

The sensing chamber can further comprise a seal dividing the first portion of the sensing circuit board from the second portion of the sensing circuit board. The seal can be a pneumatic seal.

The flow path can be further configured to have a total flow distance between 50 mm and 150 mm.

The flow path can be further configured to have an average cross-sectional diameter between 10 mm and 20 mm.

The flow path can be further configured to have a constant cross-sectional shape along the length of the flow path.

The flow path can comprise a first cross-sectional area at the first end of the flow path; a second cross-sectional area at the second end of the flow path; and a middle cross-sectional area between the first end and second end of the flow path, wherein the middle cross-sectional area can be less than the first cross-sectional area, and wherein the middle cross-sectional area can be less than the second cross-sectional area. The flow path can be configured to be curved throughout between the first and second ultrasonic transducers The present disclosure describes a method for determining a characteristic of gases flowing through a sensing chamber along a gases flow path from a first end of the sensing chamber to a second end of the sensing chamber, where the sensing chamber comprises a first ultrasonic transducer positioned at the first end and a second ultrasonic transducer positioned at the second end, a downstream direction defined along the gases flow path from the first end to the second end, and an upstream direction defined along the gases flow path from the second end to the first end. The method comprises transmitting a downstream acoustic pulse from the first ultrasonic transducer and detecting the downstream acoustic pulse at the second ultrasonic transducer; determining a downstream time of flight based at least in part on the downstream acoustic pulse; transmitting an upstream acoustic pulse from the second ultrasonic transducer and detecting the upstream acoustic pulse at the first ultrasonic transducer; determining an upstream time of flight based at least in part on the upstream acoustic pulse; and determining the characteristic of the gases taking into account dead space between the first ultrasonic transducer and the second ultrasonic transducer.

Determining the characteristic of the gases can comprise determining a gas velocity using the equations:

$$c \approx \frac{D+D_0}{2}\left(\frac{1}{t_1}+\frac{1}{t_2}\right) \text{ and}$$

$$v \approx \frac{(D_0+D)^2}{2D}\left(\frac{1}{t_1}-\frac{1}{t_2}\right),$$

Wherein c represents the speed of sound, D represents the distance between the first ultrasonic transducer and the second ultrasonic transducer where there is gas flow, $D_0$ represents the distance between the first ultrasonic transducer and the second ultrasonic transducer where there is no gas flow, $t_1$ represents the downstream time of flight, and $t_2$ represents the upstream time of flight.

The present disclosure describes a method for determining a characteristic of gases flowing through a sensing chamber along a gases flow path from a first end of the sensing chamber to a second end of the sensing chamber, wherein the sensing chamber comprises a first ultrasonic transducer positioned at the first end and a second ultrasonic transducer positioned at the second end, a downstream direction defined along the gases flow path from the first end to the second end, and an upstream direction defined along the gases flow path from the second end to the first end. The method can comprise transmitting a downstream acoustic pulse from the first ultrasonic transducer and detecting the downstream acoustic pulse at the second ultrasonic transducer. The method can further comprise measuring an entire received ultrasonic waveform. The method can further comprise performing a cross correlation between the received waveform and a reference to produce a time of flight measurement. The reference can be either recorded earlier or defined prior. The reference can be a separate or a previous wave. The cross-correlation can comprise producing a differential time of flight such that a flow rate can be calculated.

The gases can include heliox or carbon dioxide. The cross-correlation can comprise highlighting anomalies during operation.

The present disclosure describes a system for calibrating a measuring module in a flow therapy apparatus. The system can comprise a blower configured to deliver a flow of gases at predetermined operating parameters; a first sensor configured to determine a first value for a gases characteristic; a first memory configured to store the first value; and a control system configured to vary the flow of gases from the blower; and adjust a calibration parameter, based at least in part on the comparison between the first value and a reference value at the predetermined operating parameters. The reference value can be obtained from one or more of a lookup table, user input, or calculated value.

The first sensor can comprise a pair of ultrasonic transducers.

The calibration system can further comprise a valve configured to deliver a flow of a second gas, wherein the control system can be further configured to vary the flow of a second gas. The second gas can comprise oxygen.

The system can further comprise a second sensor configured to determine a second value for the gases characteristic, wherein the control system can be further configured to compare the first value with the second value.

The second sensor can comprise a temperature sensor. The second sensor can comprise a heated temperature sensing element configured to measure gases flow rate. The second sensor can comprise a humidity sensor. The second sensor can further comprise a pressure sensor.

The gases characteristic can be a flow rate. The gases characteristic can be an oxygen concentration or other gas concentration. The gases characteristic can be temperature. The gases characteristic can be humidity. The gases characteristic can be pressure.

The present disclosure describes a sensing chamber in a flow therapy apparatus. The sensing chamber can comprise one or more sensors configured to measure gases properties, the one or more sensors including a first ultrasonic transducer at a downstream portion of a flow path and a second ultrasonic transducer at an upstream portion of the flow path, and a heated temperature sensing element configured to measure gases flow rate. The heated temperature sensing element can provide redundancy of flow measurement, the redundancy comprising fast flow measurement at low flows by the first and second ultrasonic transducers and accurate flow measurement at low flows by the heated temperature sensing element. The redundancy can aid with calibration for a flow rate.

The heated temperature sensing element can adjust a calibration parameter of the ultrasonic transducers. The heated temperature sensing element can adjust readings of the ultrasonic transducers. The adjustment can be a continuous adjustment. The adjustment can be a predetermined amount, rate, or weighted on flow rate or other sensed parameters.

The present disclosure describes a sensing chamber in a flow therapy apparatus. The sensing chamber can comprise one or more sensors, the one or more sensors configured to measure gases properties, the one or more sensors including a first ultrasonic transducer at a downstream portion of a flow path and a second ultrasonic transducer at an upstream portion of the flow path, wherein the one or more sensors can be directly mounted onto the sensing circuit board. The sensing chamber can further comprise ultrasonic circuitry positioned proximate the ultrasonic sensors. The ultrasonic circuitry can be environmentally isolated from the one or more sensors. The chamber can further comprise a seal isolating the ultrasonic circuitry from the one or more sensors. The seal can be a pneumatic seal. At least one of the one or more sensors can be located on a sensing circuit board.

The present disclosure describes a gas delivery system. The system can comprise one or more sensors configured to determine gases properties, a first pressure sensor configured to determine a first absolute pressure, wherein the first absolute pressure can be configured to determine an estimate of ambient pressure; and a second pressure sensor configured to determine a second absolute pressure, wherein the difference between the first and second absolute pressures can determine a calculated differential pressure, and wherein calculation of the gases properties can be adjusted based at least in part on changes in the ambient pressure.

The system can further comprise a blower. The second absolute pressure sensor can be downstream of the blower. A pressure generated by a gases source can be estimated from the calculated differential pressure.

The one or more sensors configured to determine gases properties can comprise ultrasonic sensors. The ambient pressure readings can allow comparison of mass flow rate with volumetric flow rate. The first absolute pressure sensor can be positioned within a housing of the gases delivery system. The second pressure sensor can be positioned within a sensing chamber or sensor module and detects a pressure of the gases flow after the gases have been pressurized by a gases source.

DETAILED DESCRIPTION

Figure 1:
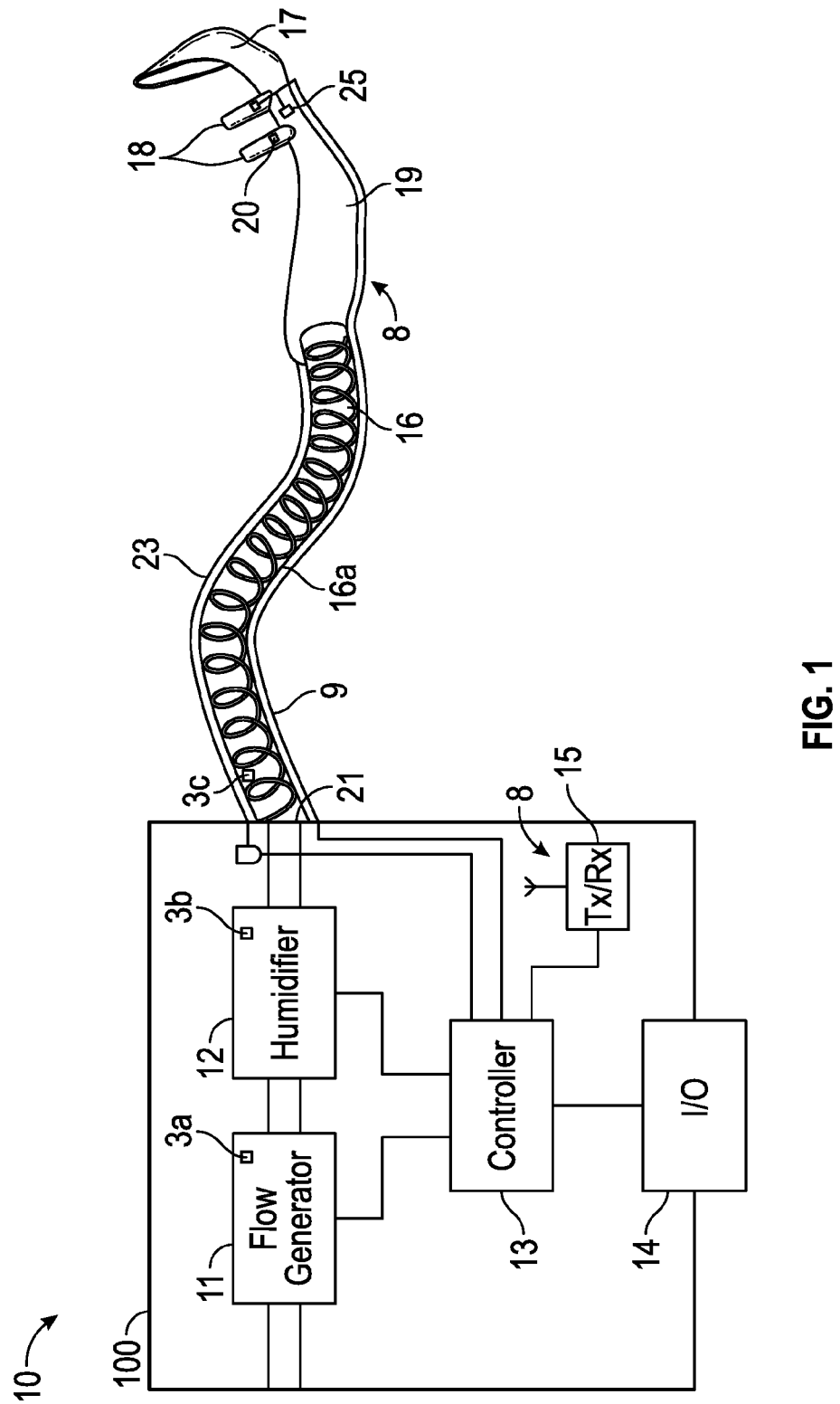
FIG. 1 shows in diagrammatic form a breathing assistance apparatus in the form of a flow therapy apparatus.
Figure 2:
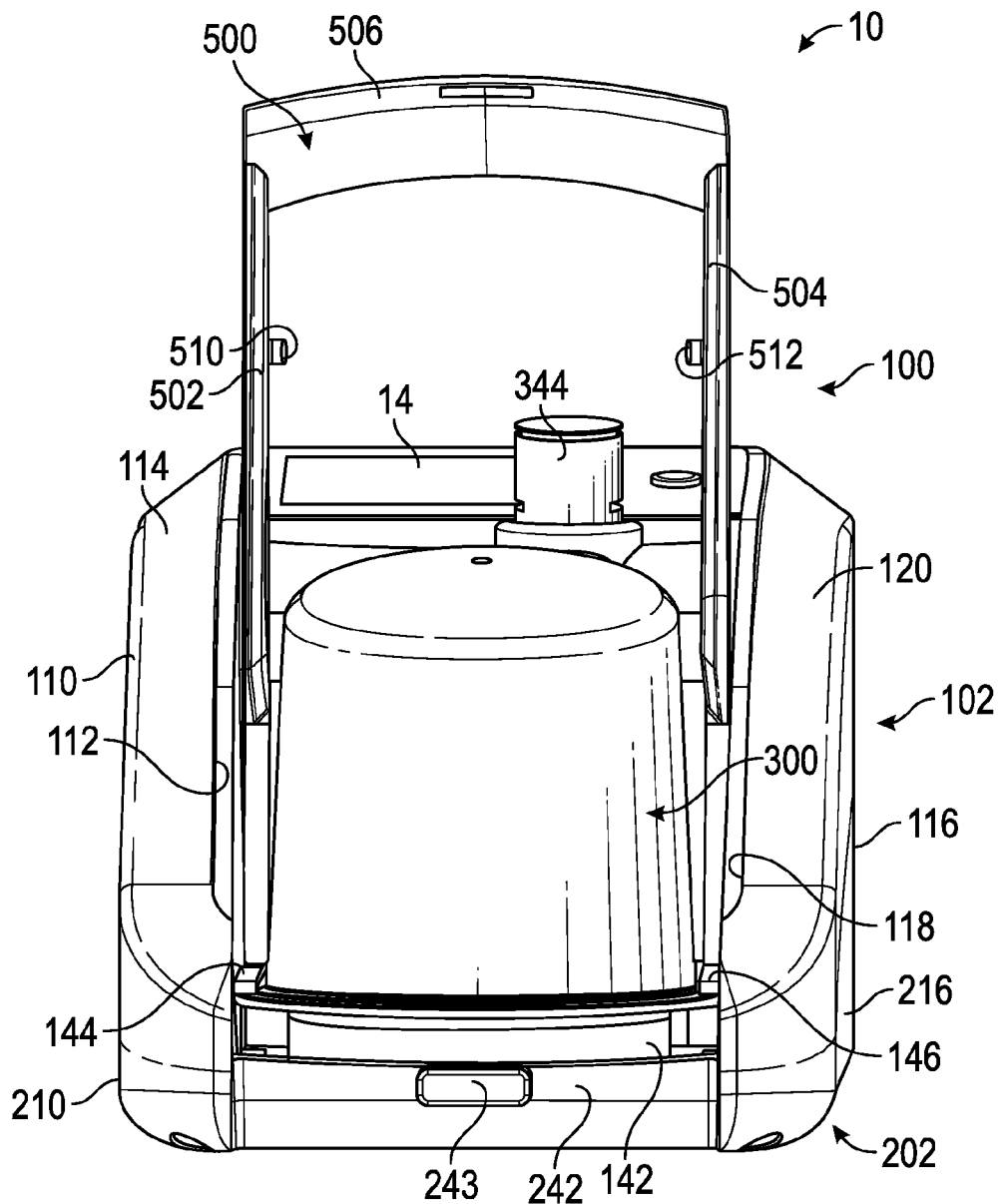
FIG. 2 is a front view of the flow therapy apparatus with a humidifier chamber in position and a raised handle/lever.
Figure 3:
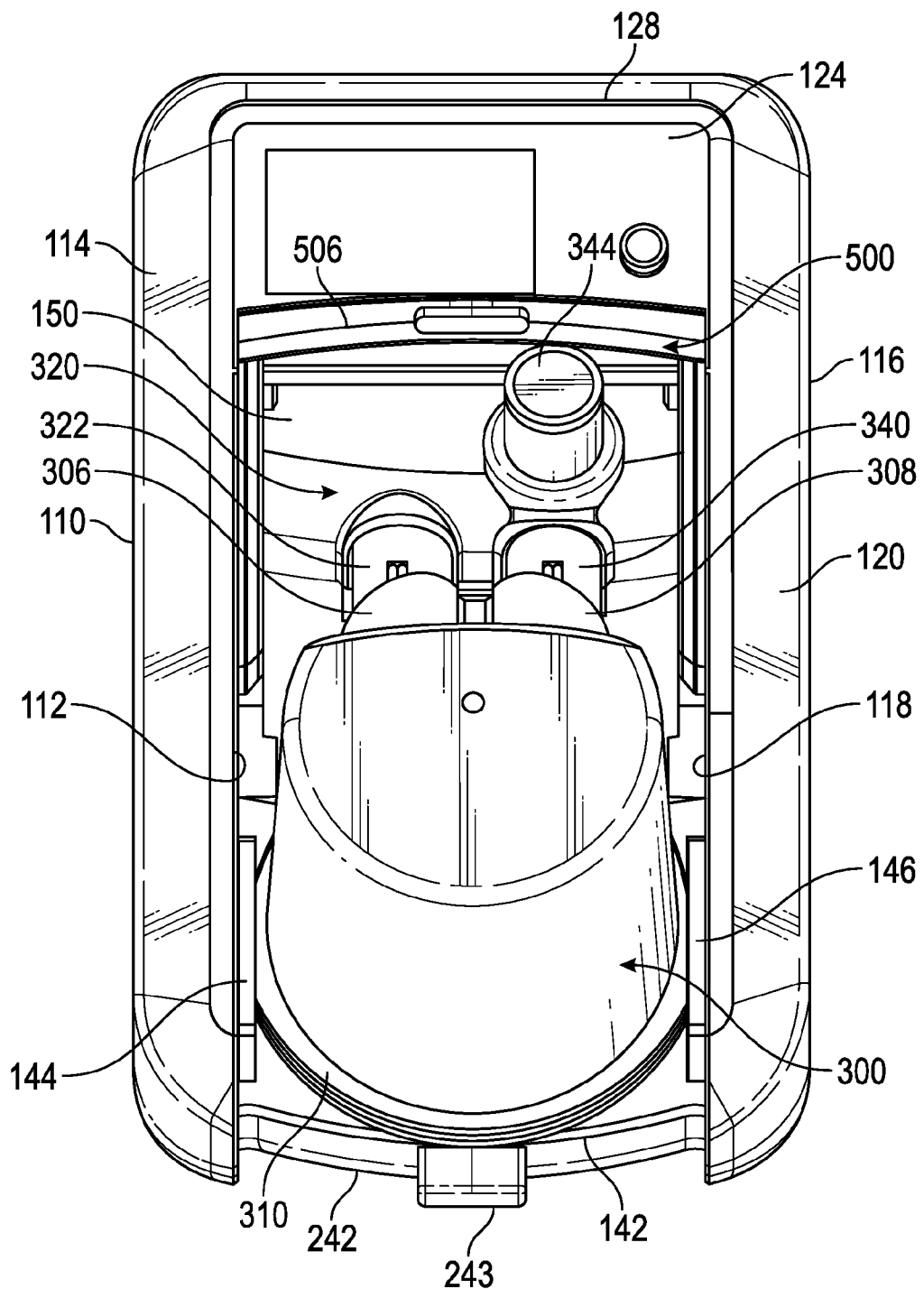
FIG. 3 is a top view corresponding to FIG. 2.
Figure 4:
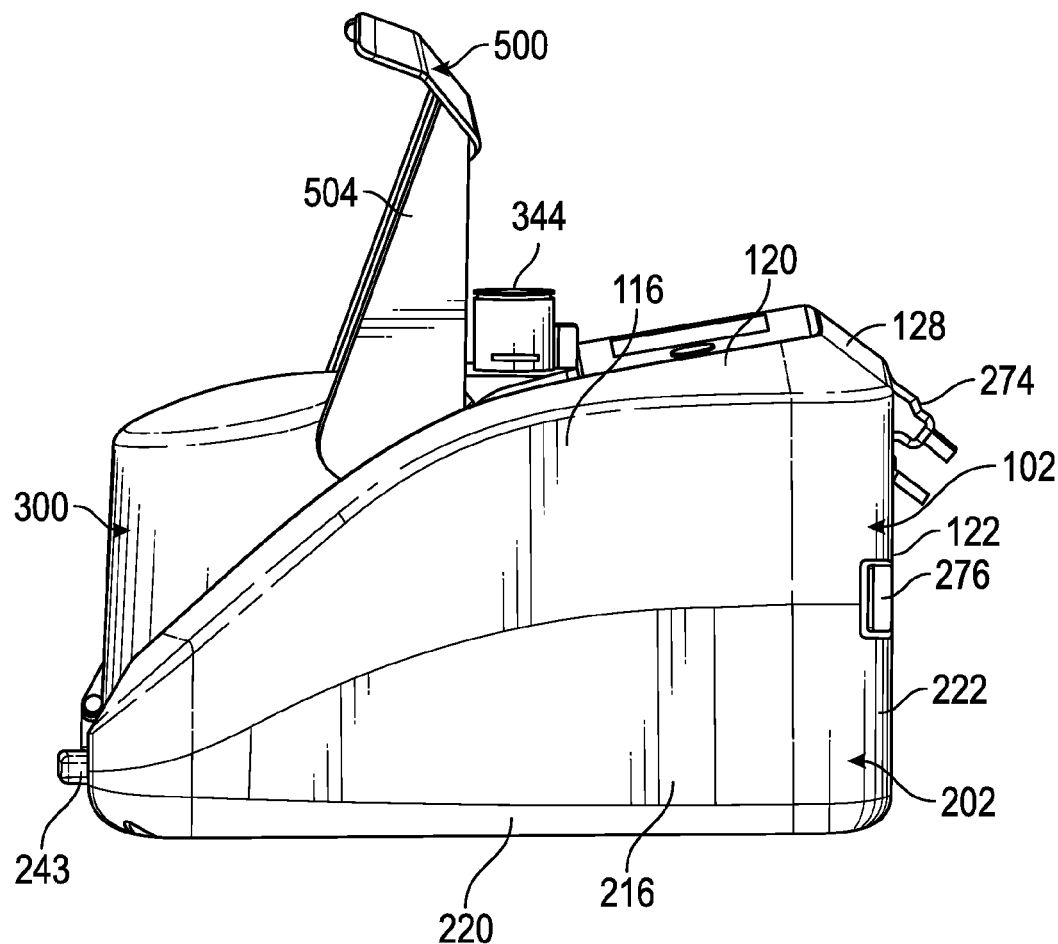
FIG. 4 is a right side view corresponding to FIG. 2.
Figure 5:
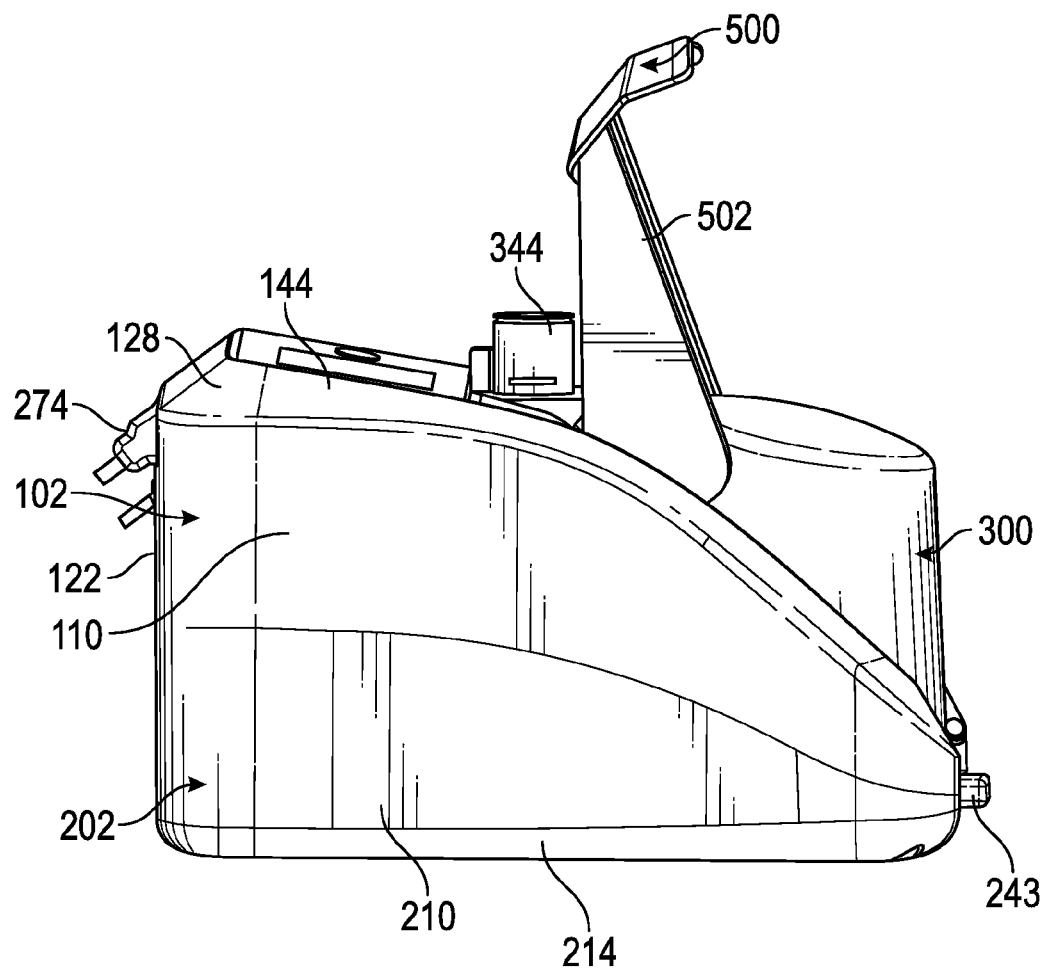
FIG. 5 is a left side view corresponding to FIG. 2.
Figure 6:
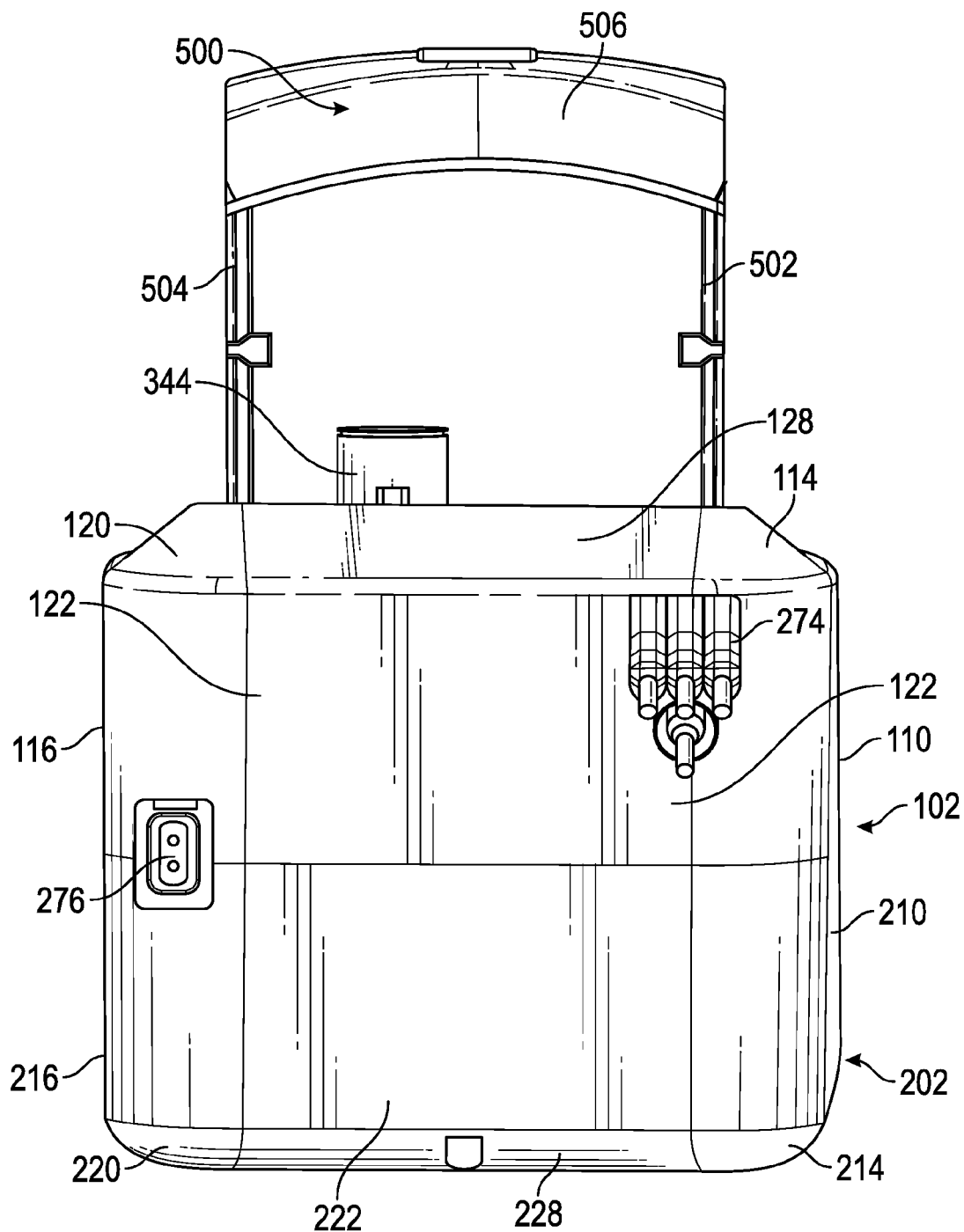
FIG. 6 is a rear view corresponding to FIG. 2.
Figure 7:
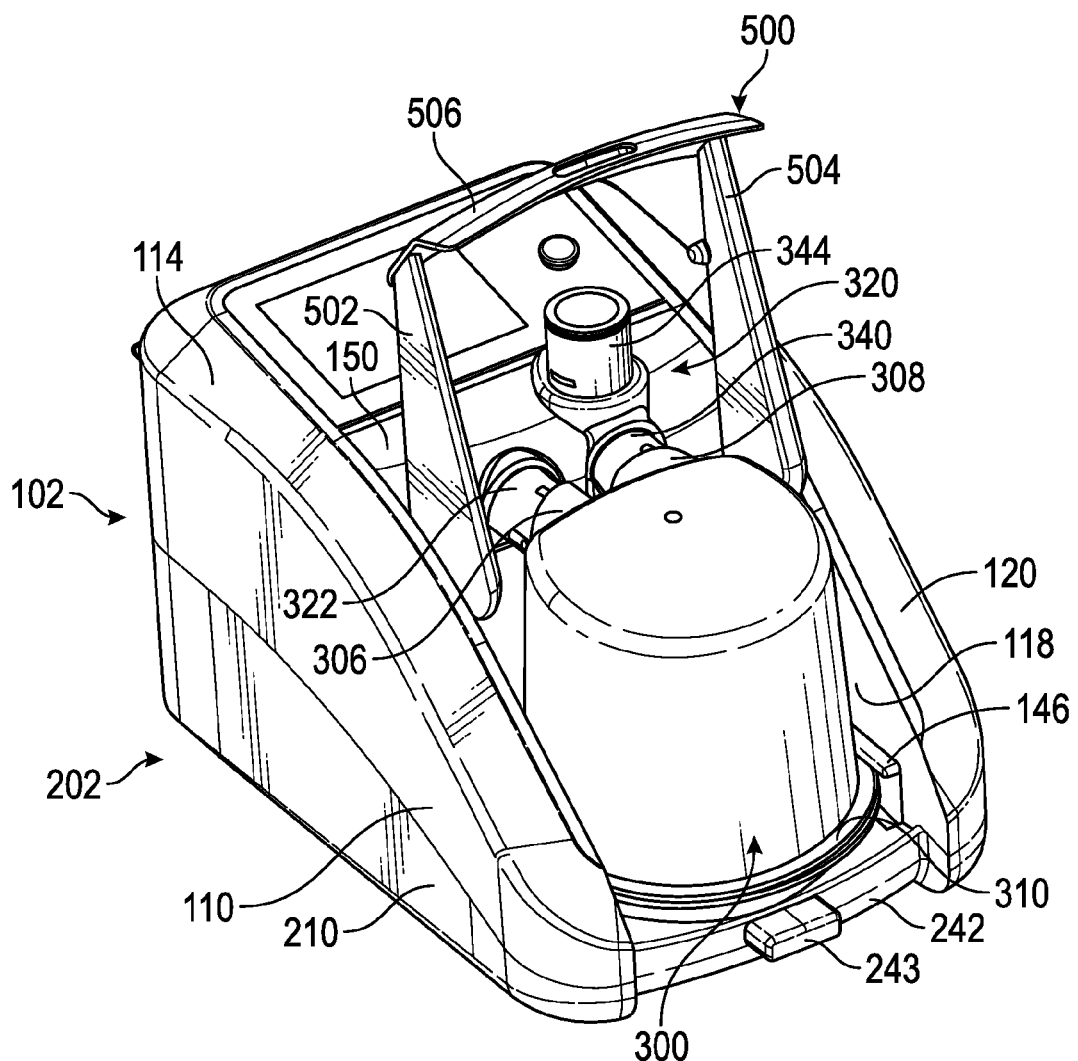
FIG. 7 is a front left perspective view corresponding to FIG. 2.
Figure 8:
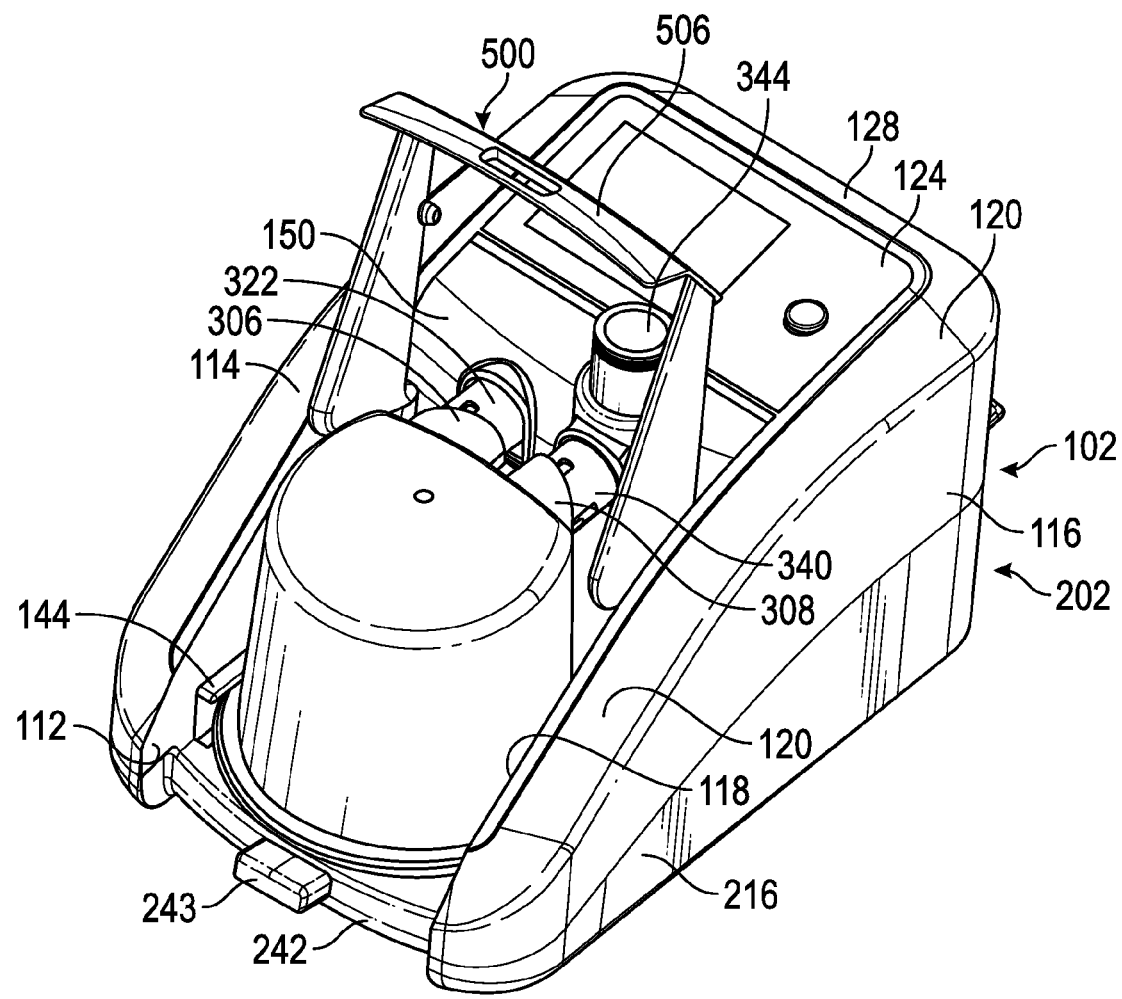
FIG. 8 is a front right perspective view corresponding to FIG. 2.
Figure 9:
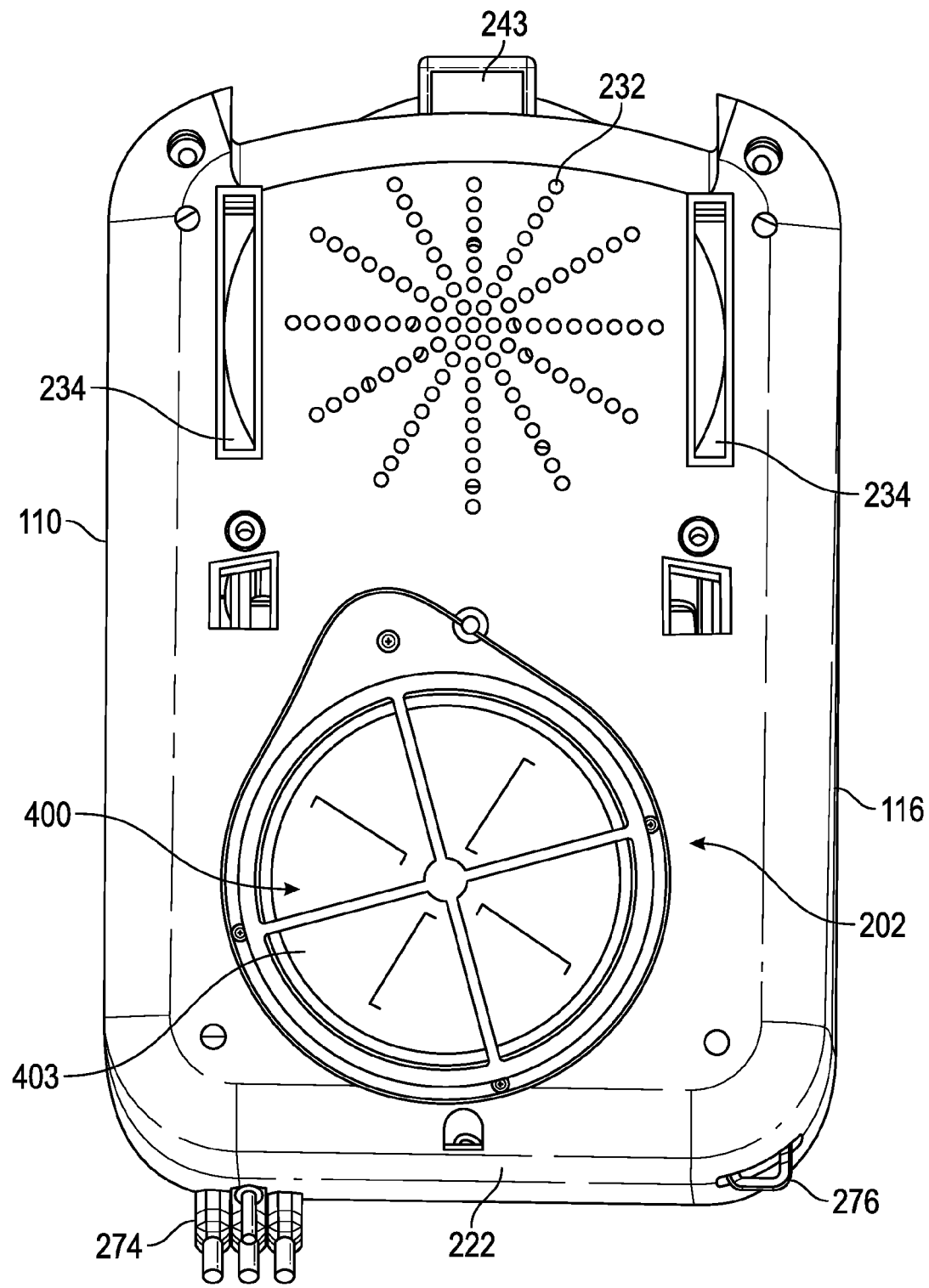
FIG. 9 is a bottom view corresponding to FIG. 2.

A flow therapy apparatus 10 is shown in FIG. 1. In general terms, the apparatus 10 comprises a main housing 100 that contains a flow generator 11 in the form of a motor/impeller arrangement, an optional humidifier 12, a controller 13, and a user I/O interface 14 (comprising, for example, a display and input device(s) such as button(s), a touch screen, a combination of a touch screen and button(s), or the like). The controller 13 is configured or programmed to control the components of the apparatus, including: operating the flow generator 11 to create a flow of gas (gas flow) for delivery to a patient, operating the humidifier 12 (if present) to humidify and/or heat the generated gas flow, receive user input from the user interface 14 for reconfiguration and/or user-defined operation of the apparatus 10, and output information (for example on the display) to the user. The user can be a patient, healthcare professional, or anyone else interested in using the apparatus.

A patient breathing conduit 16 is coupled to a gas flow output 21 in the housing 100 of the flow therapy apparatus 10, and is coupled to a patient interface 17 such as a nasal cannula with a manifold 19 and nasal prongs 18. Additionally, or alternatively, the patient breathing conduit 16 can be coupled to a face mask, or a tracheostomy interface. The gas flow, which may be humidified, that is generated by the flow therapy apparatus 10 is delivered to the patient via the patient conduit 16 through the cannula 17. The patient conduit 16 can have a heater wire 16a to heat gas flow passing through to the patient. The heater wire 16a is under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms the controller 13 controls the flow generator 11 to generate a gas flow of the desired flow rate, controls one or more valves to control the mix of air and oxygen or other alternative gas, and/or controls the humidifier 12 if present to humidify the gas flow and/or heat the gas flow to an appropriate level. The gas flow is directed out through the patient conduit 16 and cannula 17 to the patient. The controller 13 can also control a heating element in the humidifier 12 and/or the heating element 16a in the patient conduit 16 to heat the gas to a desired temperature that achieves a desired level of therapy and/or level of comfort for the patient. The controller 13 can be programmed with or can determine a suitable target temperature of the gas flow.

Operation sensors 3a, 3b, 3c, 20, 25 such as flow, temperature, humidity, and/or pressure sensors can be placed in various locations in the flow therapy apparatus 10 and/or the patient conduit 16 and/or cannula 17. Output from the sensors can be received by the controller 13, to assist it to operate the flow therapy apparatus 10 in a manner that provides suitable therapy. In some configurations, providing suitable therapy includes meeting a patient's inspiratory demand. The apparatus 10 may have a transmitter and/or receiver 15 to enable the controller 13 to receive 8 signals from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

The patient interface may be a non-sealing interface such as a nasal cannula.

Overview including Main Housing Description

Some embodiments of the flow therapy apparatus are described in International Patent Application No. PCT/IB2016/053761, filed Jun. 24, 2016 and entitled "BREATHING ASSISTANCE APPARATUS", the entirety of which is incorporated herein by reference. FIGS. 29 to 33 illustrate some of those embodiments. FIGS. 2 to 17B show another embodiment of the flow therapy apparatus 10 comprising a main housing 100. The main housing 100 has a main housing upper chassis 102 and a main housing lower chassis 202.

The main housing upper chassis 102 has a peripheral wall arrangement 106. The peripheral wall arrangement defines a humidifier or humidification chamber bay 108 for receipt of a removable humidification chamber 300. The removable humidification chamber 300 contains a suitable liquid such as water for humidifying gases that will be delivered to a patient.

In the form shown, the peripheral wall arrangement 106 of the main housing upper chassis 102 comprises a substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 further comprises a substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but can alternatively be substantially horizontal or inwardly angled.

The main housing upper chassis 102 further comprises a substantially vertical rear outer wall 122. An upper part of the main housing upper chassis 102 comprises a forwardly angled surface 124. The surface 124 has a recess 126 for receipt of a display and user interface module 14 shown in more detail in FIGS. 53 and 54. An interconnecting wall 128 extends between and interconnects the upper end of the rear outer wall 122 and the rear edge of the surface 124.

A substantially vertical wall portion 130 extends downwardly from a front end of the surface 124. A substantially horizontal wall portion 132 extends forwardly from a lower end of the wall portion 130 to form a ledge. A substantially vertical wall portion 134 extends downwardly from a front end of the wall portion 132 and terminates at a substantially horizontal floor portion 136 of the humidification chamber bay 108. The left side inner wall 112, right side inner wall 118, wall portion 134, and floor portion 136 together define the humidification chamber bay 108. The floor portion 136 of the humidification chamber bay 108 has a recess 138 to receive a heater arrangement such as a heater plate 140 or other suitable heating element(s) for heating liquid in the humidification chamber 300 for use during a humidification process.

The main housing lower chassis 202 is attachable to the upper chassis 102, either by suitable fasteners or integrated attachment features such as clips for example. The main housing lower chassis 202 comprises a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 further comprises a substantially vertical rear outer wall 222 that is contiguous with the rear outer wall 122 of the upper chassis 102.

The lower housing chassis 202 has a lip 242 that is contiguous with the lip 142 of the upper housing chassis 102, and also forms part of the recess for receiving the handle portion 506 of the lever 500. The lower lip 242 comprises a forwardly directed protrusion 243 that acts as a retainer for the handle portion 506 of the lever 500.

An underside of the lower housing chassis 202 comprises a bottom wall 230. Respective interconnecting walls 214, 220, 228 extend between and interconnect the substantially vertical walls 210, 216, 222 and the bottom wall 230. The bottom wall 230 comprises a grill 232 comprising a plurality of apertures to enable drainage of liquid in case of leakage from the humidification chamber 300 (e.g. from spills). The bottom wall 230 additionally comprises elongated forward-rearward oriented slots 234. The slots 234 additionally enable drainage of liquid in case of leakage from the humidification chamber 300, without the liquid entering the electronics housing. In the illustrated configuration, the heater plate 140 is not supported by outer portions of the bottom wall 230, and so the slots 234 can be wide and elongate relative to the apertures of the grill 232 to maximize the drainage of liquid.

Figure 17A:
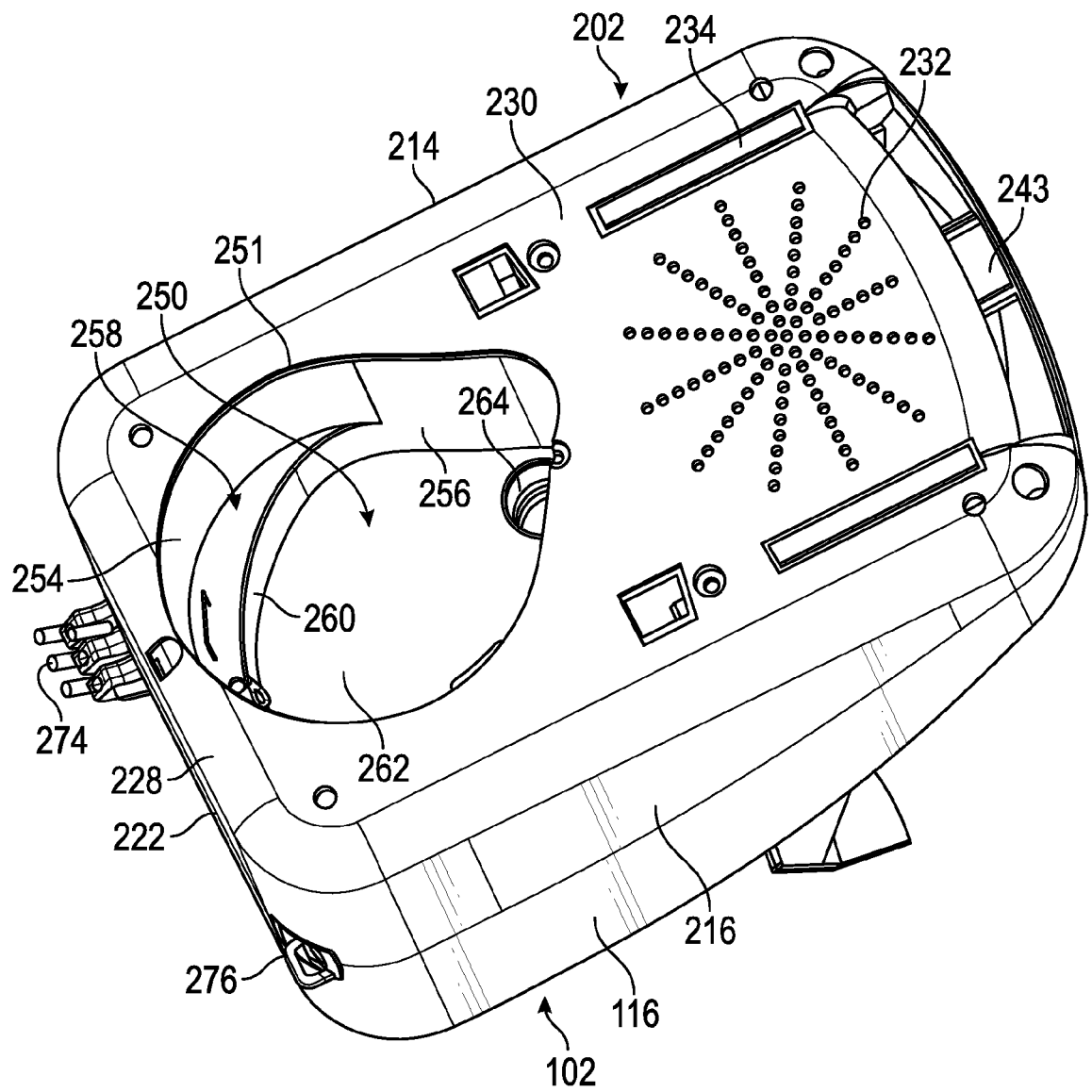
FIG. 17A is a first underside perspective view of the main housing of the flow therapy apparatus showing a recess inside the housing for the motor and/or sensor module sub-assembly.
Figure 17B:
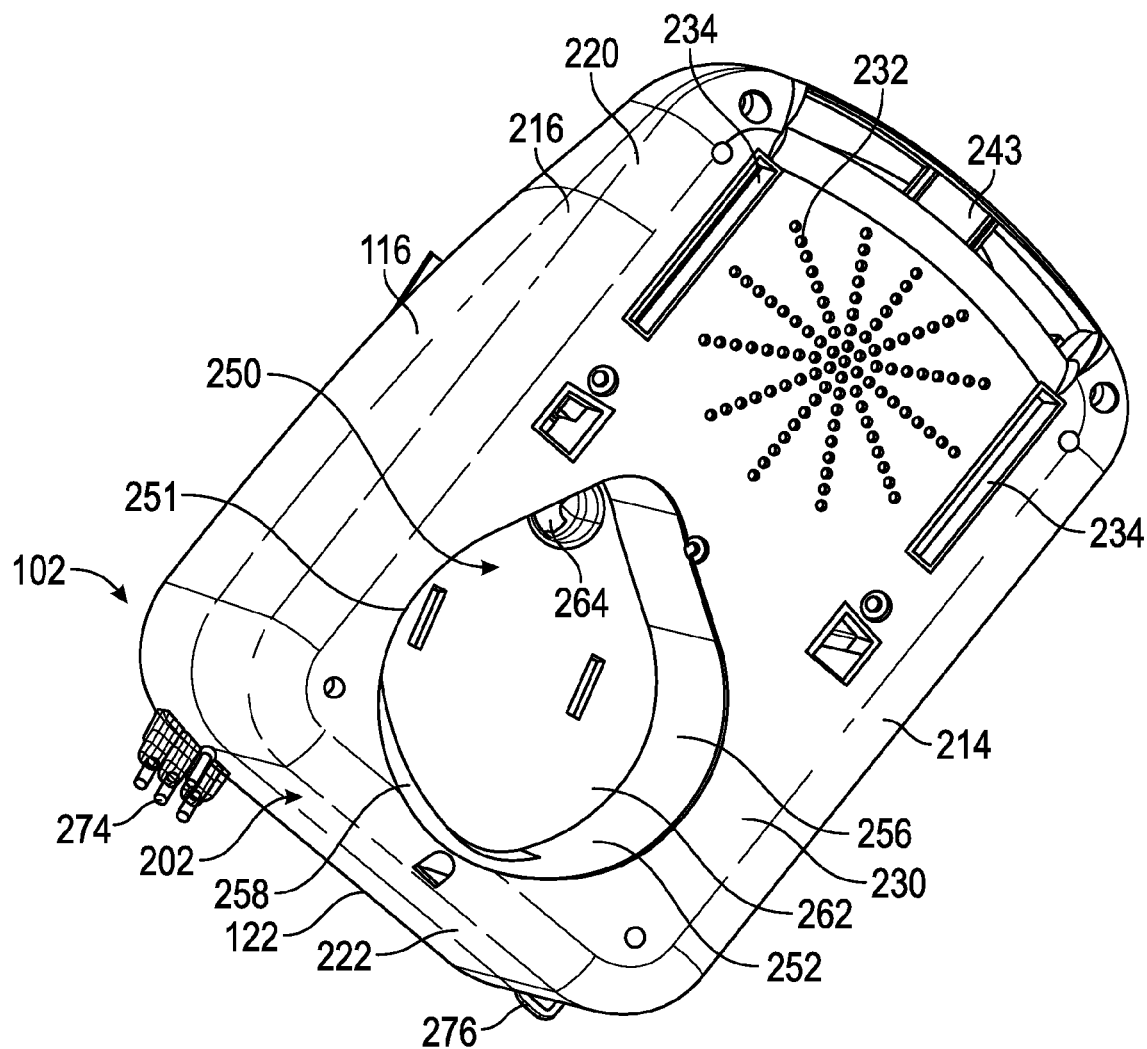
FIG. 17B is a second underside perspective view of the main housing of the flow therapy apparatus showing the recess for the motor and/or sensor module sub-assembly.

As shown in FIGS. 17a to 17b, the lower chassis 202 has a motor recess 250 for receipt of a removable motor and/or sensor module. A recess opening 251 is provided in the bottom wall 230 adjacent a rear edge thereof, for receipt of a removable motor/sensor module. A continuous, gas impermeable, unbroken peripheral wall 252 is integrally formed with the bottom wall 230 of the lower chassis 202 and extends upwardly from the periphery of the opening 251. A rearward portion 254 of the peripheral wall 252 has a first height, and a forward portion 256 of the peripheral wall 252 has a second height that is greater than the first height. The rearward portion 254 of the peripheral wall 252 terminates at a substantially horizontal step 258, which in turn terminates at an upper auxiliary rearward portion 260 of the peripheral wall 252. The forward portion 256 and upper auxiliary rearward portion 260 of the peripheral wall 252 terminate at a ceiling 262. All of the walls and the ceiling 262 are continuous, gas impermeable, and unbroken other than the gas flow passage. Therefore, the entire motor recess 250 is gas impermeable and unbroken, other than the gas flow passage.

In an alternative configuration, the motor recess comprising items 252, 254, 256, 258, 260, 264 may be separately formed from the lower chassis 202. The motor assembly including the recess may be insertable into the recess opening 251 and attachable to the lower chassis 202. Upon insertion of the motor assembly and recess into the lower chassis 202, the gas flow passage tube 264 will extend through the downward extension tube 133 and be sealed by the soft seal.

The apparatus 10 comprises a connection manifold arrangement 320 for fluid coupling of the humidification chamber 300 to the apparatus 10. The humidification chamber 300 can be fluidly coupled to the apparatus 10 in a linear slide-on motion in a rearward direction of the humidification chamber 300 into the chamber bay 108, from a position at the front of the housing 100 in a direction toward the rear of the housing 100. The connection manifold arrangement 320 comprises a manifold gases outlet port 322 that is in fluid communication, via a fixed L shaped elbow 324, with the gas flow passage from the motor/impeller unit 402.

The connection manifold arrangement 320 further comprises a manifold gases inlet port 340 (humidified gases return) that is embodied in a removable elbow. The removable elbow is L-shaped, and further comprises a patient outlet port 344 for coupling to the patient conduit 16 to deliver gases to the patient interface 17. The manifold gases outlet port 322, manifold gases inlet port 340, and patient outlet port 344 each comprise soft seals such as O-ring seals or T-seals to provide a sealed gases passageway between the apparatus 10, the humidification chamber 300, and the patient conduit 16.

The humidification chamber gases inlet port 306 is complementary with the connection manifold gases outlet port 322, and the humidification chamber gases outlet port 308 is complementary with the connection manifold gases inlet port 340. The axes of those ports are preferably parallel to enable the humidification chamber 300 to be inserted into the chamber bay 108 in a linear movement.

Figure 10:
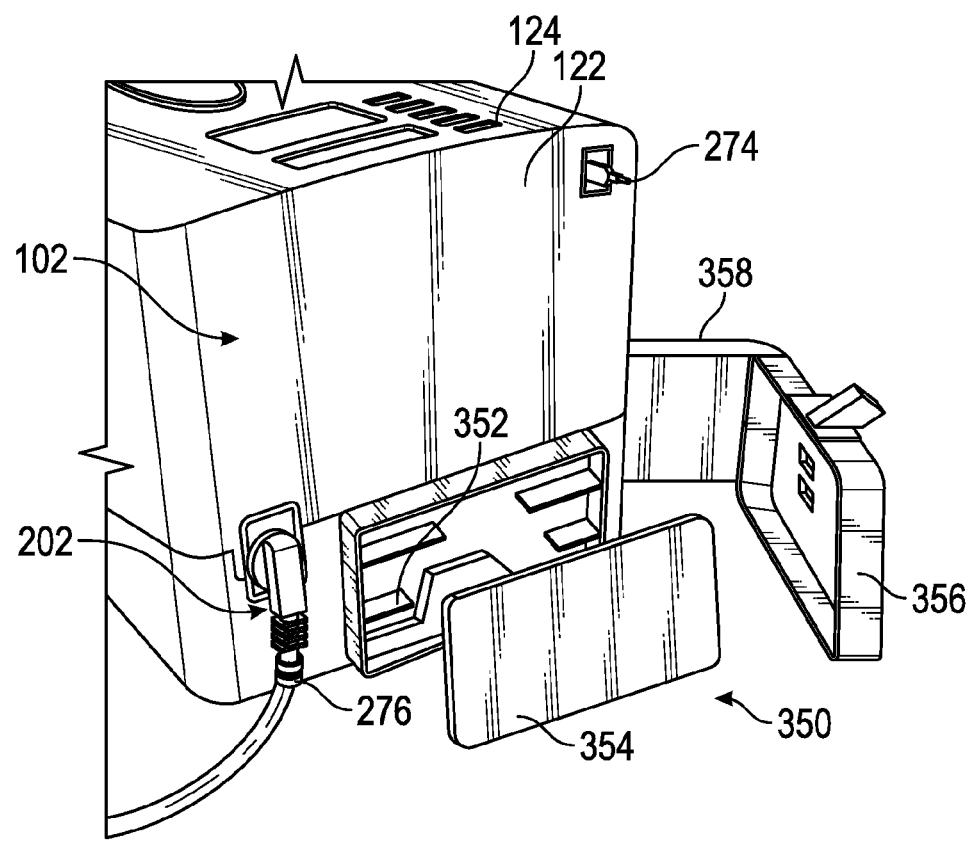
FIG. 10 shows a first configuration of an air and oxygen inlet arrangement of the flow therapy apparatus.
Figure 11:
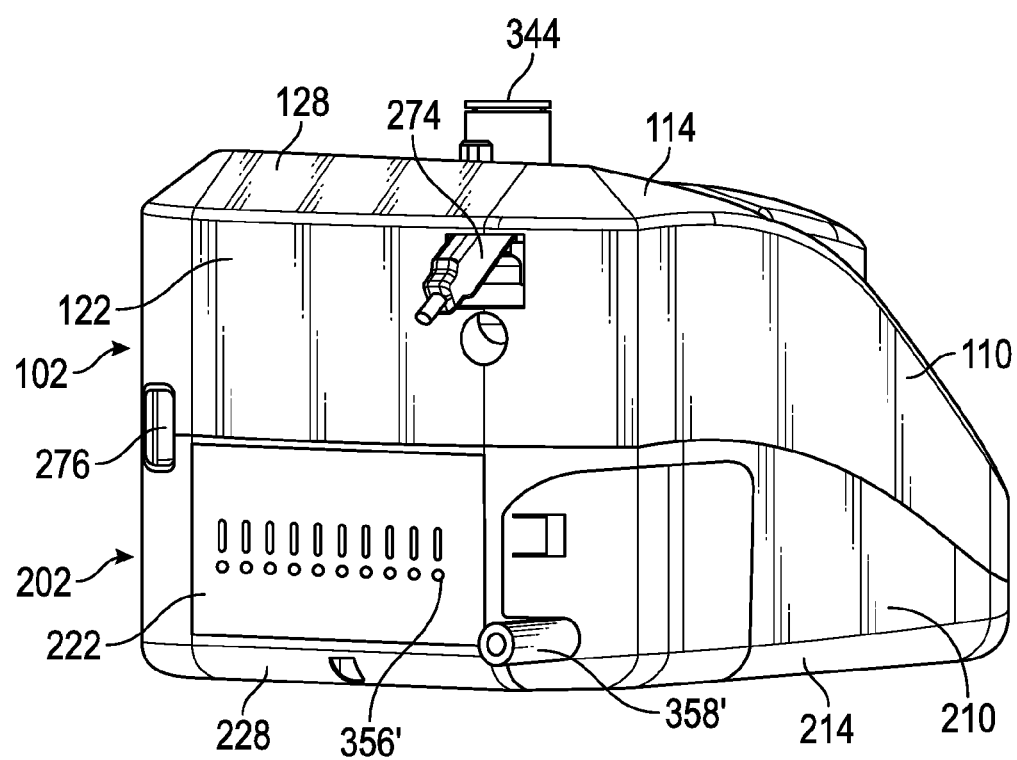
FIG. 11 shows a second configuration of an air and oxygen inlet arrangement of the flow therapy apparatus.
Figure 12:
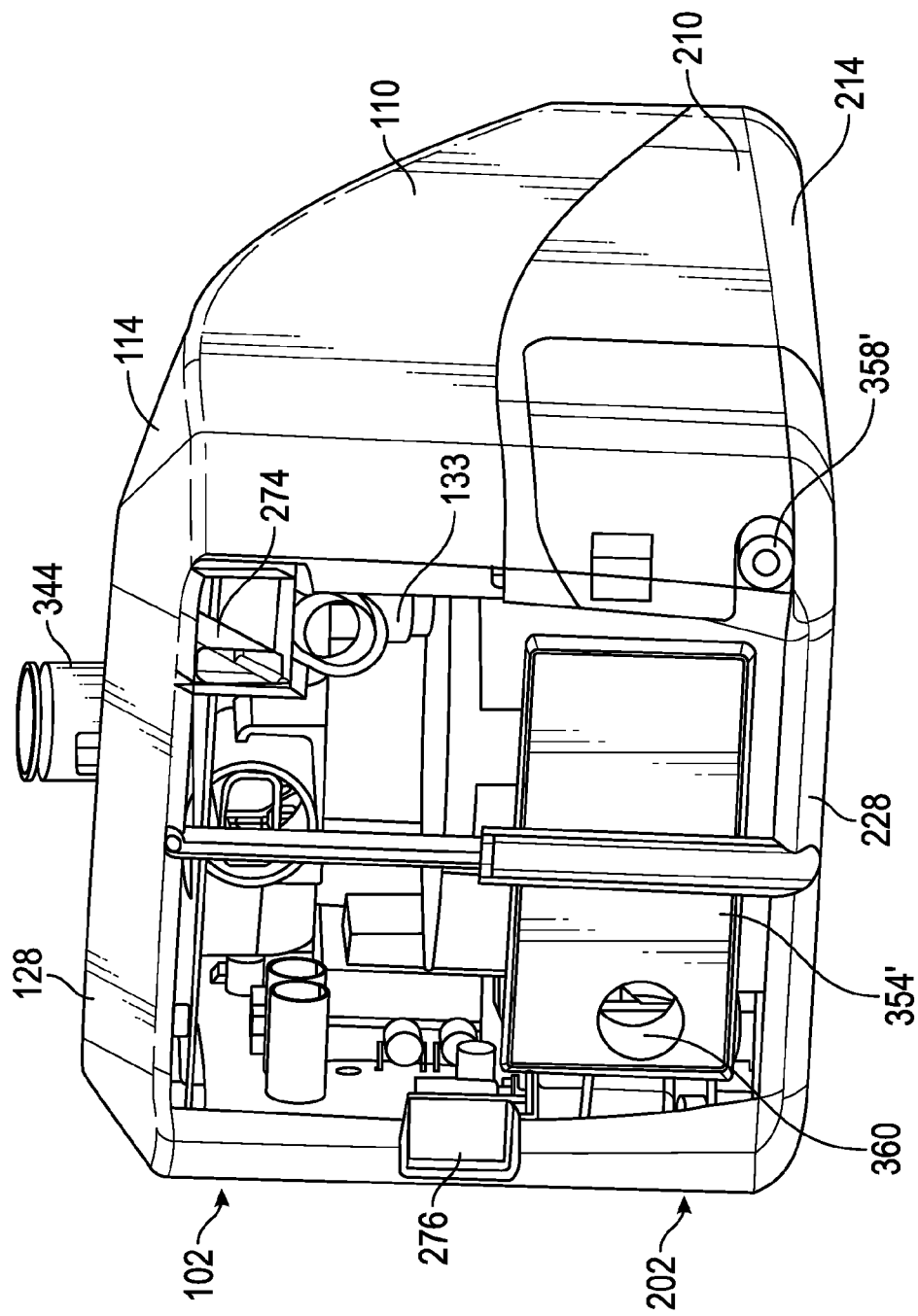
FIG. 12 is a transverse sectional view showing further detail of the air and oxygen inlet arrangement of FIG. 11.
Figure 13:
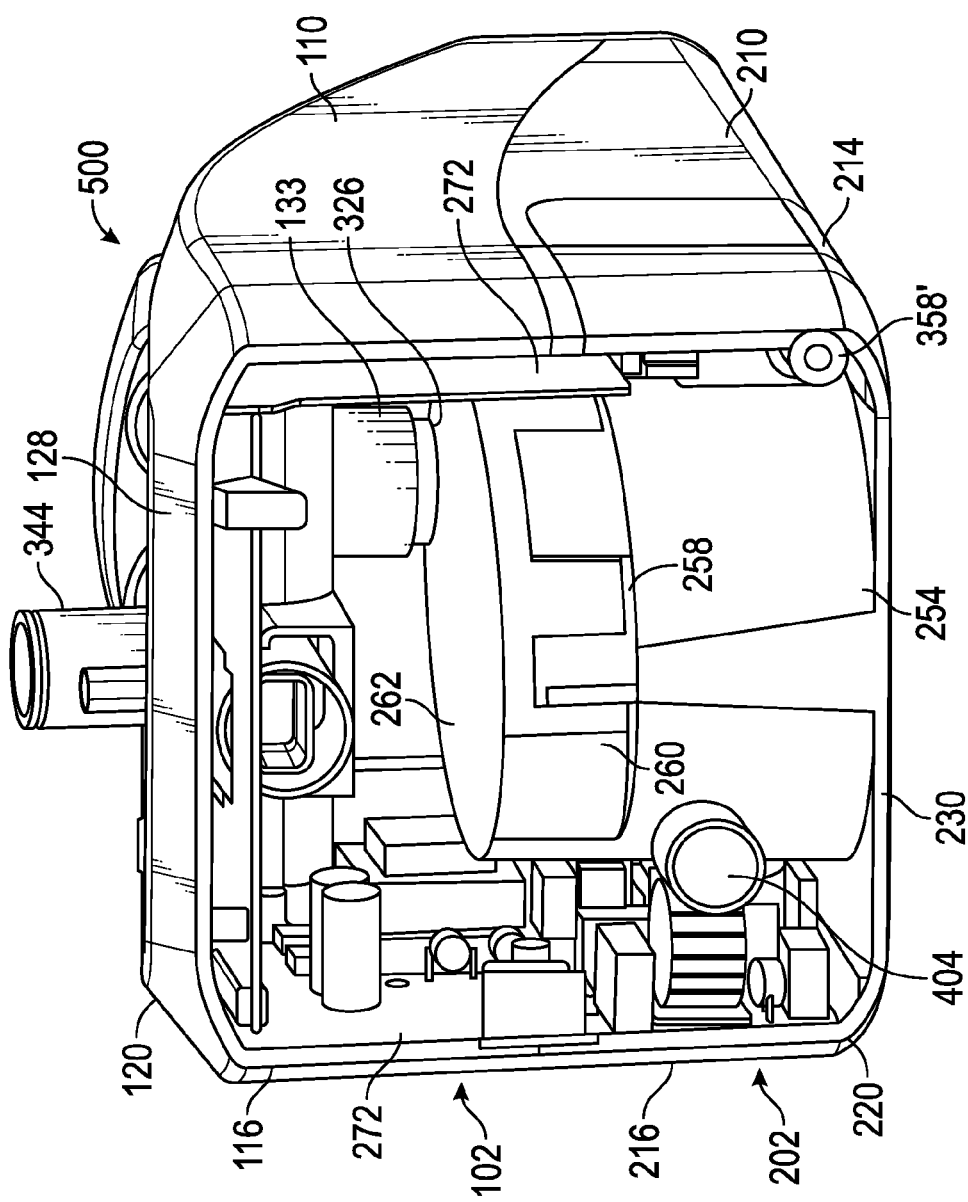
FIG. 13 is another transverse sectional view showing further detail of the air and oxygen inlet arrangement of FIG. 11.
Figure 14:
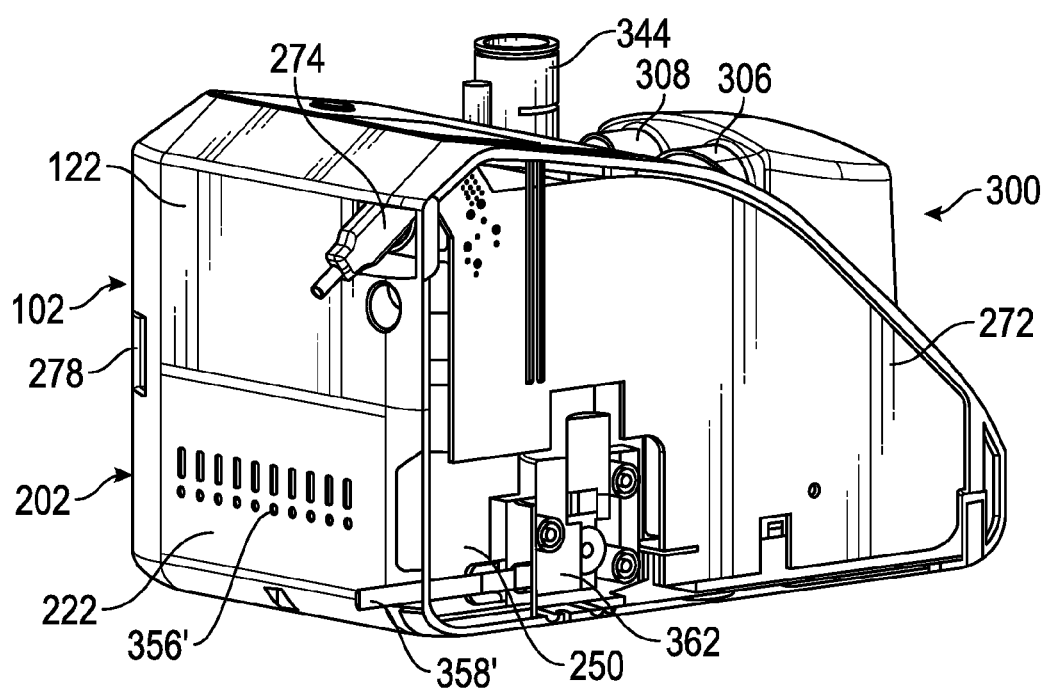
FIG. 14 is a longitudinal sectional view showing further detail of the air and oxygen inlet arrangement of FIG. 11.
Figure 15:
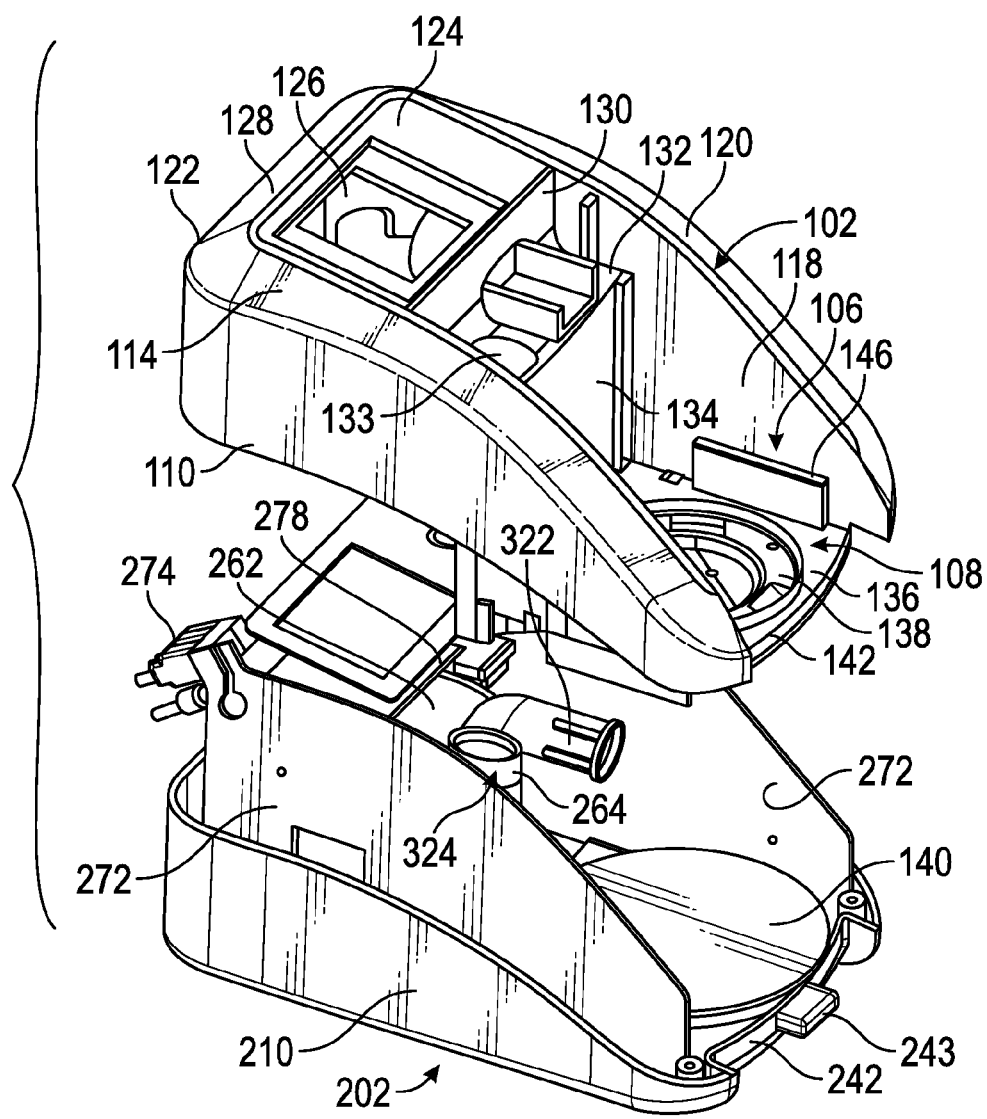
FIG. 15 is an exploded view of upper and lower chassis components of a main housing of the flow therapy apparatus.
Figure 16:
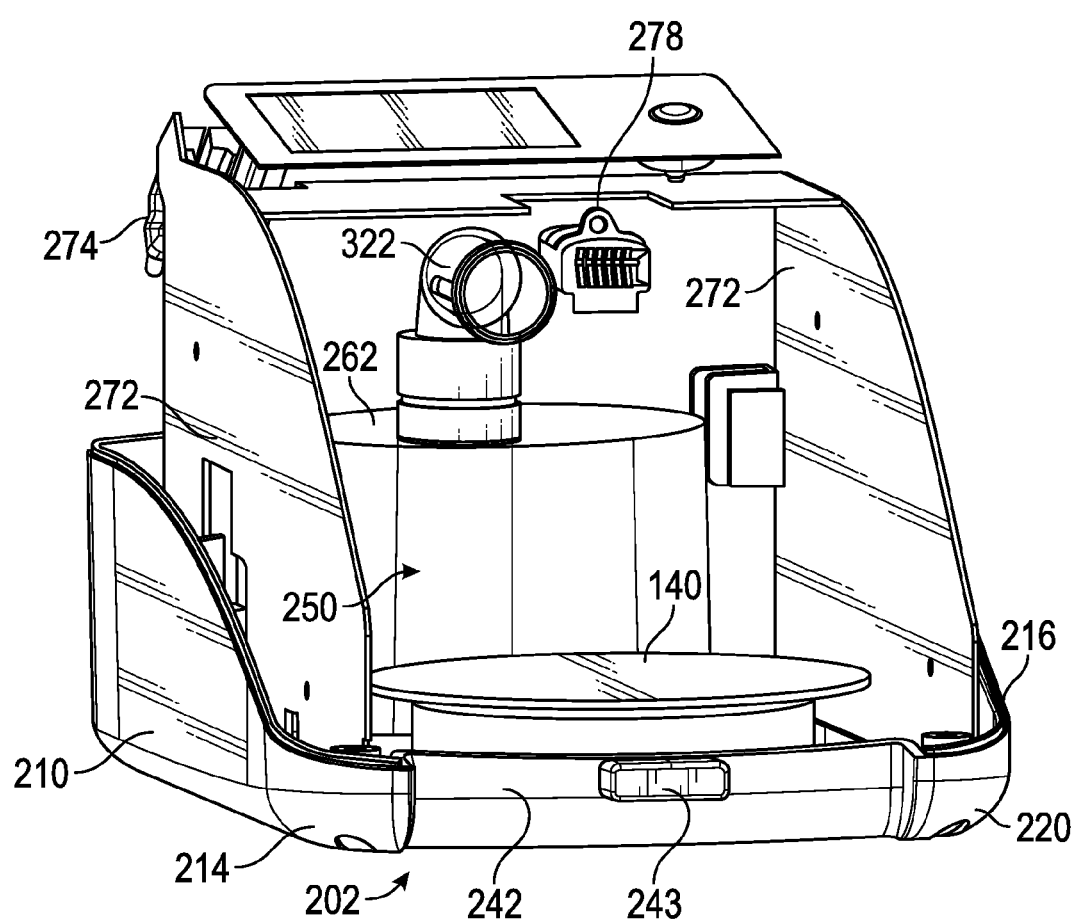
FIG. 16 is a front left side perspective view of the lower chassis of the main housing showing a housing for receipt of a motor and/or sensor module sub-assembly.

The apparatus 10 has air and oxygen (or alternative auxiliary gas) inlets in fluid communication with the motor to enable the motor to deliver air, oxygen, or a suitable mixture thereof to the humidification chamber 300 and thereby to the patient. As shown in FIG. 10 the apparatus 10 may have a combined air/oxygen (or alternative auxiliary gas) inlet arrangement 350. This arrangement comprises a combined air/oxygen port 352 into the housing 100, a filter 354, and a cover 356 with a laterally extending oxygen tube 358 that is in fluid communication with an oxygen source. The port 352 is fluidly coupled with the motor 402. For example, the port 352 may be coupled with the motor and/or sensor module 400 via a gas flow passage between the port 352 and an inlet aperture or port in the motor and/or sensor module 400, which in turn would lead to the motor. This arrangement may be of the type described in U.S. patent application Ser. No. 14/286,590, filed May 23, 2014, published as US 2014/0345615, and the contents of that specification are incorporated herein in their entirety by way of reference.

Alternatively, the apparatus 10 may have the arrangement shown in FIGS. 11 to 14 to enable the motor to deliver air, oxygen (or alternative auxiliary gas), or a suitable mixture thereof to the humidification chamber 300 and thereby to the patient. This arrangement comprises an air inlet 356' in the rear wall 222 of the lower chassis 202 of the housing 100. The air inlet 356' comprises a rigid plate with a suitable grill arrangement of apertures and/or slots. Sound dampening foam may be provided adjacent the plate on the interior side of the plate. An air filter box 354' is positioned adjacent the air inlet 356' internally in the main housing 100, and comprises an air outlet port 360 to deliver filtered air to the motor via an air inlet port 404 in the motor and/or sensor module 400. The air filter box 354' may comprise a filter configured to remove particulates (e.g. dust) and/or pathogens (e.g. viruses or bacteria) from the gas flow. A soft seal such as an O-ring seal will be provided between the air outlet port 360 and air inlet port 404 to seal between the components. The apparatus 10 comprises a separate oxygen inlet port 358' positioned adjacent one side of the housing 100 at a rear end thereof, the oxygen port 358' for receipt of oxygen from an oxygen source such as a tank or source of piped oxygen. The oxygen inlet port 358' is in fluid communication with a valve 362. The valve 362 can suitably be a solenoid valve that enables the control of the amount of oxygen that is added to the gas flow that is delivered to the humidification chamber 300. It should be understood that in alternative configurations the oxygen port 358' and valve 362 may be used with other auxiliary gases to control the addition of other auxiliary gases to the gas flow. The other auxiliary gases may comprise any one or more of a number of gases useful for gas therapy, including but not limited to heliox and nitric oxide. More details regarding the valve and filter are described in U.S. Provisional Application No. 62/409,543, filed Oct. 18, 2016 and entitled "VALVE MODULE AND FILTER," the entirety of which is incorporated herein by reference.

As shown in FIGS. 13 to 16, the lower housing chassis 202 carries suitable electronics boards 272. The electronics boards can be positioned adjacent respective outer side walls 210, 216 of the lower housing chassis 202. The electronics boards 272 can contain, or can be in electrical communication with, suitable electrical or electronics components such as but not limited to microprocessors, capacitors, resistors, diodes, operational amplifiers, comparators, and switches. Sensors may be used. Components of the electronics boards 272 (such as but not limited to one or more microprocessors) can act as the controller 13 of the apparatus.

One or both of the electronics boards 272 can be in electrical communication with the electrical components of the apparatus 10, including the display unit and user interface 14, motor, valve 362, and the heater plate 140 to operate the motor to provide the desired flow rate of gas, operate the humidifier 12 to humidify and heat the gas flow to an appropriate level, and supply appropriate quantities of oxygen (or in alternative configurations quantities of an alternative auxiliary gas) to the gas flow.

The electronics boards 272 can be in electrical communication with a connector arrangement 274 projecting from the rear wall 122 of the upper housing chassis 102. The connector arrangement 274 may be coupled to a nurse alarm, pulse oximetry port, and/or other suitable accessories. The electronics boards 272 can also be in electrical communication with an electrical connector 276 that is also provided in the rear wall 122 of the upper housing chassis 102 to provide mains or battery power to the components of the apparatus 10.

As mentioned above, operation sensors, such as flow, temperature, humidity, and/or pressure sensors can be placed in various locations in the flow therapy apparatus 10 and/or the patient conduit 16 and/or cannula 17. The electronics boards 272 can be in electrical communication with those sensors. Output from the sensors can be received by the controller 13, to assist the controller 13 to operate the flow therapy apparatus 10 in a manner that provides optimal therapy, including meeting inspiratory demand.

As outlined above, the electronics boards 272 and other electrical and electronic components can be pneumatically isolated from the gas flow path, to improve safety and eliminate fire risk. The sealing also prevents water ingress.

Control System

Figure 18:
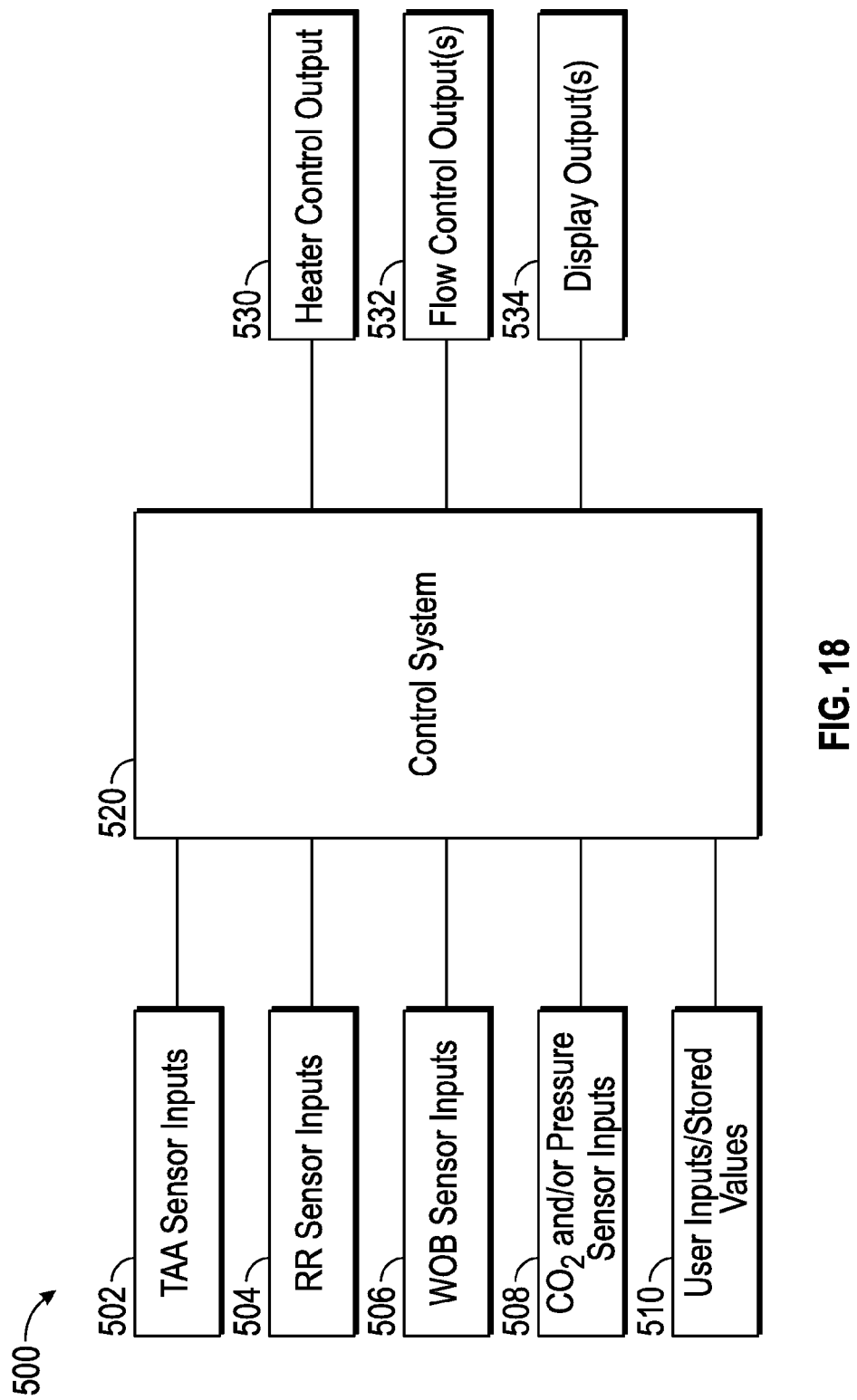
FIG. 18 illustrates a block diagram of a control system interacting with and/or providing control and direction to components of a respiratory assistance system according to an embodiment of the present disclosure.

FIG. 18 illustrates a block diagram of an embodiment of a control system 520 that can detect patient conditions and control operation of the flow therapy apparatus including the gas source. In an embodiment, the control system 520 manages flow rate 532 of the gas flowing through the flow therapy apparatus as it is delivered to a patient. The control system 520 can increase or decrease the flow rate by controlling a motor speed of the blower or a valve in a blender. The control system 520 can automatically determine a set value or a personalized value of the flow rate for a particular patient as discussed below. In some embodiments, the flow rate can be optimized by the control system 520 to improve patient comfort and therapy.

The control system 520 can also generate audio and/or visual outputs 534. For example, the flow therapy apparatus can include a display 630 (see FIG. 19) which may further include a speaker. The display 630 can indicate to the physicians any warnings or alarms generated by the control system 520. The display 630 can also indicate control parameters that can be adjusted by the physicians. For example, the control system 520 can automatically recommend a flow rate for a particular patient. The control system 520 can also generate recovery state of the patient and send it to the display.

In some embodiments, the control system 520 can change a temperature set point 530 of one of the heating elements, to control the output conditions of the gas delivered to the patient. The control system 520 can also change the operation or duty cycle of the heating elements.

The control system 520 can determine outputs 530-534 based on one or more received inputs 502-510. The inputs 502-508 can correspond to sensor measurements received automatically by the controller 600. In the illustrated embodiment, the control system 520 receives sensor inputs corresponding to thoraco-abdominal asynchrony (TAA) sensor inputs 502, respiration rate sensor inputs 504, work of breathing sensor inputs 506, and $CO_2$ sensor inputs 508 and/or other sensors (pressure sensor, ambient sensor, pulse oximeter sensor) in the flow therapy apparatus described above. In an embodiment, the control system 520 can also receive inputs from a user or stored values in a memory 624. The control system 520 can dynamically adjust flow rate 532 for a patient over the time of their therapy. In an embodiment, the control system 520 can continuously detect system parameters and patient parameters.

Controller

Figure 19:
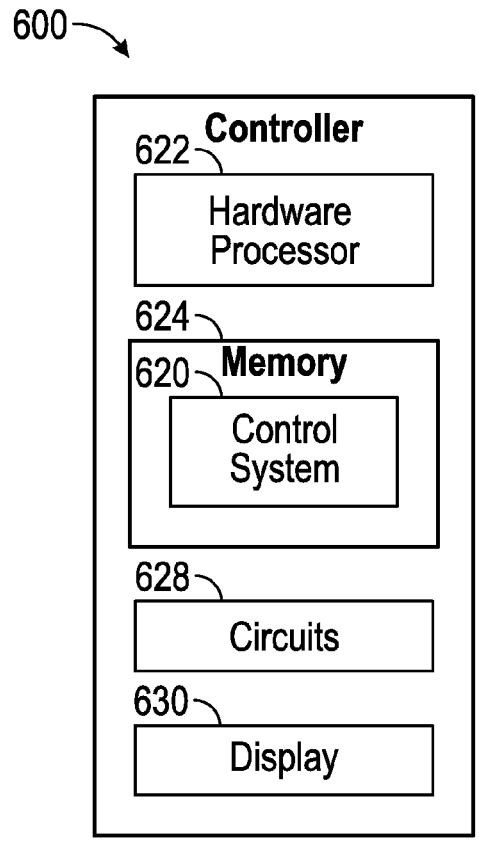
FIG. 19 illustrates a block diagram of a controller according to an embodiment of the present disclosure.

The control system 520 can include programming instructions for detection of input conditions and control of output conditions. The programming instructions can be stored in a memory 624 of the controller 600 as shown in FIG. 19. In some embodiments, the programming instructions correspond to the methods, processes and functions described herein. The control system 520 can be executed by one or more hardware processors 622 of the controller 600. The programming instructions can be implemented in C, C++, JAVA, or any other suitable programming languages. In some embodiments, some or all of the portions of the control system 520 can be implemented in application specific circuitry 628 such as ASICs and FPGAs.

As illustrated in FIG. 18, the control system 520 can receive inputs from multiple components of the flow therapy apparatus. Not all of the inputs 502-510 shown in FIG. 18 may be present. The inputs 502 to 510 and the outputs 530 to 534 may not necessarily be present in all embodiments. For example, in some embodiments, the control system 520 may only receive the work of breathing (WOB) and/or respiratory rate sensor input 506 and generate a flow control measurement 532. Depending on the configuration, some of the components corresponding to the inputs may not be included in the flow therapy apparatus. Lack of input itself can be used by the control system 520 to determine the input or system conditions.

FIG. 19 illustrates a block diagram of an embodiment of a controller 600. The controller can include a hardware processor 622 that can execute the instructions stored in a memory 626. In an embodiment, the control system 520 is stored as programming instructions in the memory 626. The controller can also include circuits 628 for receiving sensor signals. The controller can further include a display 630 for transmitting status of the patient and the respiratory assistance system. The display 630 can also show warnings. The controller can also receive user inputs via the user interface such as display 630. The user interface may alternatively or additionally comprise buttons or a dial. The user interface may alternatively or additionally comprise a touch screen.

Motor and/or Sensor Module

Figure 20:
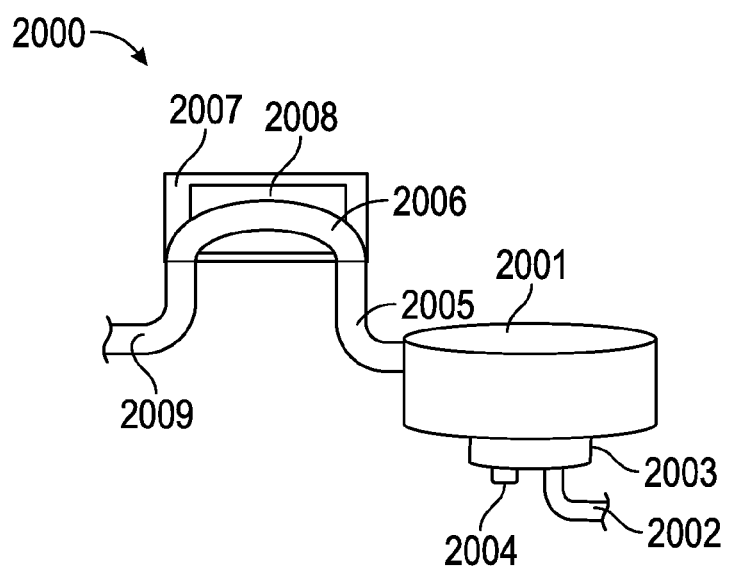
FIG. 20 illustrates a block diagram of a motor and/or sensor module according to an embodiment of the present disclosure.

FIG. 20 illustrates a block diagram of the motor and/or sensor module 2000, which is received by the recess 250 in the flow therapy apparatus. The motor and/or sensor module comprises a blower 2001, which entrains room air to deliver to a patient. In some embodiments the blower 2001 is a centrifugal blower.

Room air enters a room air inlet 2002, which enters the blower 2001 through an inlet port 2003. The inlet port 2003 can comprise a valve 2004 through which a pressurized gas may enter the blower 2001. The valve 2004 can control a flow of oxygen into the blower 2001. The valve 2004 can be any type of valve, including a proportional valve or a binary valve. In some embodiments, the inlet port does not include a valve.

In some embodiments, the blower 2001 can operate at a motor speed of greater than 1,000 RPM and less than 30,000 RPM, greater than 2,000 RPM and less than 21,000 RPM, or between any of the foregoing values. Operation of the blower 2001 mixes the gases entering the blower 2001 through the inlet port 2003. Using the blower 2001 as the mixer can decrease the pressure drop that would otherwise occur in a system with a separate mixer, such as a static mixer comprising baffles, because mixing requires energy.

The mixed air exits the blower 2001 through a conduit 2005 and enters the flow path 2006 in the sensing chamber 2007. A sensing circuit board with sensors 2008 is positioned in the sensing chamber 2007 such that the sensing circuit board is at least partially immersed in the gas flow. The sensors 2008 on the sensing circuit board are positioned within the gas flow to measure gas properties within the flow. After passing through the flow path 2006 in the sensing chamber 2007, the gases exit 2009 to the humidification chamber 300.

Positioning sensors 2008 downstream of the combined blower and mixer 2001 can increase accuracy of measurements, such as the measurement of gas fraction concentration, including oxygen concentration, over systems that position the sensors upstream of the blower and/or the mixer. Such a positioning can give a repeatable flow profile. Further, positioning the sensors downstream of the combined blower and mixer avoids the pressure drop that would otherwise occur, as where sensing occurs prior to the blower, a separate mixer, such as a static mixer with baffles, is required between the inlet and the sensing system. The mixer introduces a pressure drop across the mixer. Positioning the sensing after the blower allows the blower to be a mixer, and while a static mixer would lower pressure, in contrast, a blower increases pressure. Also, immersing at least part of the sensing circuit board and sensors 2008 in the flow path increases the accuracy of measurements because the sensors being immersed in the flow means they are more likely to be subject to the same conditions, such as temperature and pressure, as the gas flow and therefore provide a better representation of the gas characteristics.

Sensing Chamber

The flow therapy apparatus described herein is a modular system. The motor/sensing module including some or all the sensors can separately be removed and replaced if desired. To improve modularity, some or all sensors can be positioned on one sensing circuit board within the sensing chamber that can be placed at least partially within the flow path and the control electronics on the control circuit board can be sealed away from the flow path. The code for the sensing algorithm, including conversion, memory and control, memory and control for calibration, can be located on the sensing circuit board. For purposes of this application, the sensing circuit board is defined as the circuit board positioned within the sensing chamber or sensor module.

Water may contact the sensing circuit board during use of the flow therapy apparatus. For example, the apparatus can be tipped, water from the humidifier chamber can move upstream or into the ports, or a user can turn off the apparatus prior to the completion of the drying mode. Water contact can damage the electronic components on the sensing circuit board, and cause corrosion of sensors and possible contamination of the airflow. To mitigate the effect of water contacting the sensing circuit board, a humidity sensor can be placed on the sensing circuit board to provide warning to the user that the apparatus needs to be checked for possible water ingress or perform a corrective action. If the humidity sensor detects that humidity is higher in the sensing module than expected, the corrective action can comprise the blower initiating a flow sequence to remove water from the sensing circuit board. This can include a pulse to dry the sensing circuit board or other blower mode. The corrective action can also comprise switching on a built-in heater in the humidity sensor or an external heater. In addition, the sensing circuit board can be coated with a conformal coating to prevent water ingress on the sensing circuit board or to mitigate the effect of water ingress on the sensing circuit board, and also to mitigate the effects of oxygen ingress. This can be used in combination with a sealing feature around the electronics, which will be described below. Further, closed frame transducers (described below) may be used because they are less susceptible to damage from water ingress. A water trap can also be introduced between the chamber and the sensing module. One non-limiting example is a one-way valve between the chamber and the sensing module.

Figure 21:
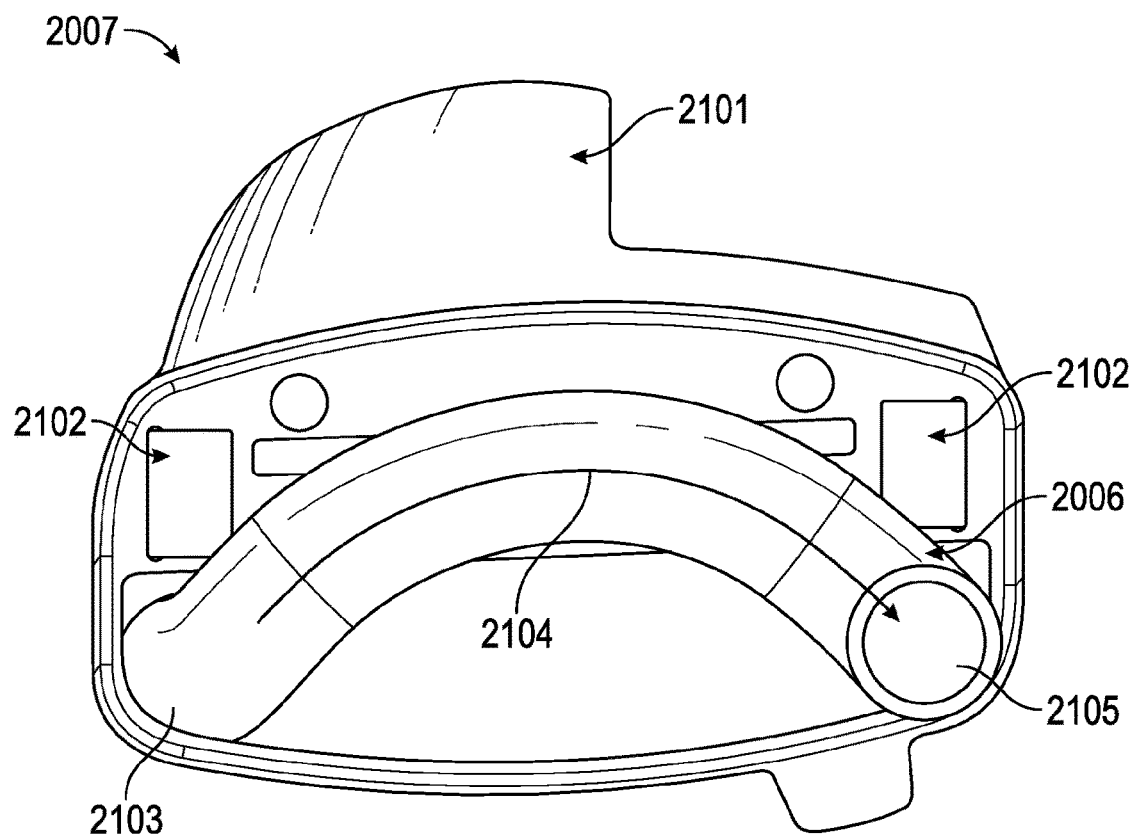
FIG. 21 illustrates a sensing chamber according to an embodiment of the present disclosure.

FIG. 21 illustrates an embodiment of the modular sensing chamber 2007. The sensing chamber 2007 can be positioned downstream of the blower 2001 within the motor and/or sensor module. The sensing chamber 2007 comprises a flow path 2006 and is designed to hold a sensing circuit board 2200 (FIG. 22) in casing 2101.

Gas flows can experience pressure drops during passage through a flow therapy apparatus, which dissipates power and in turn can affect the ability of the system to reach specific flow rates. Pressure losses can occur due to friction in straight sections of a flow path, or from deviations from a straight path, such as bends, valves, contractions, or expansions in the path.

The flow path 2006 has a curved shape. The gas flow enters at an entrance 2103, flows along a curved flow path 2104, and exits on the opposite side of the flow path 2105. In some embodiments, the entrance and exit may be positioned in vertically opposed directions, and the gas flow may enter the path in a vertical upwards direction, then curve around to a horizontal direction, and then curve around to a vertical upwards direction again. In some embodiments, the flow path does not have sharp turns. In some embodiments the flow path has curved ends with a straighter middle section. In some embodiments, the flow path maintains a constant cross-section shape throughout the length of the flow path. In some embodiments, the flow path tapers inward slightly from the first end of the flow path, and widens again to the second end of the flow path, which can speed up the flow for better accuracy in measurements. In some embodiments, the surface of the flow path is lined with a surface modifier/lubricant to reduce friction within the flow path. A number of different flow path configurations can be used. A curved flow path shape can reduce a gas flow's pressure drop without reducing the sensitivity of flow measurements by partially coinciding the measuring region with the flow path.

A sensing circuit board 2200 is positioned in casing 2101 in the sensing chamber such that at least part of the sensing circuit board is overlapping with the gas flow in the flow path 2006. Openings 2102 can be positioned hold ultrasonic transducers 2204 (FIGS. 22A-22B) along the flow path 2006 to measure gas properties within the flow.

The flow path 2006 has a total distance between the transducers. In some embodiments, the flow path has a total distance of between about 10 mm and about 1000 mm, between about 40 mm and about 200 mm, between about 50 mm and about 150 mm, between about 70 mm and about 120 mm, between about 80 mm and 100 mm, or between any of the foregoing values, or about 95 mm.

The flow path 2006 has a total flow distance representing the part of the flow path in line with the acoustic path. In some embodiments, the flow path has a total flow distance of between about 1 mm and about 500 mm, between about 10 mm and about 200 mm, between about 50 mm and about 150 mm, between about 70 mm and about 100 mm, or between about 70 mm and about 88 mm, or between any of the foregoing values or equivalents thereof, or about 75 mm. The total distance between the transducers less the total flow distance equals dead space, which can be at either or both ends of the ultrasonic path where these is no gas flow.

The flow path 2006 can have a diameter greater than about 2 mm and less than about 100 mm, between about 5 mm and about 50 mm, between about 10 and about 30 mm, between about 12 mm and about 25 mm, or about 15 mm to 20 mm, or between any of the foregoing values, or about 16 mm. Decreasing the diameter of the flow path can increase the gas velocity at high flows beyond useful velocities, can increase non-linear effects in sensor measurements, can lead to pressure drops, and can cramp/restrict the sensor arrangement and design. Increasing the diameter of the flow path can take up more space in the system, and can lead to decreases in flow sensitivity. Thus, an optimal balance can be obtained according to the ranges described above. Equivalent ranges can be used with devices that have different flow configurations.

The flow path 2006 has a normalized flow distance that refers to a sensor's 2204 sensitivity equivalent for a total flow distance at a cross-sectional size. Flow sensitivity is affected by total flow distance and gas velocity, which is affected by cross-sectional size. Assuming a circular cross-sectional conduit, flow sensitivity is proportional to $$\frac{D}{\pi r^2}$$

where D represents total flow distance, and r represents cross-sectional radius.

In some embodiments, the flow path 2006 has a normalized flow distance normalized to an 8 mm radius, which is a cross-section of the flow path, of between about 1 mm and about 500 mm, between about 10 mm and about 200 mm, between about 50 mm and about 150 mm, between about 70 mm and about 100 mm, or between about 70 mm and about 88 mm, or between any of the foregoing values or equivalents thereof, or about 75 mm. In some embodiments, the flow path 2006 has a normalized flow distance normalized to a 6 mm radius of between about 1 mm and about 500 mm, between about 10 mm and about 200 mm, between about 20 mm and about 60 mm, between about 30 mm and about 50 mm, or between any of the foregoing values or equivalents thereof, or about 40 mm. In some embodiments, the flow path 2006 has a normalized flow distance normalized to a 10 mm radius of between about 10 mm and about 500 mm, between about 50 mm and about 200 mm, between about 100 mm and about 150 mm, between about 110 mm and about 130 mm, or between any of the foregoing values or equivalents thereof, or about 120 mm. In some embodiments the flow path 2006 has a normalized flow distance normalized to between a 6 mm radius and a 10 mm radius, and the normalized flow distance is between about 40 mm and 120 mm, or between any of the foregoing values or equivalents thereof.

Figure 22A:
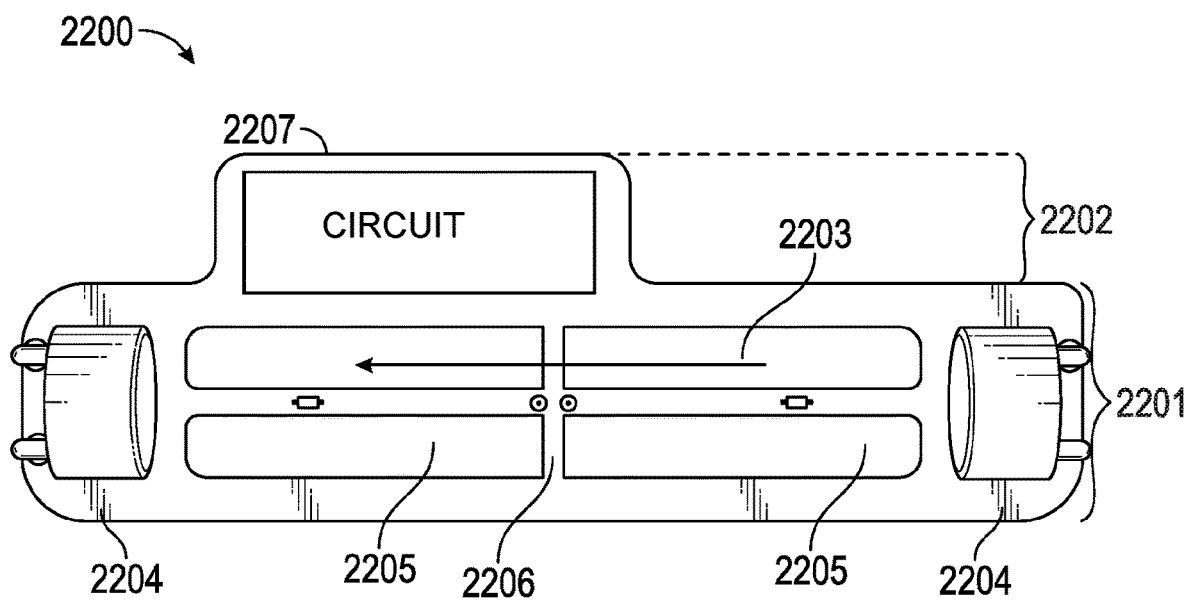
FIG. 22A illustrates a sensing circuit board within a sensing chamber according to an embodiment of the present disclosure.
Figure 22B:
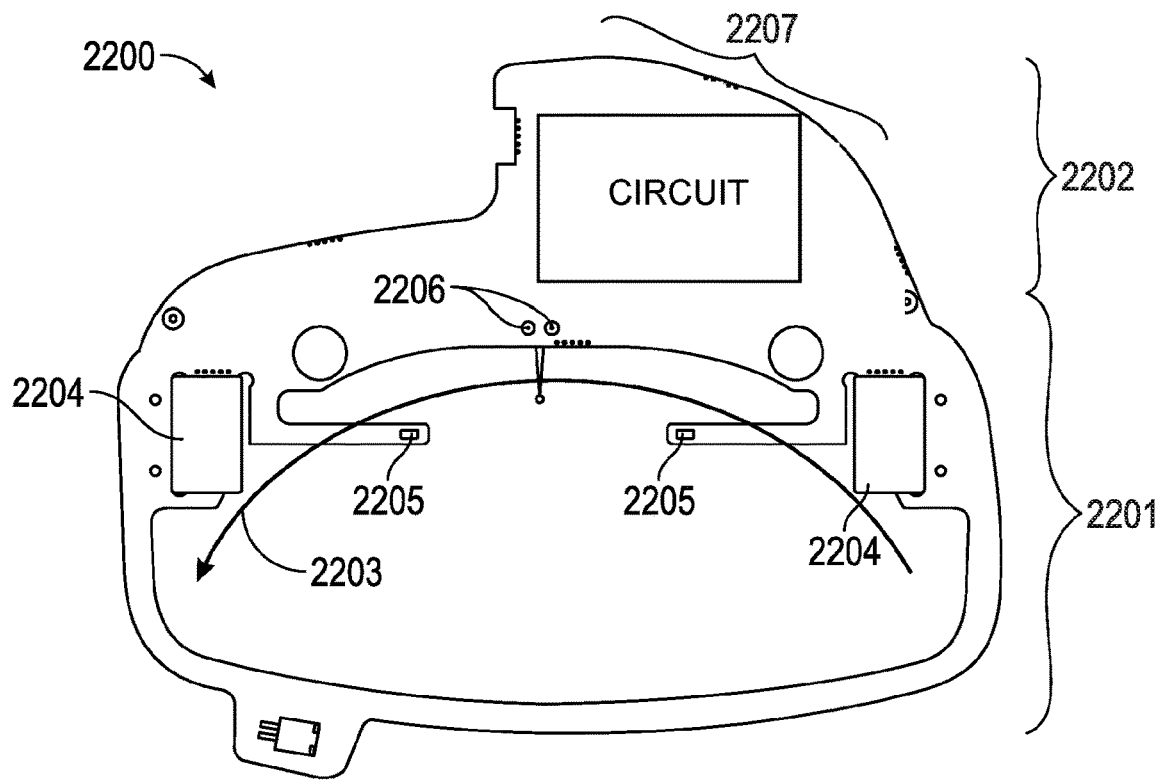
FIG. 22B illustrates a sensing circuit board within a sensing chamber according to another embodiment of the present disclosure.
Figure 22C:
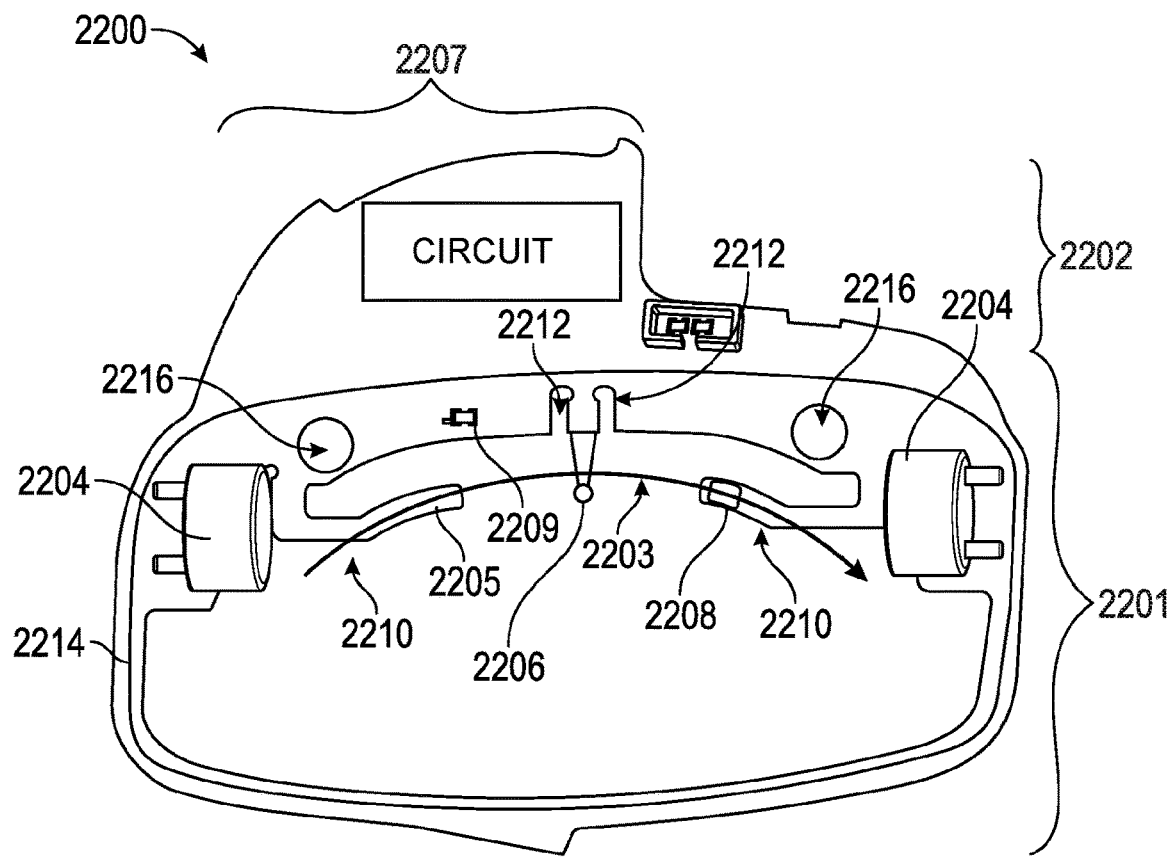
FIG. 22C illustrates a sensing circuit board within a sensing chamber according to another embodiment of the present disclosure.

FIGS. 22A-C illustrate embodiments of the sensing circuit board 2200 configured to be positioned within a sensing chamber. In some embodiments the sensing circuit board 2200 is a printed sensing circuit board (PCB). In some embodiments the circuit is built with electrical wires connecting the electronic components instead of being printed on a circuit board. In some embodiments, at least a portion of the sensing circuit board is mounted outside of the flow path.

The sensing circuit board 2200 can comprise ultrasonic transducers 2204, and one or more of separate gas temperature sensors 2205, heated temperature sensing elements 2206, humidity sensors including humidity only sensors to be used with a separate temperature sensor and combined humidity and temperature sensors 2208, sensors for measuring barometric pressure, sensors for measuring differential pressure, and/or sensors for measuring gauge pressure. A heated temperature sensing element can comprise a heated temperature sensing element, hot wire anemometer, such as a platinum wire or heated thermistor, and/or a negative temperature coefficient (NTC) thermistor. Other non-limiting examples of the heated temperature sensing element include glass or epoxy-encapsulated or non-encapsulated thermistors. The heated temperature sensing element is configured to measure flow rate of the gases. The sensing circuit board 2200 comprises a first portion 2201 and a second portion 2202. The first portion 2201 is positioned to be within the flow path 2006 of the gases, whereas the second portion 2202 is positioned to be outside the flow path 2006 of the gases. The direction of gas flow is indicated in FIGS. 22A-C by the arrow 2203. The direction of gas flow is illustrated as a straight line in FIG. 22A and is curved in FIGS. 22B and 22C. The general direction of air is away from one upstream transducer 2204 and toward another downstream transducer 2204.

The first portion 2201 of the sensing circuit board 2200 can comprise ultrasonic transducers, transceivers, or sensors at each end of the sensing circuit board to measure gases properties along the flow. Positioning sensors in the flow path or module, instead of outside the flow path or module, allows the pair of transducers to both operate within a smaller temperature range relative to one another, or both substantially at one temperature (namely, the temperature of the gas flow). Having them at a substantially homogenous temperature increases accuracy as the transducers are sensitive to temperature. Further, positioning sensors along the flow path allows for measurements and calculations that account for the influence of the gas velocity so that the effect of gas velocity can be removed from the sensor measurement.

The distance between the ultrasonic transducers 2204 on opposite ends of the sensing circuit board 2200 can affect measurement resolution. An increased distance between each of the ultrasonic transducers 2204 can reduce the proportional or fractional error, since in general a measured length will have a certain amount of error, and if the length is increased, the proportion of error generated during measurement is less than for a shorter length. Thus, the overall uncertainty of the measurement decreases. An increased distance can also increase measurement resolution and accuracy, since it allows for a longer time period for acoustic signals between the ultrasonic transducers 2204. However, an increased distance can lead to a weaker signal.

The ultrasonic transducers 2204 can be positioned such that the space between the ultrasonic transducers 2204 at least partially coincides with the flow path 2006. In some embodiments, the ultrasonic transducers are positioned on opposing ends of the sensing circuit board. Because the whole face of the flow path is exposed to the acoustic path, the sound waves propagate through all of the gases in the flow path 2006. Averaging of the waves can occur across the entire flow path rather than a section of the flow path. Averaging over a longer distance reduces error and reduces the dependence of air-oxygen mixing.

The first portion 2201 of the sensing circuit board 2200 can comprise temperature sensors, such as thermistors 2205 within the flow path 2006. Immersing the temperature sensors within the gas flow path increases heat conduction between the gas and the sensor and can allow for more accurate temperature sensing of the gases, and allow a faster response of the temperature sensor. Further, positioning the temperature sensors in the flow path can minimize parasitic heat sources and sinks, for example heat conduction from the wall of the module. In some embodiments, the thermistor 2205 is a negative temperature coefficient (NTC) thermistor. In some embodiments, the thermistor 2205 is a digital sensor.

Figure 27A:
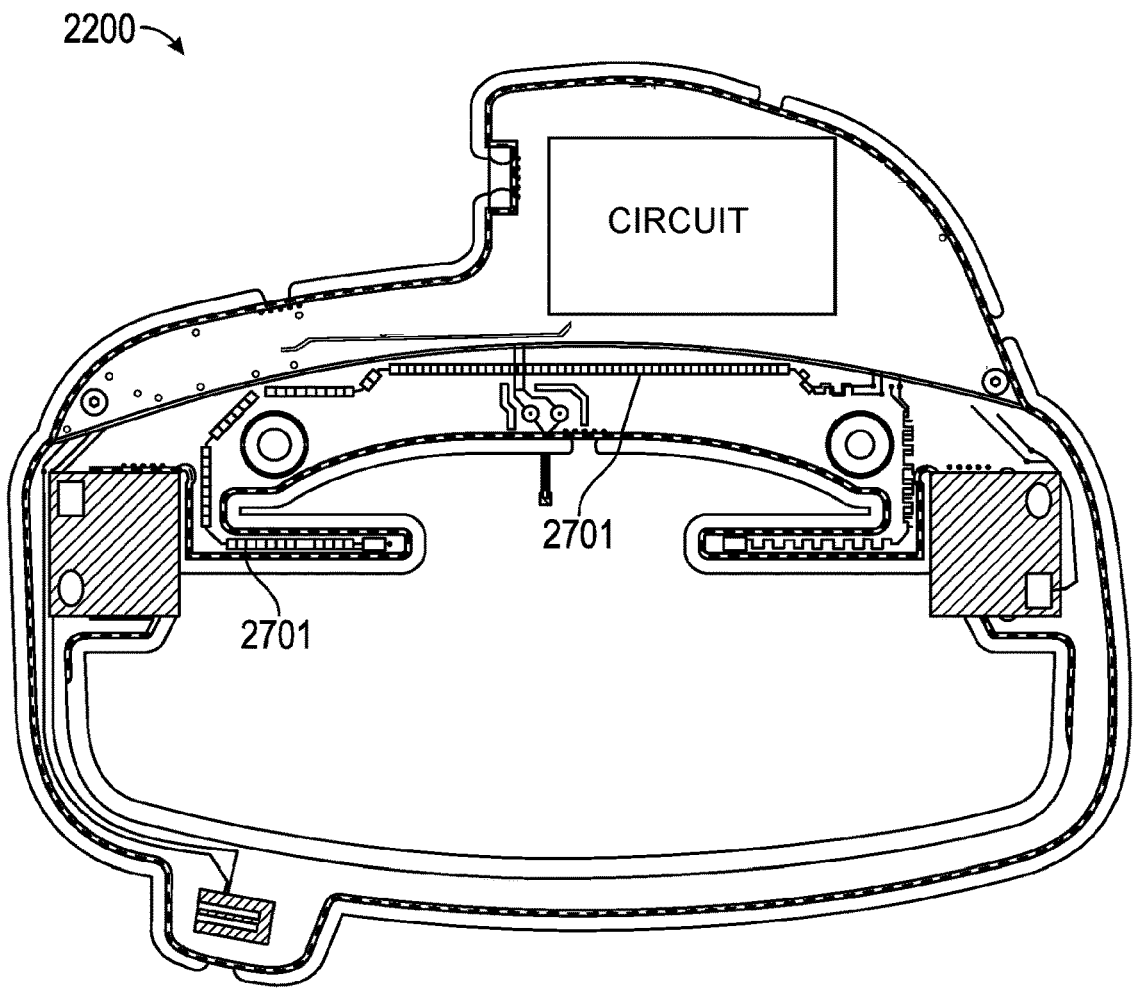
FIG. 27A illustrates a sensing circuit board within a sensing chamber with tracking.
Figure 27B:
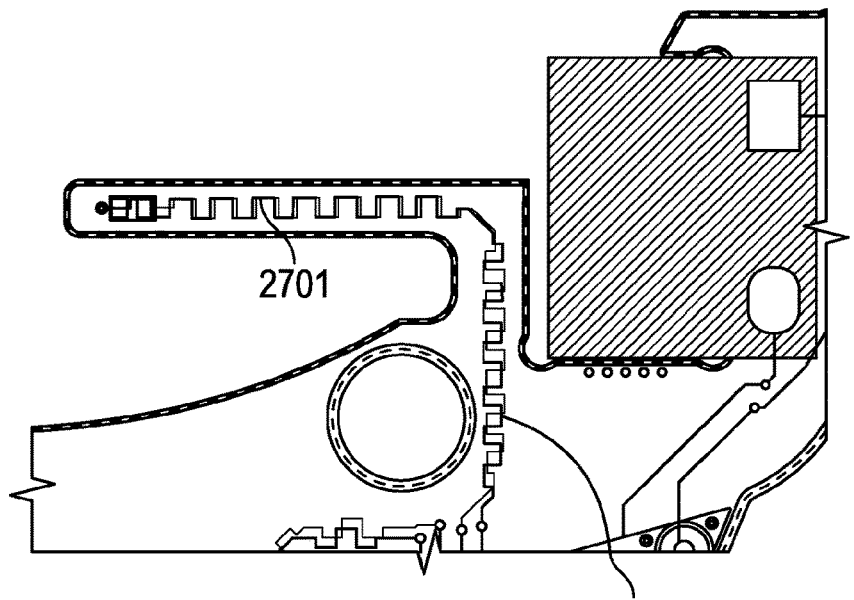
FIG. 27B illustrates an enlarged portion of FIG. 27a showing further detail of the tracking.

In some embodiments the sensing circuit board within a sensing chamber comprises tracking, such as copper tracking, arranged so as to reduce thermal conduction between the chamber wall and sensing circuit board. FIG. 27A illustrates an embodiment of the sensing circuit board 2200 with tracking 2701, and FIG. 27B illustrates an enlarged portion of the sensing circuit board 2200 of FIG. 27A with tracking 2701. In some embodiments the tracking 2701 is located on the outer layers of the sensing circuit board to effect heat transfer to the air. In general, sensing circuit board traces can contribute to a significant portion of the thermal conductance of the overall sensing circuit board, due to the high thermal conductivity of copper or other similar conductive materials. Tortuous, longer tracks can decrease the thermal conduction, but can also increase bulk conductivity of the sensing circuit board, due to the denser plane of copper. In some embodiments, the tracks are thin and long without being very densely arranged. Such a configuration can reduce thermal conduction due to the tracks without substantially increasing bulk conductivity.

The first portion 2201 of the sensing circuit board 2200 can comprise heated temperature sensing elements 2206. The temperature of the heated temperature sensing element can be selectable. The heated temperature sensing elements 2206 are variable-temperature sensors configured to sense gases flow rate as described herein. FIG. 22C shows cutouts 2012 around the heated temperature sensing element 2206. Similar, but in contrast to, tracking described above, the cutouts 2012 can reduce temperature effects on the heated temperature sensing element 2206.

In some embodiments, the sensing chamber comprises a seal dividing the first portion 2201 of the sensing circuit board 2200 from the second portion 2202 of the sensing circuit board. The seal can comprise an O-ring and grooves on either side of the middle section of the sensing circuit board to provide a soft surface for the rigid parts to seal against. In some embodiments, the seal can comprise co-molding, where a soft layer is molded onto the rigid parts of the apparatus to provide a sealing component. The seal can seal off the high-pressure region of the flow path, where sensors on the first portion of the circuit measure characteristics of the gas flow. The seal can prevent gases from escaping the high-pressure region of the flow path and moving towards the electronics of the flow therapy apparatus, and can prevent water from contacting the second portion of the sensing circuit board.

The second portion 2202 of the sensing circuit board 2200 can comprise drivers, microcontrollers, and/or other circuitry 2207. In some embodiments the second portion 2202 comprises a circuit for each of the ultrasonic transducers 2204 to control pulsing by the ultrasonic transducer. Positioning the circuits for the ultrasonic transducers 2204 in proximity to the ultrasonic transducers 2204 decreases noise and increases ability to compensate the circuit for temperature effects. This decreases noise because only a short analogue section is required to transmit the signals from the ultrasonic transducers 2204 to the sensing circuit board processing circuitry 2207 due to the close proximity, and this analogue section, which would be susceptible to noise from surrounding componentry, is sandwiched between two ground planes, such as planes made of copper, in the sensing circuit board 2200. Once the signal has reached the sensing circuit board processing circuitry 2207, any further transmission is via a digital signal, which is robust against noise. The proximity of the ultrasonic transducers 2204 and the circuitry 2207 means the circuitry 2207 is more likely to be at a similar temperature to the gases, thereby compensating for inaccuracies in the reading of the ultrasonic transducers 2204, due to temperature differences between the circuitry 2207 and the gases. In some embodiments, the circuits for the two ultrasonic transducers are on opposite ends of the second portion 2202 of the sensing circuit board 2200. Positioning the circuits on opposite ends can avoid electrical interference between the transmitting and receiving signals.

More details of the sensing circuit board 2200 will be described next in connection with FIG. 22C. Features described below can be incorporated in the embodiments shown in FIGS. 22A and 22B. As shown in FIG. 22C, the sensing circuit board 2200 comprises the first portion 2201 and the second portion 2202. A pneumatic seal 2214 surrounding the first portion 2201 is configured to prevent gases from leaking out of the first portion 2201. The pneumatic seal 2214 can be configured to seal against each surface (upper and under) of the sensing circuit board 2200. The pneumatic seal 2214 on each surface of the sensing circuit board 2200 can be an O-ring seal. Additional sealing features can be used. A non-limiting example is additional plugs added to screw bosses that would be inserted into holes 2216 for mounting the sensing circuit board 2200 in the chamber 2101. The plugs can reduce the likelihood that gases, including oxygen, exit the sensing module or sensing chamber or sensing circuit board 2200 via the screws. The plugs and O-ring seals for sealing the flow path and the circuitry 2207 are both replaceable by co-moulded gaskets, which allows few parts to be used, reduces the assembly time and the chance of operator error.

The first portion 2201 of the sensing circuit board 2200 comprises the ultrasonic transducers 2204 on opposite ends of the sensing circuit board 2200. The ultrasonic transducers 2204 can measure gases characteristics, such as oxygen concentration and flow rate. The ultrasonic transducers 2204 can be open frame or closed frame, as described below. As shown in FIG. 22C, the ultrasonic transducers 2204 are directly mounted on the sensing circuit board 2200. This arrangement can inhibit acoustic coupling that would occur if the ultrasonic transducers were coupled with a casing first and then assembled onto the sensing circuit board 2200. Another advantage of direct mounting is that fewer steps are required to mount the ultrasonic transducers. Further, the distance between the transducers 2204 is fixed, which reduces the likelihood of physical drift over time. FIG. 22C also shows a heated temperature sensing element 2206 configured to measure flow and located in the flow path 2203 about midway between the temperature sensor 2205 and the humidity and temperature sensor 2208. Having both the ultrasonic transducers and the heated temperature sensing element to measure the flow can be advantageous in providing fast and accurate flow measurements across a large range of flow rates, which will be described in detail below.

The sensing circuit board 2200 of FIG. 22C further comprises a temperature sensor 2205 and a temperature and humidity sensor 2208. The temperature and humidity sensor 2208 can monitor the dew point. As shown in FIG. 22C, the temperature sensor 2205 is upstream of the temperature and humidity sensor 2208. The temperature sensor 2205 is closer to the inlet of the flow path 2203 and the temperature and humidity sensor 2208 is closer to the outlet of the flow path 2203. The temperature sensor 2205 and temperature and humidity sensor 2208 are each in close proximity to one of the ultrasonic transducers 2204, respectively. For example, the temperature sensor 2205 and temperature and humidity sensor 2208 are each within between about 10-50 mm of one of the ultrasonic transducers 2204. In some embodiments, the temperature sensor 2205 and temperature and humidity sensor 2208 are each within between about 20-45 mm of one of the ultrasonic transducers 2204. In some embodiments, the temperature sensor 2205 and temperature and humidity sensor 2208 are each within between about 30-40 mm of one of the ultrasonic transducers 2204. Unlike the straight fingers shown in FIGS. 22A and 22B for holding the sensors, the first portion 2201 of the sensing circuit board 2200 of FIG. 22C comprises curved fingers 2010 to position the temperature sensor 2205 and the humidity and temperature sensor 2208 closer to the center of the flow path 2203 to improve accuracy of the readings. The temperature sensor 2205 and temperature and humidity sensor 2208 allow the system to measure temperature at two locations within the flow path 2203. The first location is nearer to the inlet of the flow path and the temperature is measured by the temperature sensor 2205. The second location is nearer to the outlet of the flow path 2203 and the temperature is measured by the temperature and humidity sensor 2208. The two temperature readings provide an approximation of the temperature gradient along the flow path 2203. This approach works well if there are not large temperature gradients within the flow path. For example, a bulk gas temperature calculation can be determined from the two readings using mathematical formulas, such as a weighted sum or other formulas as would be understood by a skilled artisan through the disclosure herein. In addition, the two temperatures provide good approximation of the temperatures of the ultrasonic signals sent and received by the ultrasonic transducers 2204 due to the proximity of the temperature sensor 2205 and temperature and humidity sensor 2208 to the ultrasonic transducers 2204. This allows edge detection methods (described below in the "Ultrasonic Sensing" section) that aim to reduce dependency on the transducers themselves such that only the gases temperature along the flow path 2206 become relevant to the oxygen concentration and flow rate calculations.

Alternatively, with large gradients within the flow path, the following technique can be used. A temperature gradient can be taken between a temperature sensor on a barometric pressure sensor 2209 (to be described in more detail below in the section of the dual absolute pressure sensors) and the temperature and humidity sensor 2208, and this gradient can be used with the gradient between the temperature sensor 2205 and temperature and humidity sensor 2208 to approximate the temperature of the ultrasonic transducer 2004 closer to the temperature and humidity sensor 2208. The same technique can be used to estimate the temperature of the ultrasonic transducer 2004 closer to the temperature sensor 2205. A temperature gradient can be taken between the temperature sensor on the barometric pressure sensor 2209 and the temperature sensor 2205, and this gradient can be used with the gradient between the temperature sensor 2205 and temperature and humidity sensor 2208 to approximate the temperature of the ultrasonic transducer 2004 closer to the temperature sensor 2205.

Since the dew point inside the apparatus is substantially the same as the dew point outside, the humidity sensor 2208 can be placed anywhere within or outside the apparatus if it provides a dew-point measurement. However, it is beneficial to place the humidity sensor in a position such that it is measuring the humidity after the gases have been mixed by the blower. One advantage of this configuration is that the humidity measurement responds faster to changes in humidity. Another advantage is that if the apparatus is used with an oxygen concentrator, the ultrasonic measurements will not depend on the efficacy of the concentrator, whereas measuring the humidity of the ambient air, prior to mixing, results in a small error based on the efficacy of the concentrator.

The second portion 2202 of the circuit board 2200 can comprise drivers, microcontrollers, non-volatile memory such as EEPROM, and/or other circuitry 2207. The use of a microcontroller allows for sensor fusion between the heated temperature sensing element and ultrasonic transducers while the system is running to correct the flow rate that was quickly determined by the ultrasonic transducers with the more accurate heated temperature sensing element. In some embodiments, the microcontroller incorporates non-volatile memory. The use of non-volatile memory serves the following functions and advantages. Calibration parameters and limits for those parameters can be stored, allowing for modularity of the system as described above. More details are provided below in the "Calibration" section. A unique ID for each module can also be stored, which can, for example, be used for tracking of the module during manufacturing and/or in the field. Non-volatile memory also allows for the logging of errors during operation, which can assist in diagnosing faults.

Ultrasonic Sensing

Figure 25A:
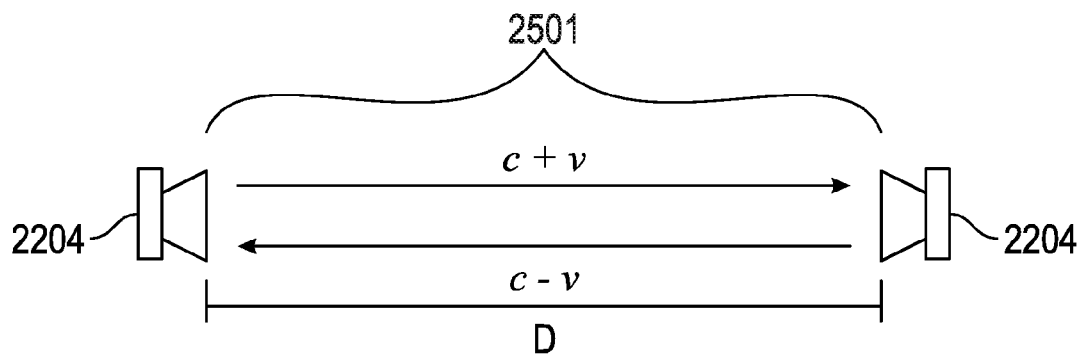
FIG. 25A illustrates a block diagram of an ultrasonic sensing model.

A model of a sensing system utilizing speed of sound (represented by c) and gas velocity (represented by v) is described below and illustrated in FIG. 25A. Two transducers 2204 a distance D apart face each other and each produce a pulse that travels the distance between them (the "acoustic path" 2501) and is received by the other transducer 2204. If the sensor is arranged to have some component of a gas flow parallel to the acoustic path 2501, the signal in the first direction travels with the flow with a speed of c+v, and in the second direction travels against the flow with a speed of c-v. The sensors measure the time of flight of these two signals. Using this time of flight, c and v can be calculated, and the gas flow rate can be determined.

The measured time of flight in the first direction is $$t_1 = \frac{D}{c+v}$$

and in the second direction is $$t_2 = \frac{D}{c-v},$$

which can be solved for the speed of sound and gas velocity:

$$c = \frac{D}{2}\left(\frac{1}{t_1} + \frac{1}{t_2}\right)$$

$$v = \frac{D}{2}\left(\frac{1}{t_1} - \frac{1}{t_2}\right)$$

Figure 25B:
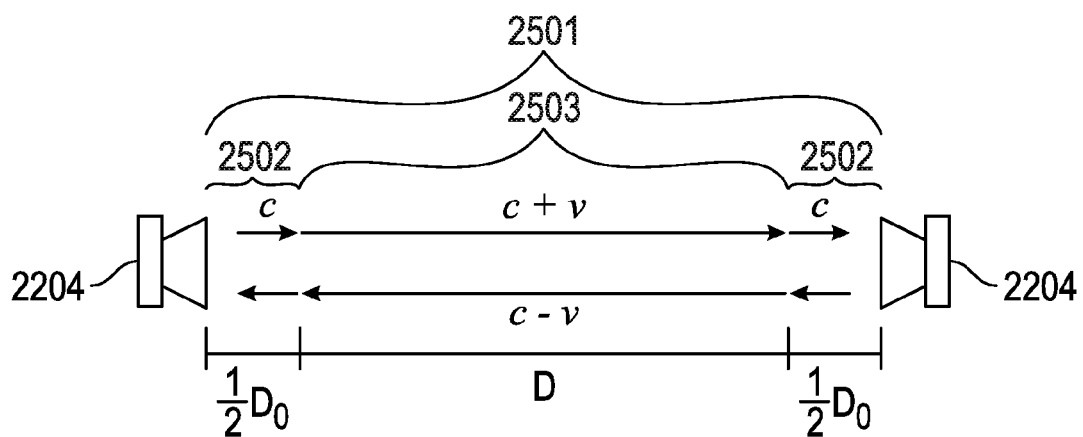
FIG. 25B illustrates a block diagram of an ultrasonic sensing model including dead space.

In practice, there is generally "dead space" at either end of the ultrasonic path where these is no gas flow. A model incorporating dead space 2502 is illustrated in FIG. 25B. In general, these dead space regions 2502 are not clearly defined, and the component of the flow path 2503 in line with the ultrasonic path 2501 may change along the length of the sensing region. However, the smooth curved flow path of the present disclosure reduces change in the flow profile, which in turn reduces dead space. Because the dead space is small, the approximation shown in FIG. 25B is very good and can be treated as if the dead spaces are clearly defined regions. For an average distance $D_0$ of dead space 2502 split between the two ends of the ultrasonic path 2501, and a distance D where there is gas flow 2503, the measured times of flight become $$t_1 = \frac{D_O}{c} + \frac{D}{c+v} \text{ and } t_2 = \frac{D_O}{c} + \frac{D}{c-v}.$$

An exact solution for c can be obtained as:

$$c = \frac{(t_1 + t_2)(2D_0 + D) + \sqrt{(t_1 + t_2)^2(2D_0 + D)^2 - 16t_1 t_2 D_0(D_O + D)}}{4t_1 t_2}$$

The gas velocity is then given by:

$$v = c\frac{D}{2}\left(\frac{1}{ct_1 - D_0} - \frac{1}{ct_2 - D_0}\right)$$

The expressions can be simplified based on the assumption that the speed of sound will be significantly higher than the gas velocity, so by approximating $c^2 \gg v^2$ the expressions simplify to:

$$c \approx \frac{D + D_0}{2}\left(\frac{1}{t_1} + \frac{1}{t_2}\right)$$

$$v \approx \frac{(D_0 + D)^2}{2D}\left(\frac{1}{t_1} - \frac{1}{t_2}\right)$$

A volumetric flow rate can be obtained by multiplying the gas velocity v by the effective cross sectional area, A: Q=vA.

If the flow forms an angle with the acoustic path, the volumetric flow rate can be expressed as $$Q = \frac{v}{\cos\theta}A$$

The effective cross sectional area may be considered to be a lumped parameter of a combination of known and unknown parameters that sufficiently represents the cross sectional area.

In some embodiments, the equations given above are reduced to other forms.

Figure 23A:
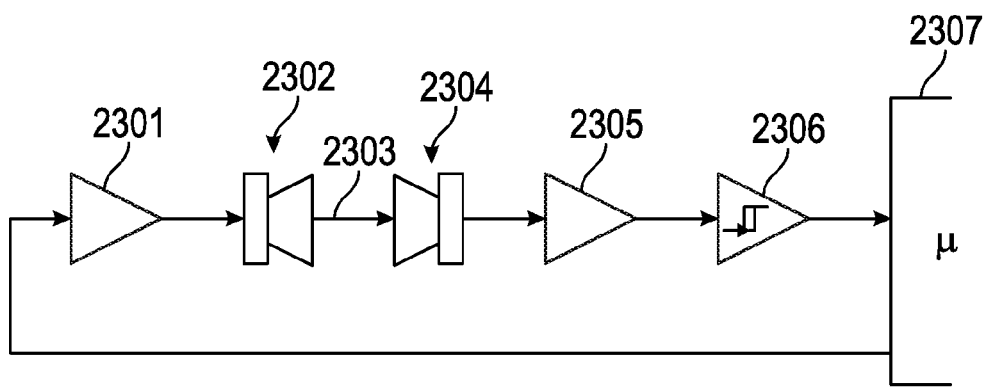
FIG. 23A illustrates a circuit representation of an implementation of transducer signalling, according to an embodiment of the present disclosure.
Figure 23B:
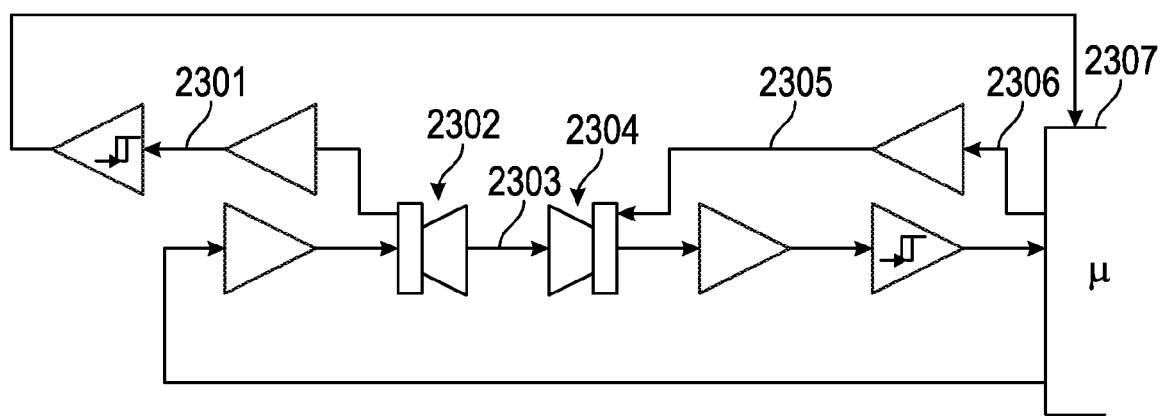
FIG. 23B illustrates a circuit representation of an implementation of bidirectional transducer signalling, according to an embodiment of the present disclosure.

FIG. 23a illustrates a circuit representation of an implementation of transducer signalling during ultrasonic sensing, according to an embodiment of the invention. The transmitter driver 2301 drives the transmitter 2302 to emit a signal, which propagates 2303 through the air to a receiver 2304. An amplifier 2305 amplifies the waveform, the edge or time delay is detected 2306, and a microcontroller 2307 provides the drive signal and captures the edges. FIG. 23b illustrates a circuit representation of signalling in both directions, by superimposing two directions of pathway of FIG. 23a. A number of topologies can be implemented.

The transmitter driver 2302 can comprise four transistors operating as inverters, the first two for level shifting, and the second two forming a half-bridge driving the transducer. Separating the transmitter driver 2302 from the transmitter/transducer 2303 allows the transducer 2303 to be isolated from the driver 2302 when the transducer 2303 operates as a receiver 2304 during acoustic signalling in the opposite direction. In some embodiments, the transmitter driver is an integrated driver chip. In some embodiments, the transmitter driver transistors are MOSFETS, which can exhibit a smaller delay and have good stability across temperature. In some embodiments, the transmitter driver transistors are bipolar junction transistors.

In some embodiments, the transmitter 2303 can comprise an "open frame" piezoelectric transducer, operating at 25 kHz, 40 kHz, or any other frequency. In some embodiments, the transmitter 2303 can comprise a "closed frame" piezoelectric transducer, operating at low voltages, such as below about 20V. Low voltages are desirable for oxygen safety. On the one hand, open frame transducers offer more amplitude, better sensitivity and signal-to-noise ratio, and work at lower voltage, thus are more suitable for use with the flow therapy apparatus described herein. However, open frame transducers can be less reliable because they are not sealed and therefore more likely to be damaged by water ingress and be more susceptible to mechanical damage, such as when the cone falls apart. On the other hand, closed frame transducers are not very susceptible to water ingress or mechanical damage because closed frame transducers do not have cones. However, closed frame transducers often require high voltages that are above the common operating voltage of the flow therapy apparatus.

The receiver 2304 can comprise an "open frame" piezoelectric transducer, operating at 25 kHz, 40 kHz, or any other frequency. In some embodiments, the receiver 2304 can comprise a "closed frame" piezoelectric transducer, operating at low voltages, such as below about 20V. In some embodiments, the transmitter 2303 and receiver 2304 are the same type of transducer.

Figure 24A:
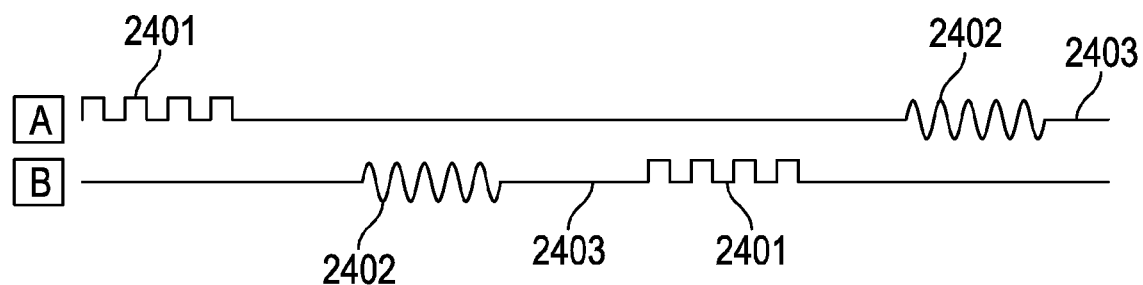
FIG. 24A schematically illustrates transducer signal pulses.
Figure 24B:
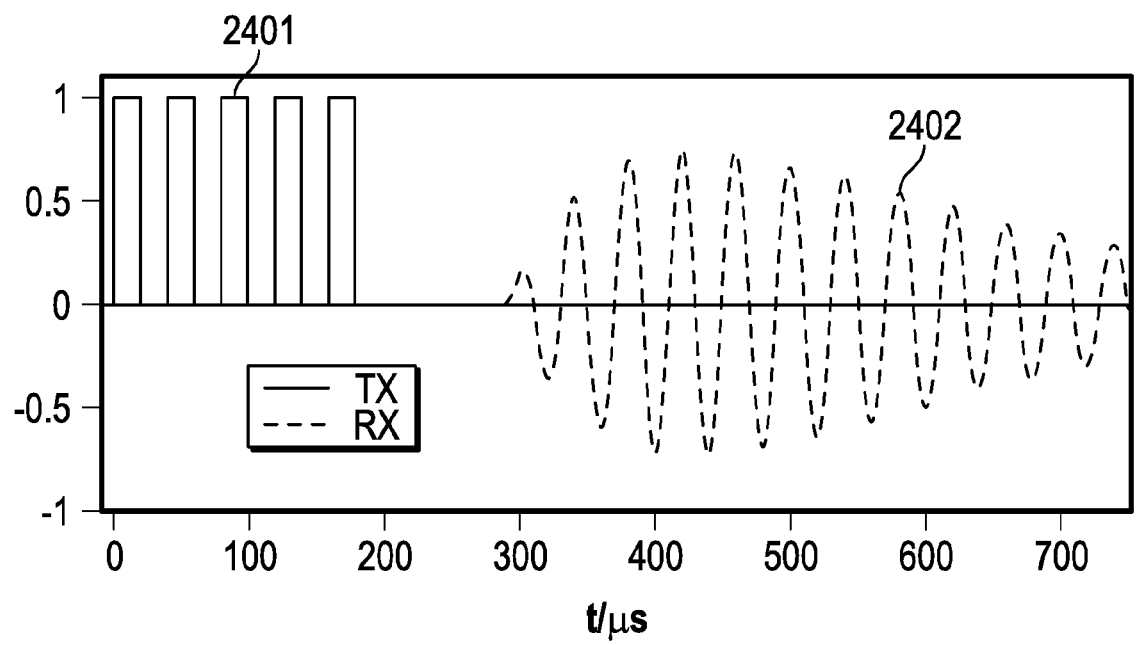
FIG. 24B illustrates a propagated transducer signal as it is transmitted and received.

FIG. 24a schematically illustrates signals as they are transmitted and received in opposite directions, and FIG. 24b illustrates a propagated signal 2303 as it is transmitted and received. A pulse train is applied to the transducer/ transmitter 2302 and can be a pulse or burst of pulses 2401, or a square wave. Since piezoelectric transducers can be very resonant, the signal produced by the transducer/transmitter 2303 may not be a square wave, but may instead be an enveloped sinusoidal wave. Similarly, the waveform 2402 received by the transducer/receiver 2304 may not be exactly the transmitted sound wave, but be based on the combined effect of the transmitted wave and the transducer/receiver's resonance. After a recovery phase 2403, another pulse train 2401 is applied to the transducer/receiver 2304 and received by the transducer/transmitter 2303.

Figure 24C:
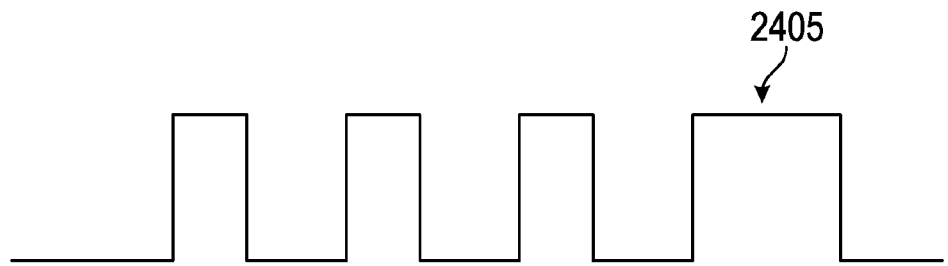
FIG. 24C schematically illustrates example tranducer pulses designed to reduce ringing.

The period between pulse trains can be varied, however, decreasing the period (for example by moving the pulse trains closer together in time) can cause interference between subsequent trains due to ringing of the transducers. For example, if the time between pulse trains is decreased, a new pulse train may start before the signal from the previous pulse train has settled. Thus, measurements determined from a particular point in the pulse train may overlap with the end of the previous pulse trains' signals as it settles. The ultrasonic transmitters can have features designed to reduce ringing. As shown in FIG. 24C, the ultrasonic transmitters can lengthen a pulse 2405 so that it becomes close to or at 180° out of phase with the driving signal to quickly reduce the ringing of the pulse. Only a few additional out of phase pulses need be transmitted to aid with reducing the ringing as too many out of phase pulses will cause the ringing to start again. In some embodiments, the pulse can be altered such that it is out of phase by less or more than 180 degrees. In other embodiments, one or more pulses can be omitted to reduce ringing.

Any number of pulses can be transmitted in each pulse train. However, increasing the number of pulses can increase echoes, which make the behaviour of the sensor unpredictable. Decreasing the number of pulses can result in insufficient amplitude to obtain an accurate measurement. In some embodiments, the total transmission time of the pulse train is less than the time of flight. Greater transmission times can lead to errors in measurements, from, e.g., signals interfering with each other, interference from echoes in the gases, electrical noise from the pulsing, or sound traveling through the housing. In some embodiments the number of pulses transmitted is between 1 and 50, between 1 and 10, 5, or any other number of pulses. The frequency of the pulses can be varied. The frequency of the pulses can be the same as the frequency of the transmitter 2303, or lower than the frequency of the transmitter 2303, or higher than the frequency of the transmitter 2303.

The amplifier 2305 can comprise a common-emitter bipolar junction transmission (BJT) amplifier with no decoupling capacitors. This type of amplifier can achieve a low phase delay and good frequency response. In other embodiments the amplifier 2305 can comprise op-amps or other integrated amplifiers.

The edge/time delay 2306 can be measured by measuring the zero-crossings of the received waveform, i.e., by detecting the points on the 'RX' curve 2402 above where it crosses zero as shown in FIG. 24B. In practice it is difficult to detect the first few edges of the waveform, where the receiver is just beginning to "ring up", since the signal to noise ratio is very small. Typically, then, the starting point for measurement will be one or more edges after the actual start, and the true time of flight must be calculated from this. In a simple linear regression system, at least two edges are measured, and the period of the waveform is computed, so that a measured point can be extrapolated back the appropriate number of periods to find the start of the waveform. If many edges are measured, a linear regression may be used to compute the time offset at the zeroth edge. The peaks of the waveforms may be computed first (and then used for the same type of calculations), by taking the arithmetic mean of adjacent edges. The arithmetic mean calculation mitigates against the effects of offsets in the zero-point of the edge detection, which can otherwise skew the result slightly.

In practice, these linear regression methods have a fundamental limitation. Both the transmitter and receiver have non-zero phase responses, and as described above, most piezoelectric transducers are highly resonant. Moreover, the exact phase response and resonant frequency of each transducer can vary between parts, across temperature, and over time. The actual waveform that is received, then, is the drive waveform convolved with the transmitter impulse response, and convolved with the receiver impulse response. Accordingly, the received waveform is not a true enveloped sinusoid, but rather has a complex phase delay at its start and a frequency that varies as the waveform "rings up", possibly resulting in a partial or complete beat, depending on the differences between resonant frequencies of the drive waveform, and TX and RX transducers, or more generally the impulse responses. Since the underlying resonant frequencies shift under different temperature and other waveform-shifting conditions, that shape of the received waveform also shifts. Any simple linear regression on the edges would be negatively affected by the shifts, as the simple linear regression assumes that the period of the waveform does not change from the measured edges to the extrapolated edges. This results in the need for temperature and other empirical corrections to be added to the linear regression or similar calculation to account for these additional temperature and similar waveform shifting effects. These corrections may in turn also not be accurate over time or across difference transducers.

One method to mitigate the temperature drifts or other similar effects which shift the waveform is to adjust the drive frequency. As described above, many transducers have a somewhat consistent shift in resonant frequency across temperature, so the drive frequency may be varied in accordance with this. In an alternative embodiment, the resonant frequency of the transducers may be estimated from the sensed waveform, and the drive frequency adjusted accordingly, to allow the system to dynamically match the drive frequency with the resonant frequencies, and minimise spurious phase delays.

In some embodiments, to better account for these discrepancies, and in particular the mismatch between transmitter and receiver, which cannot be directly adjusted, a more general expression weighting each edge can be used. For example, weighted vectors can be used, such as $t=\delta+\Sigma_i w_i E_i$, where t is the time of flight, $w_i$ is the weight for the $i^{th}$ edge and $E_i$ is the time of the $i^{th}$ edge. By choosing an appropriate set of weights, it is possible to produce an expression that closely approximates an inversion of the convolution process, even for reasonable shifts in TX and RX resonant frequencies. In this way, only small or no empirical temperature corrections are required in the time of flight calculation.

In some embodiments, the edge/time delay can be measured by measuring the amplified waveform. The amplified waveform is actually the captured and stored RX wave shown in FIG. 24B. Measuring the amplified waveform can allow for improved fault detection, since the actual waveform is being observed, and can also be used for more elaborate estimations of the time delays. For example, a cross correlation can be performed between the received waveform and a reference, either recorded earlier or defined prior, to produce a time of flight measurement. The reference can be a separate or a previous wave. Since the cross correlation is performed across a complex shape, this method does not depend on the "windowing" done in edge detection, which requires knowing where the edge must fall in a predefined window in order to know that the correct edge is being detected. The independence from the need of "windowing" in turn allows for a wider range of speed of sound sensing. Even if the speed of sound range would cause an edge to fall outside of a window, the cross correlation can still correctly measure the time of flight, which can then be used to define a new edge window for edge-based measurements. In this way gases that might not have been usable on a particular system due to their high speed of sound range can become usable, for example, heliox or carbon dioxide, which produce speed of sound changes several times larger than that due to oxygen. The comparison of the waveform with a reference can also highlight anomalies during operation, such as a low signal amplitude, interference, an unacceptable shift in transducer frequency, and so on. The waveforms in each direction can also be cross-correlated with each other to produce a differential time of flight, from which the flow rate can be calculated.

The microcontroller 2307 provides the drive signal and captures the edges. The microcontroller can operate at any frequency, though higher frequencies can improve resolution. The microcontroller 2307 can operate at a frequency of 24 MHz, 48 MHz, 72 MHz, 120 MHz, or any other frequency.

Calibration

In some embodiments, the sensors can be used in combination to provide redundancy and calibrate the flow therapy apparatus. For the purposes of this specification calibration refers to checking variables and/or adjusting the system, measurements, and/or display if there are differences between the measured variables and an expected or reference variables. Heated temperature sensing elements have a logarithmic response which produces increased sensitivity at low flows compared to ultrasonic. The heated temperature sensing elements can provide improved low flow measurement accuracy, but the ultrasonic transducers can provide fast measurements. A control system can turn off the blower and the oxygen flow to create a situation with known values, and compare the readings from different types of sensors to determine whether the sensed values are acceptable. The control system can then vary the blower speed and oxygen flow rate, and use or compare the readings from the different types of sensors and calibrate accordingly.

The calibration can be an adjustment of a parameter in a mathematical model used to calculate gas characteristics, including gas velocity, flow rate, gas temperature, humidity, pressure, and/or oxygen concentration. In particular, where a gas characteristic is calculated based on a mathematical model, model parameters in the relation can exhibit unknown variation. By using sensors to take measurements during known conditions, these measurements can be used in the model to solve for unknown parameter(s).

Calibration adjustment of an unknown parameter can account for more variation in the system than solely attributable to the direct physical interpretation of that parameter (i.e., the adjustment can account for unknown variation in multiple parameters). This can occur in at least two situations. First, two parameters might be inseparable, in which case the calibration adjustment can be considered as combining the effects of the two parameters. For example, in the ultrasonic sensing model for gas velocity described earlier, the parameters of the term $$\frac{(D_0 + D)^2}{2D}$$

are grouped with no variables to distinguish them, so for the purposes of calibration, their combined value can be adjusted. Second, the system may not have enough calibration points to solve for all of the parameters, in which case the calibration adjustment can approximate variation in multiple parameters. For example, in the ultrasonic model for speed of sound described earlier, the parameters $D+D_0$, $t_1$, and $t_2$ can exhibit distinct variability that can be distinctly accounted for by using multiple calibration points. However, in the simpler case of using one calibration point, a single one of the foregoing parameters can be solved to account for total variability of all of the foregoing parameters. In this second case, additional measurements can be taken to validate the system, and/or to check whether additional calibration points may be needed.

For example, in the model for speed of sound described earlier, $$c \approx \frac{D+D_0}{2}\left(\frac{1}{t_1} + \frac{1}{t_2}\right)$$

using the known speed of sound, and a calibration point measurement of ultrasonic times of flight $t_1$ and $t_2$, the parameter to be calibrated can be $D+D_0$, where $$D + D_0 = \frac{2c}{\frac{1}{t_1} + \frac{1}{t_2}}$$

from the model above. Such a calibration point can be taken at any flow rate, since the gas velocity does not appear in the model, but taking the calibration point at zero flow can reduce residual cross effects between gas velocity and speed of sound.

However, in the model for flow rate described earlier, $$Q_v = A\frac{(D_0 + D)^2}{2D}\left(\frac{1}{t_1} - \frac{1}{t_2}\right)$$

a similar calibration cannot be taken at zero flow, because the term $$\frac{1}{t_1} - \frac{1}{t_2}$$

can be expected to equal 0. However, a slight asymmetry between the two directions can generally be expected, mainly due to the transducer delays. The asymmetry can be modeled as:

$$\delta_0 = \frac{t_2 - t_1}{2}.$$

Using this model for asymmetry, the model for gas velocity can be adjusted to:

$$Q_v = A \frac{(D_0 + D)^2}{2D} \left( \frac{1}{t_1 + \delta_0} - \frac{1}{t_2 - \delta_0} \right).$$

The remaining values in the model are based on the geometric shape of the flow path and less susceptible to variation. Thus, the adjusted model for gas velocity can be used to calibrate at zero flow.

In some embodiments, the calibration method is not dependent on a zero flow rate and can be applied at any flow rate. The calibration method can allow for separate delays, $\delta_1$ and $\delta_2$, in each time of flight direction, so that the speed of sound computation becomes:

$$c = \frac{D + D_0}{2} \left( \frac{1}{t_1 + \delta_1} + \frac{1}{t_2 + \delta_2} \right)$$

And similarly for v, where the values of c and v are known, the delays are computed by:

$$\delta_1 = \frac{D_0}{c} + \frac{D}{c + v} - t_1$$
$$\delta_2 = \frac{D_0}{c} + \frac{D}{c - v} - t_2$$

In this case the value of $D+D_0$ can be fixed for all sensors or separately determined during manufacture. If it is desired to calibrate c or v separately, then the current computed value for the remaining variable can be substituted. For example, to calibrate the flow without affecting the speed of sound reading, the current sensed value of c is used, producing values for $\delta_1$ and $\delta_2$ that influence v, but not c. In this manner, the flow rate can be calibrated at any known flow, and conversely for the speed of sound.

Calibration for other sensors can be similarly employed. For example, heated temperature sensing elements can be modelled by King's Law or a derivative thereof, and unknown parameters can be adjusted based on measurements at calibration points. In some embodiments, the redundancy provided by the ultrasonic transducers, which are fast but not always accurate at low flows, and by the heated temperature sensing element, which is slow but has good accuracy at low flow, can be combined during operation to provide a continuous reading that is both fast and accurate at low flows. For example, low flow comprises a flow rate of less than about 25 L/min, or less than about 20 L/min, or less than about 15 L/min. For example, each time a flow reading is taken from the heating temperature sensing element, it may be used to compute or adjust a calibration parameter of the ultrasonic transducers, as described in the foregoing paragraphs, thereby continuously correcting any error or drift in the ultrasonic transducer's reading. The adjustment may be performed directly or using filters to only adjust the parameter by a certain amount or at a certain rate, and/or the level of adjustment may be weighted on flow or other sensed parameters, or using known system response characteristics to estimate an optimal weighting, similar to a Kalman filter. The adjustment may also be performed directly on the ultrasonic transducers' flow reading instead of on the calibration parameter in a similar manner.

Figure 26A:
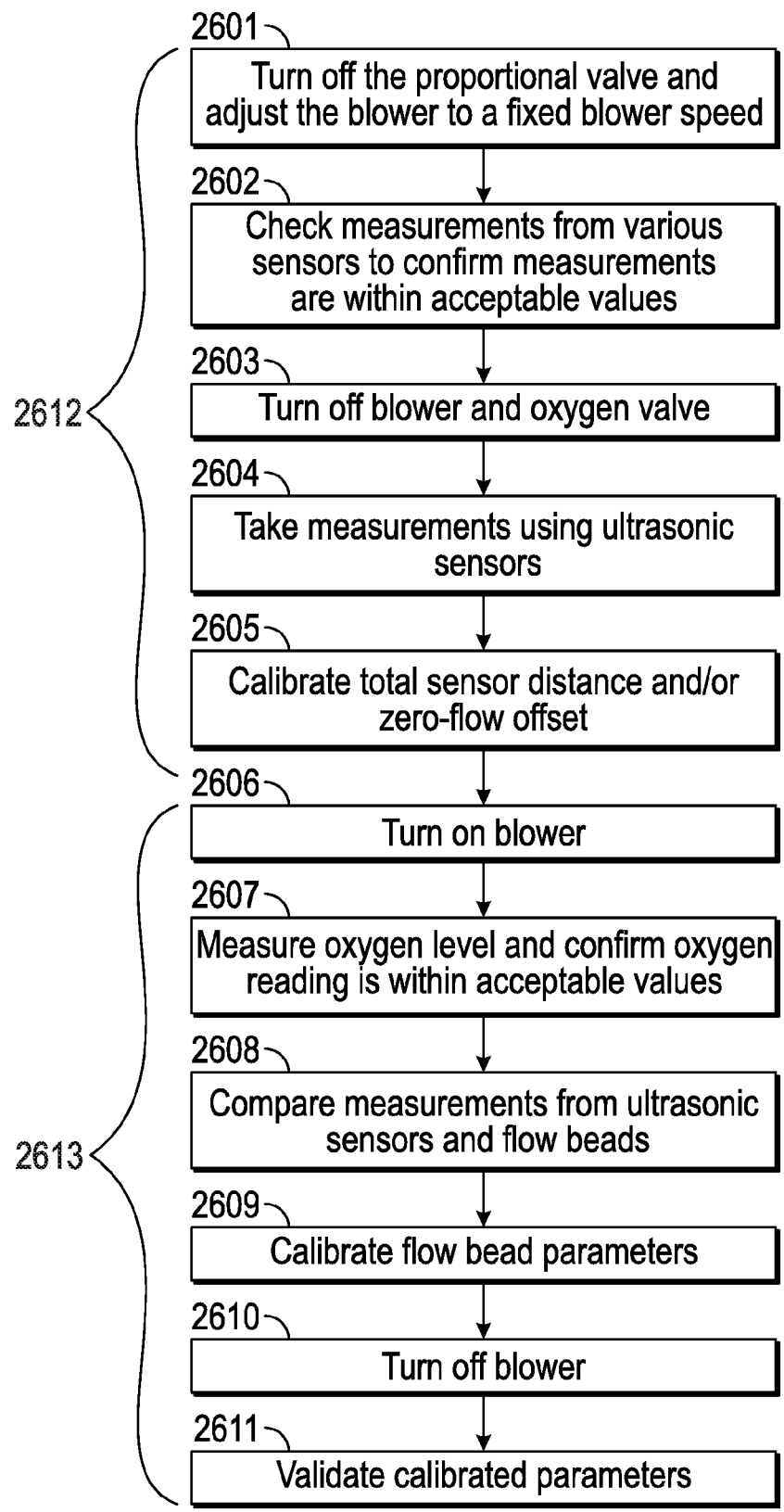
FIG. 26A is a flow chart illustrating a calibration system, according to an embodiment of the present disclosure.

In some embodiments, calibration of the system can thus be employed in the following steps, illustrated in the flow chart of FIG. 26A. First 2601, the control system can turn off the valve and adjust the blower to a fixed blower speed. Measurements from various sensors (e.g., ultrasonic, temperature, humidity, pressure) can be checked to be within acceptable values to ensure that the system is operating properly 2602. For instance, the approximate flow rate from the ultrasonic transducers can be checked to ensure that the flow path is not blocked, and/or pressure can be measured by a pressure sensor and confirmed to be within acceptable values.

Next, the control system can turn off the blower and valve to create a zero flow rate 2603. Measurements from the ultrasonic transducers can be used to calibrate the total sensor distance ($D+D_0$) and zero-flow offset 2605, as described above. The reading from the ultrasonic transducers can be used as a reference to calibrate the heated temperature sensing element. However, heated temperature sensing elements generally require two calibration points, because heated temperature sensing elements have more unknowns in the system (e.g., temperature sensitivity, temperature, and/or power gradients). Having calibrated the ultrasonic transducers, they can be used as a reference to generate at least one new condition to carry out additional calibration, for example, at zero-flow or at one or more non-zero flow conditions.

After calibrating the ultrasonic transducers 2612, the system can use the calibrated ultrasonic transducers to calibrate other sensors 2613. The blower can be turned on 2606 so that a flow is going through the system. With the valve still off, the oxygen concentration is known to be near 20.9% (the concentration of oxygen in air). Measurements can be taken to check that the oxygen reading is within acceptable values 2607. Likewise, if the apparatus is attached to a known oxygen source, the valve can be fully opened, and the blower set to a low flow, and measurements can be taken to check that the oxygen reading is near 100% or within an accepted range of values, for example where an oxygen concentrator delivers only approximately 100% oxygen. Further, at 100% oxygen, measurements taken by a relative humidity sensor can be taken to check that the relative humidity reading is near 0% or within an accepted range of values.

By taking measurements with both the ultrasonic transducers and heated temperature sensing elements and comparing those measurements 2608, the control system can calibrate the heated temperature sensing element parameters accordingly 2609. The blower can be adjusted to create additional sets of flows, which can be measured for additional calibration points.

The control system can then turn off the blower 2610, and calibration of the ultrasonic transducers and heated temperature sensing elements can be validated at known zero flow 2611.

Figure 26B:
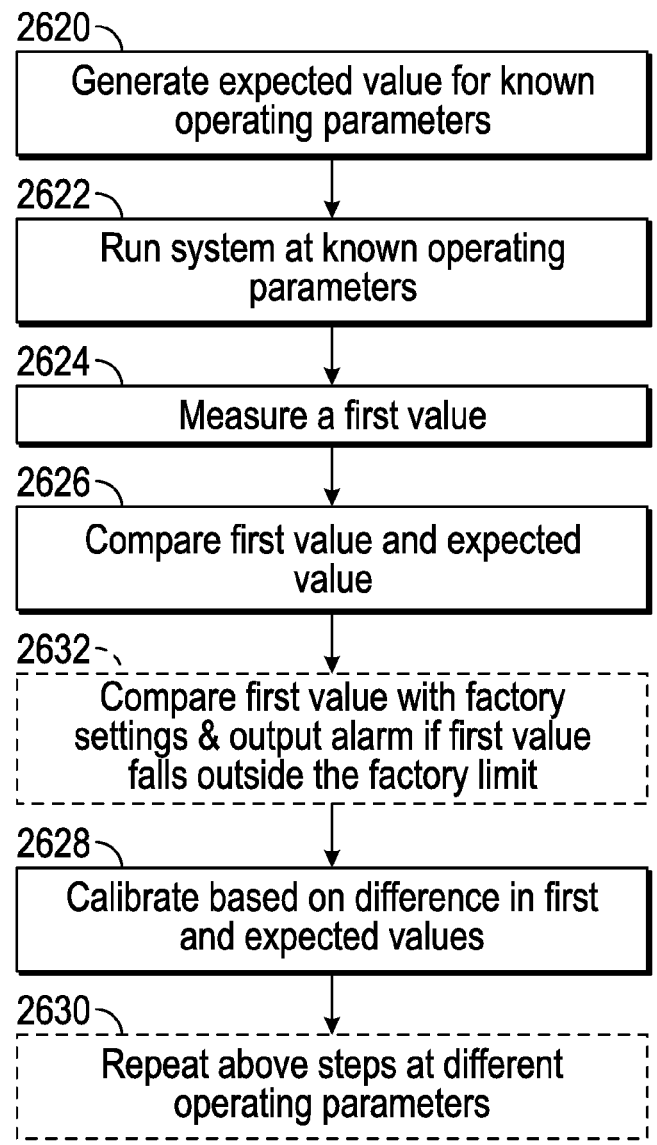
FIG. 26B is a flow chart illustrating a calibration system, according to another embodiment of the present disclosure.

FIG. 26B illustrates another embodiment of calibration steps of the system. In step 2620, the system generates an expected value for given operating parameters. The expected value can be from a lookup table, user input, calculated value, or the like. In step 2622, the system is run at the given and known operating parameters from the step 2620. In step 2624, the system measures a first value using one of the sensors. In step 2626, the system compares the first value with the expected value from the step 2620. In step 2628, the system can calibrate the measurement based on the difference of the first and expected value. Measurements that can be calibrated include the speed of sound, flow with the blower off (zero flow rate) or at a particular flow rate. Optionally, at step 2630, the system can repeat once or several times the steps 2620-2628 by running at different operating parameters as a check. In some embodiments, the system can optionally compare the first value with factory settings at step 2632. The comparison can be done either at the comparison step 2626 or after the comparison step 2626 but before any calibration occurs. If the first value is outside the limit, the system can stop the calibration process and output an alarm. The limit can be, for example, a factory tolerance or other predetermined calibration limits within which the apparatus is supposed to run.

In some embodiments, the calibration system checks its parameters and adjusts its parameters as required to fit within acceptable limits. In some embodiments, the calibration system checks its parameters to determine whether the sensed values are acceptable, without adjusting parameters. Calibration of the system can be performed during manufacture to determine acceptable values that will serve as references for later calibrations of the system. Calibration can be performed in a factory, by a user, or automatically by the system. For example, the system can prompt a user that calibration is required, or automatically calibrate the unit such that the system is calibrated whenever it is needed or only calibrated at an appropriate time. In other examples, the user can initiate the calibration system.

Dual Absolute Pressure Sensors Arrangement

The flow therapy apparatus can comprise dual absolute pressure sensors, one of which is the barometric sensor 2209 of FIG. 22C. Commonly a gauge sensor is placed on the sensing module to measure the difference between the gases flow pressure and the ambient pressure. The difference between the gases flow pressure and the ambient pressure is a value for monitoring how the user of the flow therapy apparatus feels when the gases are delivered to the user. A gauge sensor measures within a small range and thus has the advantages of high resolution, less noise and more accuracy than absolute pressure sensors. However, the gauge sensor has several disadvantages. The gauge sensor requires installation of two pipes. The pipes can be problematic for several reasons. The pipes, for example, may fall off leading to oxygen leak. Leaking oxygen is a safety hazard. The gauge sensor is also sensitive to positioning because the ports of the sensor cannot face the flow or be in a region having stagnation pressure. Also, as the pipes need to go through holes in the case housing the sensor, the structure of the case is less robust.

As the flow therapy apparatus described herein controls the flow rather than controlling a delivered pressure at the patient, the system is less affected by noise in the readings. For example, this can be useful for synchronizing with the patient's breath. Noise can generally be filtered out. Absolute pressure sensors in the therapy apparatus can thus offer a simpler mechanical design than the gauge pressure sensor by eliminating the need for any pipes behind the seal, without compromising accuracy in the readings for purposes of controlling the flow.

Figure 28:
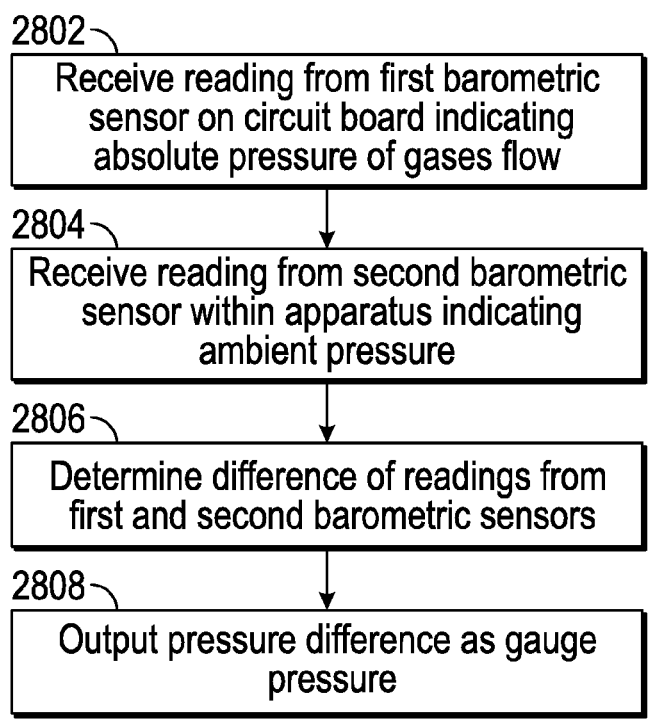
FIG. 28 is a flow chart illustrating determination of a gauge pressure using two absolute pressure sensors.
Figure 29:
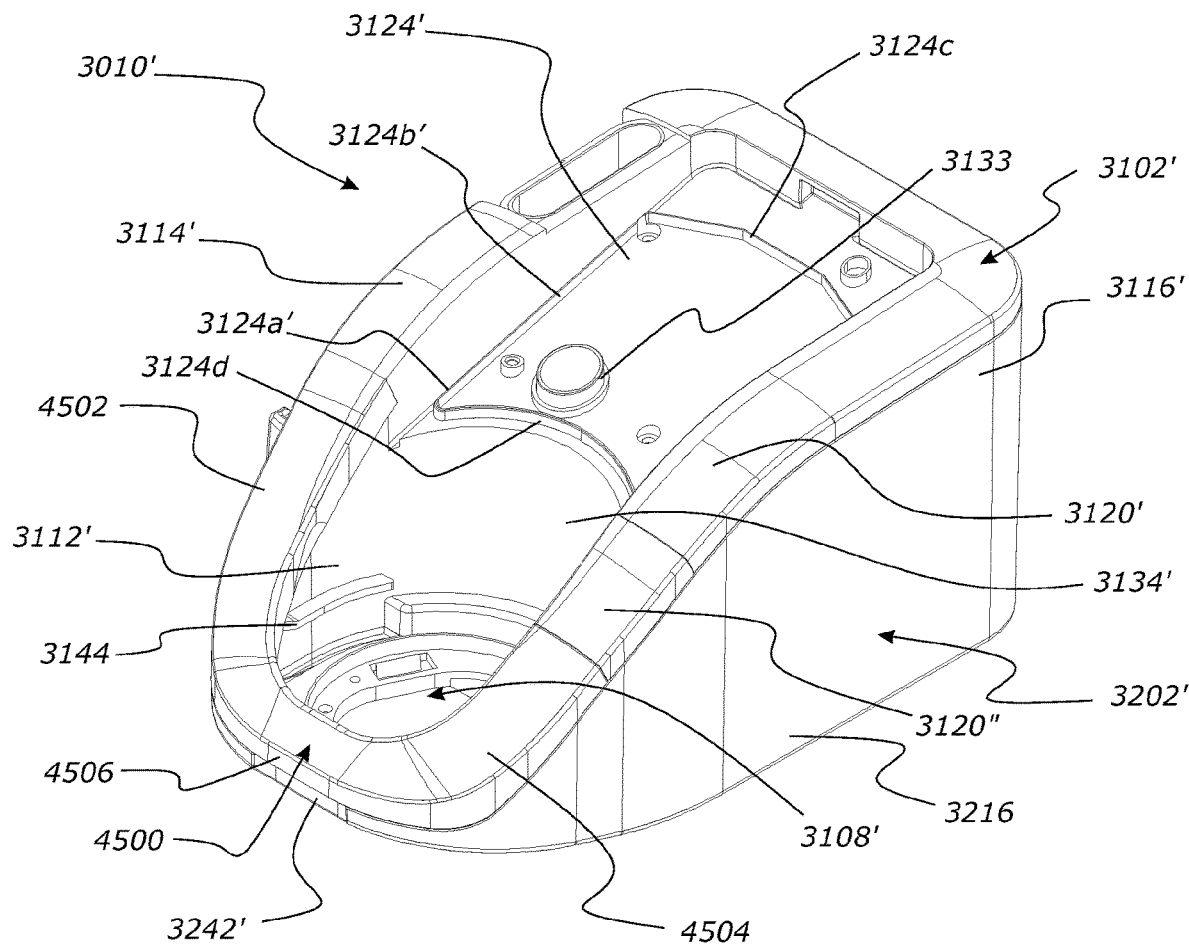
FIGS. 29-33 illustrate various views of other embodiments of the flow therapy apparatus.
Figure 30:
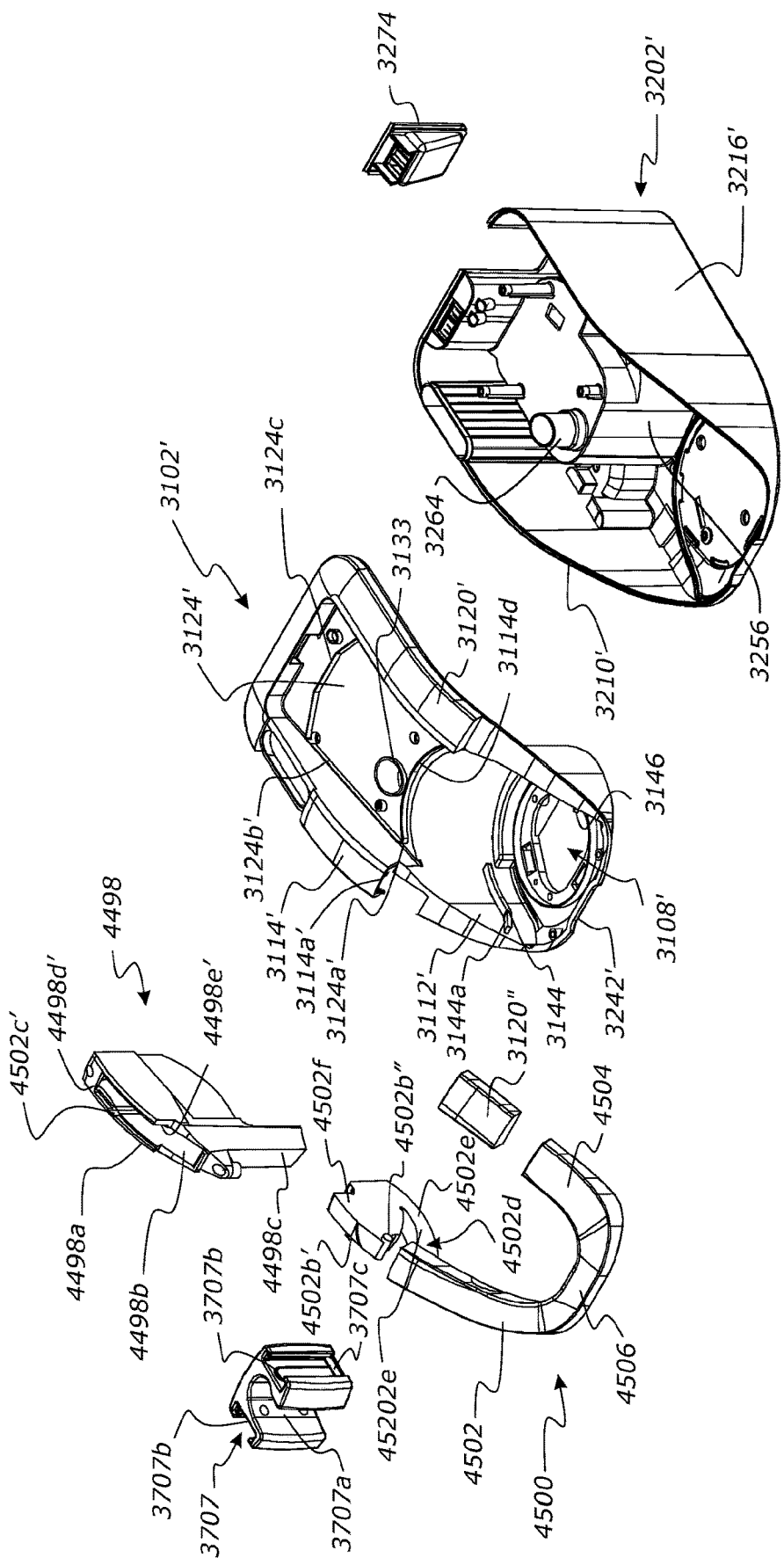
Figure 31:
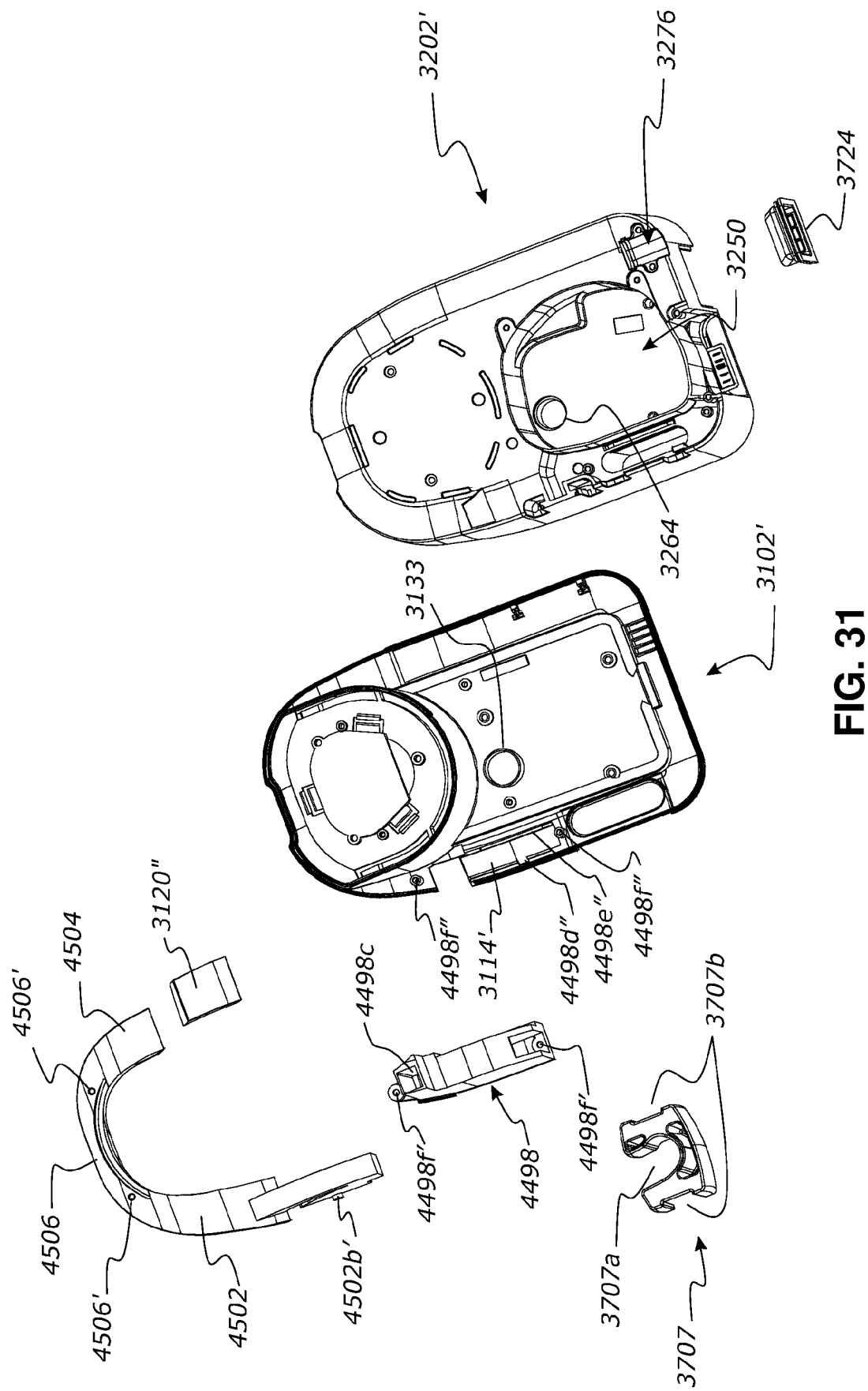
Figure 32:
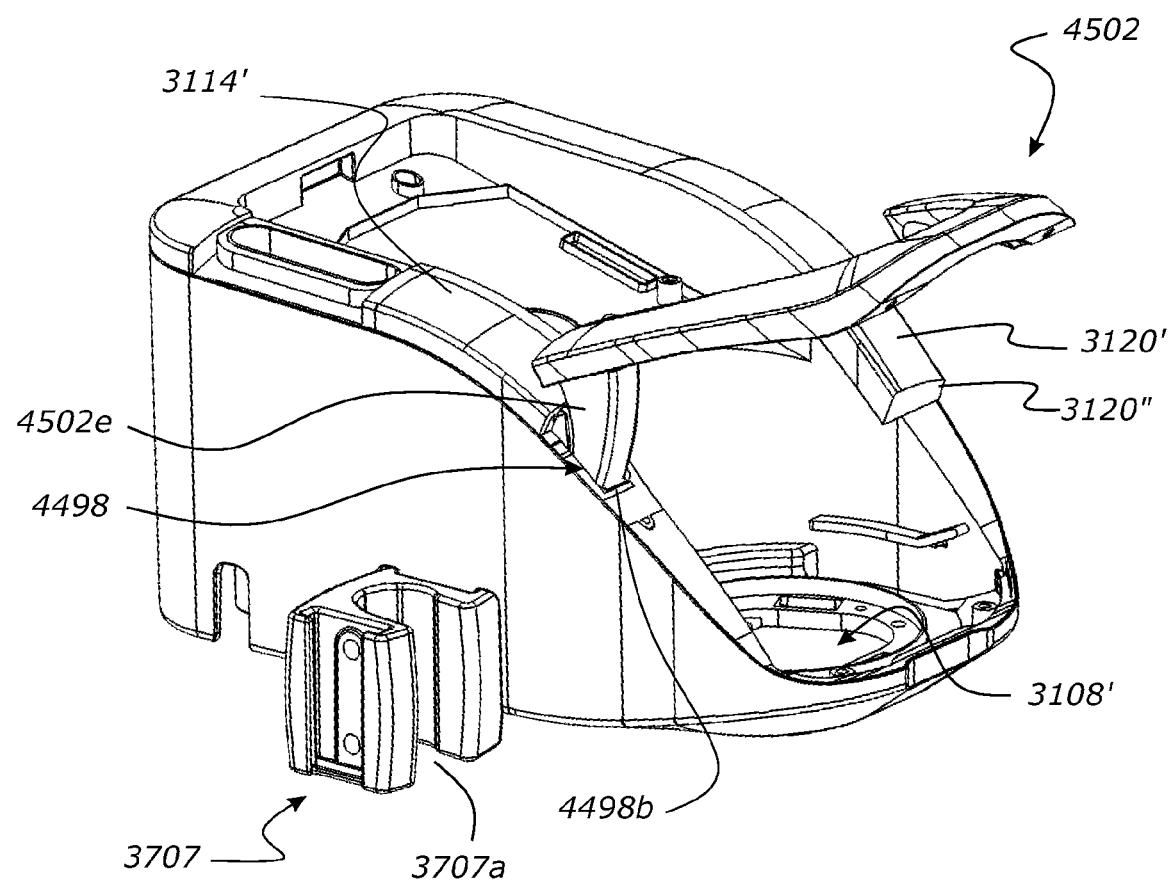
Figure 33:
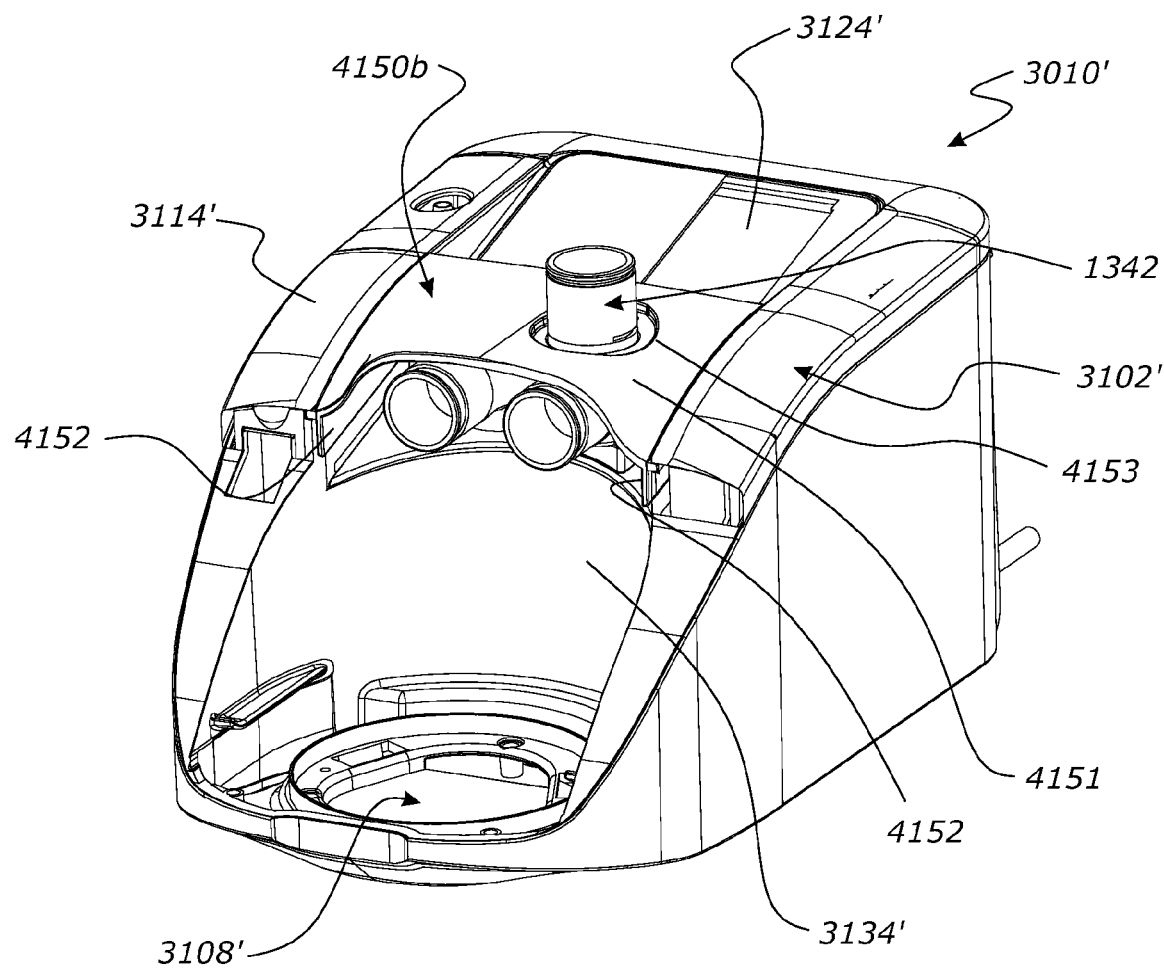

As described above, one barometric sensor is in the flow path and located on the sensing circuit board 2200 of FIG. 22C. The other barometric sensor can be positioned on a printed circuit board that is not located with the gases flow path or a pressurized region of the apparatus but is exposed to ambient temperature. Accordingly, as shown in the flow chart of FIG. 28, the barometric sensor on the sensing circuit board within the flow path provides the absolute pressure of the gases flow $P_F$ to the controller of the system, such as the controller 13 of FIG. 1 or the controller 600 of FIG. 19, at step 2802. The other barometric sensor provides readings on ambient pressure $P_A$ to the controller at step 2804. The controller calculates the difference between these two values, $P_F - P_A$ in step 2806 and outputs the pressure difference as the gauge pressure in the system, $P_G$ in step 2808. The system can use the gauge pressure, $P_G$ to adjust the motor speed curve and correct control of oxygen or gases flow rate. For example, the gauge pressure, $P_G$ can be useful for synchronizing with the patient's breath.

In addition to calculating the gauge pressure in the system, $P_G$ based on readings of the two barometric sensors and improving user safety by eliminating oxygen leak, the dual absolute pressure sensor arrangement also has the following applications and/or advantages.

The absolute pressure sensor in the flow path, such as the barometric sensor 2209 of FIG. 22C, allows small corrections to be made to the oxygen calculation. The absolute pressure sensor positioned in the flow path, such as the barometric sensor 2209 of FIG. 22C, enables comparison between the ultrasonic flow sensors (volumetric flow) and the heated temperature sensing element (mass flow). Large changes in the volumetric flow sensing are not expected in the apparatus as the motor produces a constant volumetric flow. However, for a constant motor the mass flow will change with altitude, temperature or oxygen fraction. The absolute pressure sensor helps to work out the density of gases needed to convert a volumetric flow to a mass flow or vice versa for comparing readings between the ultrasonic flow sensor and the heated temperature sensing element. This can determine the accuracy of the sensors and to make corrections as appropriate. For example, the mass flow can be calculated as:

$$\text{Mass flow} = \text{density} \times \text{volumetric flow}.$$

If the heated temperature sensing element is removed from the system, mass flow rate can still be converted from the volumetric flow rate by using the above equation. Another application of calculating the gauge pressure in the system, $P_G$ based on readings of the two barometric sensors is that the arrangement allows for more defined ranges for leak and blockage algorithms or narrower leak and blockage alarms by factoring the pressure measurement into the algorithm. The conversion between mass flow and volumetric flow is also useful to correct the ultrasonic flow reading based on the heated temperature sensing element. Further, the addition of an ambient pressure sensor allows the conversion between mass flow and volumetric flow to occur such that the system can re-define the limits for different altitudes. As a result, the limits are more specific to the ambient conditions, and can catch a higher number of leakage/blockage events with a higher accuracy.

Specifically, a blockage alarm occurs if the blower can only maintain a flow rate by working at a higher than expected blower speed. Thus, if altitude increases, the mass flow will decrease, which means the blower speed has to increase to deliver the desired mass flow. As a result, the system can detect a blockage because with a pressure sensor, the limits for blockage can be adjusted so that at higher altitudes the system knows to expect higher motor speeds for a given mass flow rate, and similarly at lower altitudes the system knows to expect lower motor speeds for a given mass flow rate.

Similarly, the leakage alarm can occur if the blower does not have to work at such a high speed to maintain a desired flow rate, for example, if the chamber is removed from the system (and thus there is less restriction). Without the pressure sensor, at a higher altitude with a decreased mass flow, a lower flow rate will be seen for the same motor speed at a lower altitude, which can confuse the system, and require larger limits to be defined for the system. Thus, being able to re-define the limits for different altitudes means that lower limits can be defined for higher altitudes which can thus pick up more leak/blockage conditions.

More specifically, the absolute pressure sensor in the flow path allows corrections to be made in response to the partial pressure of water vapour in the gas. In any humidity algorithm is it useful to know the water content of the incoming gases, which depends on the pressure. Particularly, for a power-based humidity control algorithm, characteristics of the gases are measured at the inlet, prior to the gases being humidified, and generated humidity is estimated based on the power input into the heater plate to heat the water and these gas characteristics. In this case the pressure has a large effect on the accuracy of the humidity estimate, because the mass of water required to achieve a given dew-point temperature depends heavily on the ambient pressure. The gauge pressure can also affect the humidity calculation, although to a smaller extent, based on the pressure drop to the patient outlet port 21, 344 or to the patient, such as via the patient interface 8, which produces a corresponding drop in dew-point temperature.

Although only the raw ambient pressure values is measured and fed into the apparatus, altitude can be computed either manually or automatically using various algorithms, and be used as a check for the system. For example, the apparatus can calculate the altitude based on the pressure reading and display the calculated altitude to the user to determine if this is a realistic reading from the apparatus. In another example, the apparatus can prompt the user to confirm the displayed altitude is correct, or the apparatus can request the user to enter the altitude level.

In some embodiments, the system can use an absolute pressure sensor positioned outside of the flow path or pressurized region and exposed to ambient temperature, or other locations suitable for reading the ambient pressure with a gauge pressure sensor between the control board and the sensing module or sensing chamber. The system can determine the total pressure being delivered to the patient by adding the differential pressure by the gauge pressure sensor and the ambient pressure reading by the absolute pressure sensor.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The term "about" is employed herein to mean within standard measurement accuracy.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (e.g., not all described acts or events are necessary for the practice of the algorithms). Moreover, in certain embodiments, acts or events can be performed concurrently, e.g., through multithreaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A flow therapy apparatus comprising:
an inlet port which receives a flow of gases from at least two different gas sources;
a blower which receives the flow of gases from the inlet port, the blower configured to mix the flow of gases from the at least two different gas sources to produce mixed gases, the blower being a combined blower and mixer;
a gases flow path which receives the mixed gases from the blower, the gases flow path configured to direct the flow of gases through a sensing chamber defined by a casing in fluid communication with the gases flow path such that a portion of the gases flow path is defined between an entrance and an exit of the casing, the sensing chamber comprising a sensing circuit board entirely positioned within the casing, wherein a first portion of the sensing circuit board is positioned at least partially within the portion of the gases flow path, wherein the sensing circuit board comprises at least a second portion of the sensing circuit board positioned within the casing outside of the portion of the gases flow path, the sensing chamber further comprising a seal dividing the first portion of the sensing circuit board from the second portion of the sensing circuit board; and
one or more sensors located on the sensing circuit board, the one or more sensors configured to measure a property of the flow of gases flowing through the gases flow path, the one or more sensors located after the blower, wherein positioning the one or more sensors after the blower allows the blower to be a mixer.

2. The apparatus of claim 1, wherein the inlet port comprises a valve configured to receive the flow of gases from an oxygen gas source.

3. The apparatus of claim 2, wherein the valve comprises a proportional valve.

4. The apparatus of claim 1, wherein the one or more sensors comprise two or more ultrasonic transducers.

5. The apparatus of claim 4, wherein the ultrasonic transducers are configured to determine a gas concentration.

6. The apparatus of claim 4, wherein the ultrasonic transducers are configured to determine a flow rate.

7. The apparatus of claim 1, wherein the one or more sensors comprise a gas concentration sensor.

8. The apparatus of claim 1, wherein the one or more sensors comprise a heated temperature sensing element.

9. The apparatus of claim 8, wherein the heated temperature sensing element is configured to determine a flow rate.

10. The apparatus of claim 1, wherein the seal is a pneumatic seal.

11. The apparatus of claim 1, wherein the one or more sensors comprise a gas flow sensor and a temperature sensor, wherein the sensing circuit board is configured to effect thermal conduction between the gas flow sensor and the temperature sensor, and impede thermal conduction between a wall of the sensing chamber and the temperature sensor.

12. The apparatus of claim 1, wherein the second portion of the sensing circuit board comprises a microprocessor.

13. The apparatus of claim 1, wherein the one or more sensors are located on the first portion of the sensing circuit board.

* * * * *